(12) United States Patent
Sinha et al.

(10) Patent No.: US 7,794,983 B2
(45) Date of Patent: Sep. 14, 2010

(54) METHOD FOR GENETIC DETECTION USING INTERSPERSED GENETIC ELEMENTS

(75) Inventors: Sudhir K. Sinha, New Orleans, LA (US); Anthony B. Carter, New Orleans, LA (US)

(73) Assignee: Life Genetics Lab, LLC., Metairie, LA (US)

( * ) Notice: Subject to any disclaimer, the term of this patent is extended or adjusted under 35 U.S.C. 154(b) by 335 days.

(21) Appl. No.: 11/826,020

(22) Filed: Jul. 11, 2007

(65) Prior Publication Data

US 2008/0206755 A1 Aug. 28, 2008

Related U.S. Application Data

(60) Provisional application No. 60/902,850, filed on Feb. 23, 2007.

(51) Int. Cl.
*C12P 19/34* (2006.01)
*C07H 21/04* (2006.01)

(52) U.S. Cl. .................................. 435/91.2; 536/24.33

(58) Field of Classification Search ........................ None
See application file for complete search history.

(56) References Cited

OTHER PUBLICATIONS

Sell et al. An improved assay for genotyping the common Alu insertion in the tissue-type plasminogen activation gene PLAT. Genetic Testing 6(1):67-68 (2002).*
GenBank accession No. K03021 [online] May 3, 1996 [retrieved on Oct. 8, 2009] retrieved from http://www.ncbi.nlm.nih.gov/nuccore/339817.*
Santosh S. Arcot et al., "High-resolution Cartography of Recently Integrated Human Chromosome 19-Specific Alu Fossils",, J. Mol. Biol. (1998) 281, 843-856.
Anthony C. Otieno et al., "Analysis of the Human Alu Ya-lineage", J. Mol. Biol. (2004) 342, 109-118.
G.E. Novick et al., "The Use of Polymorphic Alu Insertions as a New Methodological Alternative in Human Paternity Testing and Child Identification", International Pediatrics/vol. 9/Suppl. 2/ 1994, pp. 60-68.
Gabriel E. Novick et al., "Polymorphic human specific Alu insertions as markers for human identification", Electrophoresis 1995, 16, 1596-1601.
Scott W. Van Arsdell et al., "Direct Repeats Flank Three Small Nuclear RNA Pseudogenes in the Human Genome", Cell, vol. 26, 11-17, Oct. 1981 (Part 1).
F. Sanger et al., "DNA sequencing with chain-terminating inhibitors", Proc. Natl. Acad. Sci. USA vol. 74, No. 12, pp. 5463-5467, Dec. 1977.
Stephen F. Altschul et al., "Basic Local Alignment Search Tool", J. Mol. Biol. (1990) 215, 403-410; and.
Anthony B. Carter et al., "Genome-wide analysis of the human Alu Yb-lineage", Human Genomics, vol. 1, No. 3, Feb. 1-13, 2004.

* cited by examiner

*Primary Examiner*—Samuel Woolwine
(74) *Attorney, Agent, or Firm*—Robert E. Bushnell, Esq.

(57) ABSTRACT

The way to design a "filled" site (which contains an interspersed element) primer set to target a particular locus is to design one of the two primers such that it encompasses that unique information (e.g., interspersed element+flanking genomic sequence+direct repeat). The way to design an "empty" site primer is to design one of the two primers such that the entire direct repeat sequence in addition to flanking genomic sequence is included on both sides. To improve efficiency, the "empty" site primer designed around the direct repeat should not be too long. This primer design of the present invention allows for the ability to test any type of interspersed genetic element containing characteristic direct repeat sequences (direct repeats). This gives the option of many new polymorphic marker sites because Alu elements are not the only interspersed genetic elements having direct repeats flanking their core sequence.

30 Claims, 25 Drawing Sheets

"Filled" Locus

CCTCCCTACAGAA*ATCAACTAGATTTCTTTA*AATTTCCCAGACATCTTAGAAATGAAGGCCGGGCGCGGTGGCTCAC
GCCTGTAATCCCAGCACTTTGGGAGGCCGAGGCGGGTGGATCATGAGGTCAAGAGATCGAGACCATCCTGGCTAA
CAAGGTGAAACCCCGTCTCTACTAAAAATACAAAAAATTAGCCGGGCGCGGTGGCGGGCGCCTGTAGTCCCAGCT
ACTCGGGAGGCTGAGGCAGGAGAATGGCGTGAACCCGGGAAGCGGAGCTTGCAGTGAGCCGAGATTGCGCCACT
GCAGTCCGCAGTCCGGCCTGGGCGACAGAGCGAGACTCCGTCTCAAAAAAAAAAAAAAAAAAAAAAAAAAAAAAA
GAAATGAAAGTCTCTTATCTTAATATAGTTTA*AAGGTGTGTTTCCCTTG*CCCCTC (SEQ ID NO: 1)

"Empty" Locus

CCTCCCTACAGAA*ATCAACTAGATTTCTTTA*AATTTCCCAGACATCTTAGAAATGAAAGTCTCTTATCTTAATATAGT
TTA*AAGGTGTGTTTCCCTTG*CCCCTC (SEQ ID NO: 2)

FIG. 2

"Filled" Locus

ACCCTTTGTAGAGACAGAGTTTCACTACATTGCCCGGGTTGACCAAGCAAAATTTCTTACATGGTCTCATTAA
CAGTTTCTATTTC*TGCTGCCCTTAATCTTTACCAT*CTAAGTGCTTTGGAAGTTTCCTCCCTACAGAAATCAACTAGATTT
CTTTAAATTTCCCAGACATC*TTAGAAATGAA*GGCCGGGCGCGGTGGCTCACGCCTGTAATCCCAGCACTTTGGGAG
GCCGAGGCGGGTGGATCATGAGGTCAAGAGATCGAGACCATCCTGGCTAACAAGGTGAAACCCCGTCTCTAC
TAAAAATACAAAAAATTAGCCGGGCGCGGTGGCGGGCGCCTGTAGTCCCAGCTACTCGGGAGGCTGAGGCAG
GAGAATGGCGTGAACCCGGGAAGCGGAGCTTGCAGTGAGCCGAGATTGCGCCACTGCAGTCCGCAGTCCGGC
CTGGGCGACAGAGCGAGACTCCGTCTCAAAAAAAAAAAAAAAAAAAAAAAAAAAAAAAGAAATGAAAGTC
TCTTATCTTAATATAGTTTAAAGGTGTGTTTCCCTTGCCCCTCAGTATTGTAAATATCTAAACAGATGTGTTGC
CACAAATGGGGCAATTTTTAAATTTAAAAACAATTTTTTTTTTGTATGTGTGCTGGACCAAACCGTGGCATGG
GAGTGATTCCCACATTAAGGAATGTCTCAACATCCTTCATAGCAATTCTTGACTACCAAATCCAGTCTCAATA
TCAAGCATTAATAGAACTATGTATACC (SEQ ID NO: 12)

"Empty" Locus

ACCCTTTGTAGAGACAGAGTTTCACTACATTGCCCGGGTTGACCAAGCAAAATTTCTTACATGGTCTCATTAA
CAGTTTCTATTTC*TGCTGCCCTTAATCTTTACCAT*CTAAGTGCTTTGGAAGTTTCCTCCCTACAGAAATCAACTAGATTT
CTTTAAATTTC*CCAGACATCTTAGAAATGAAAGTCTC*TTATCTTAATATAGTTTAAAGGTGTGTTTCCCTTGCCCCTCAG
TATTGTAAATATCTAAACAGATGTGTTGCCACAAATGGGGCAATTTTTAAATTTAAAAACAATTTTTTTTTG
TATGTGTGCTGGACCAAACCGTGGCATGGGAGTGATTCCCACATTAAGGAATGTCTCAACATCCTTCATAGCA
ATTCTTGACTACCAAATCCAGTCTCAATATCAAGCATTAATAGAACTATGTATACC (SEQ ID NO: 13)

FIG. 5

"Filled" Locus

*CCTCCCTACAGAA*ATCAACTAGATTTCTTTAAATTTCCCAGACATCTT*AGAAATGAA*GGCCGGGCGCGGTGGCTCAC
GCCTGTAATCCCAGCACTTTGGGAGGCCGAGGCGGGTGGATCATGAGGTCAAGAGATCGAGACCATCCTGGCTAA
CAAGGTGAAACCCCGTCTCTACTAAAAATACAAAAAATTAGCCGGGCGCGGTGGCGGGCGCCTGTAGTCCCAGCT
ACTCGGGAGGCTGAGGCAGGAGAATGGCGTGAACCCGGGAAGCGGAGCTTGCAGTGAGCCGAGATTGCGCCACT
GCAGTCCGCAGTCCGGCCTGGGCGACAGAGCGAGACTCCGTCTCAAAAAAAAAAAAAAAAAAAAAAAAAAAAAAA
GAAATGAAAGTCTCTTATCTTAATATAGTTTAAAGGTGTGTTTCCCTTGCCCCTC (SEQ ID NO: 14)

"Empty" Locus

*CCTCCCTACAGAA*ATCAACTAGATTTCTTTAAATTTCCCAGAC*ATCTTAGAAATGAAAGTCTC*TTATCTTAATATAGTT
TAAAGGTGTGTTTCCCTTGCCCCTC (SEQ ID NO: 15)

FIG. 6

"Filled" Locus

AGATCTGTATTTTGCAAATATTTTCTTCAATATGTGGCTTGTCTTTTTGTTCTCTTGACAAGGTCTCTTCCAGAG
TATAAACTGTAAATATTAAGAAATCCACATTGTCATTTCTTCTGTGTATATCAACCTTCTGTGTCATTTGTTAA
AATTCATTACCAAACGCAAAGGCACACAGCTTTTCCTCTATAGTTTCTTCTAGAAATTGTATAGTTTTGCATTT
TTAGTGTAAGGATGATTTTGAGTGATTATTTGTGTAAGTTGTAAAGTTTTCATCTACATGCATATCATTTCTTA
TGGTTTCCAATTAATCATTCCCTCACTATTTTTGGGAAAGACACAGGATAGTGGGCTCTGTTAGAGTAGATAG
CTAGCTAGACATGAACAGGAGGGGG*AGCTCCTGGAAAAGGGAAAG*TCTGTGAAGGCTCACCTGGAGGGACCACCAA
AAATGCACATATTAGTAGCATCTCTAGTGCTGGAGTGGATGGGCACTTGTCAATTGTGGTTAGGAGGGAGAA
GAGGTACCTACGCAGAAACACCCTAGAACTTCTCT*TAAGGTGCCCCAATCGGATGGGCGCGGTGGCTCACGCCTGT
AATCCCAGCACTTTGGGAGGCCGAGGCGGGTGGATCATGAGGTCAGGAGATCGAGACCATCCTGGCTAACAA
GGTGAAACCCCGTCTCTACTAAAAATACAAAAAATTAGCCGGGCACGGTGGCGGGCGCCTGTAGTCCCAGCT
CTTCGGGAGGCTGAGGCAGGAGAATGGCGTGAACCCGGGAAGTGGAGCTTGCATTGAGCCGAGATTGCGCCA
CTGCAGTCCGCAGTCCGGCCTGGGCGACAGAGCGAGACTCCGTCTCAAAAAAAAAAAAAAAAAAAAAGATGC
CCCAATCATCATTCACTCTGCAATAAAAA (SEQ ID NO: 16)

"Empty" Locus

AGATCTGTATTTTGCAAATATTTTCTTCAATATGTGGCTTGTCTTTTTGTTCTCTTGACAAGGTCTCTTCCAGAG
TATAAACTGTAAATATTAAGAAATCCACATTGTCATTTCTTCTGTGTATATCAACCTTCTGTGTCATTTGTTAA
AATTCATTACCAAACGCAAAGGCACACAGCTTTTCCTCTATAGTTTCTTCTAGAAATTGTATAGTTTTGCATTT
TTAGTGTAAGGATGATTTTGAGTGATTATTTGTGTAAGTTGTAAAGTTTTCATCTACATGCATATCATTTCTTA
TGGTTTCCAATTAATCATTCCCTCACTATTTTTGGGAAAGACACAGGATAGTGGGCTCTGTTAGAGTAGATAG
CTAGCTAGACATGAACAGGAGGGGG*AGCTCCTGGAAAAGGGAAAG*TCTGTGAAGGCTCACCTGGAGGGACCACCAA
AAATGCACATATTAGTAGCATCTCTAGTGCTGGAGTGGATGGGCACTTGTCAATTGTGGTTAGGAGGGAGAA
GAGGTACCTACGCAGAAACACCCTAGAACTTCTCT*TAAGGTGCCCCAATCATCATTCACTCTGCAATAAAAA
(SEQ ID NO: 17)

| LOCUS | Filled | Empty | Primer Sequence | |
|---|---|---|---|---|
| Yb8NBC67 | 154 | 156 | Forward:<br>Reverse F:<br>Reverse E: | TGTGTCAAAGAGCGAGATGAACA [SEQ ID NO:18]<br>GGGTTCACGCCATTCTAGC [SEQ ID NO:19]<br>TTCATAGCAGCCTATTCTAGCAG [SEQ ID NO:20] |
| Ya5NBC241 | 105 | 103 | Forward:<br>Reverse F:<br>Reverse E: | aaacataatttagttccccacaa [SEQ ID NO:21]<br>cccggccaagatccattc [SEQ ID NO:22]<br>cccccagaagaaccattct [SEQ ID NO:23] |
| Yb8NBC237 | 212 | 212 | Forward:<br>Reverse F:<br>Reverse E: | GCCACTCGTAGGCAGTCATT [SEQ ID NO:24]<br>GCCCGGCCGTTACGGTTT [SEQ ID NO:25]<br>AGCATGTCAACTGTTACGTATG [SEQ ID NO:26] |
| YC1NBC60 | 234 | 239 | Forward:<br>Reverse F:<br>Reverse E: | CATAGCACCAGGTGACCACA [SEQ ID NO:27]<br>GCGCCCGGCCTCTTTCTT [SEQ ID NO:28]<br>AAAGGTTAAACCATCTTCTTTCTACA [SEQ ID NO:29] |
|  | 178 | 183 | Forward:<br>Reverse F:<br>Reverse E: | GCACTTCACACCATTTCTGC [SEQ ID NO:30]<br>GCGCCCGGCCTCTTTCTT [SEQ ID NO:31]<br>AAAGGTTAAACCATCTTCTTTCTACA [SEQ ID NO:32] |
| Ya5AC2305 | 130 | 129 | Forward:<br>Reverse F:<br>Reverse E: | AGGACAGGTTAATAATCCAGAAAAA [SEQ ID NO:33]<br>CGGCCCCAATTACAACTCT [SEQ ID NO:34]<br>CTTTGATTACAACTCTTAAGGAAACG [SEQ ID NO:35] |
| Ya5ACA1736 | 107 | 112 | Forward:<br>Reverse F:<br>Reverse E: | CCTGCTCTGCACACTTCTTG [SEQ ID NO:36]<br>CCGGCCCGAGAAGGCAAT [SEQ ID NO:37]<br>GACCTTGACCTAGAGAAGGCAAT [SEQ ID NO:38] |
|  | 150 | 156 | Forward:<br>Reverse F:<br>Reverse E: | CAACGTCCTCCCTAACTACCC [SEQ ID NO:39]<br>SAME<br>TGACCTTGACCTAGAGAAGGCAA [SEQ ID NO:40] |
|  | 213 | 219 | Forward:<br>Reverse F:<br>Reverse E: | CCACCTCATGAACTCCCACT [SEQ ID NO:41]<br>SAME<br>SAME |
| Yb8AC1197 | 105 | 104 | Forward:<br>Reverse F:<br>Reverse E: | TGCTGCCCTTAATCTTTACCA [SEQ ID NO:3]<br>CCCGGCCTTCATTTCTAAG [SEQ ID NO:4]<br>GAGACTTTCATTTCTAAGATGTCTGG [SEQ ID NO:5] |
| Yb8NBC126 | 177 | 178 | Forward:<br>Reverse F:<br>Reverse E: | AGCTCCTGGAAAAGGGAAAG [SEQ ID NO:9]<br>ATCCGATTGGGGCACCTTA [SEQ ID NO:10]<br>ATGATGATTGGGGCACCTTA [SEQ ID NO:11] |
|  | 156 | 157 | Forward:<br>Reverse F:<br>Reverse E: | CTGTGAAGGCTCACCTGGAG [SEQ ID NO:42]<br>ATCCGATTGGGGCACCTTA [SEQ ID NO:43]<br>ATGATGATTGGGGCACCTTA [SEQ ID NO:44] |

FIG. 10B

| LOCUS | Filled | Empty | Primer Sequence | |
|---|---|---|---|---|
| Ya5ac2458 | 246 | 247 | Forward:<br>Reverse F:<br>Reverse E: | AGGGGGAATCGAGTGCTTAT [SEQ ID NO:45]<br>GGCCCCCTGGAATCTTAAC [SEQ ID NO:46]<br>GACCCTCCTGGAATCTTAACC [SEQ ID NO:47] |
| | 206 | 207 | Forward:<br>Reverse F:<br>Reverse E: | TGTTGGATATCCTGGCTGAA [SEQ ID NO:48]<br>GGCCCCCTGGAATCTTAAC [SEQ ID NO:46]<br>GACCCTCCTGGAATCTTAACC [SEQ ID NO:47] |
| | 246 | 247 | Forward:<br>Reverse F:<br>Reverse E: | AGGGGGAATCGAGTGCTTAT [SEQ ID NO:49]<br>GGCCCCCTGGAATCTTAAC [SEQ ID NO:50]<br>GACCCTCCTGGAATCTTAACC [SEQ ID NO:51] |
| Ya5ACA1736 | 241 | 248 | Forward:<br>Reverse F:<br>Reverse E: | TTCCATCTACCTAGAAGTTCCTCA [SEQ ID NO:52]<br>CGAGAAGGCAATTTTCTACTTAGG [SEQ ID NO:53]<br>TTGACCTAGAGAAGGCAATTTTC [SEQ ID NO:54] |
| | 213 | 219 | Forward:<br>Reverse F:<br>Reverse E: | CCACCTCATGAACTCCCACT [SEQ ID NO:55]<br>CCGGCCCGAGAAGGCAAT [SEQ ID NO:56]<br>GACCTTGACCTAGAGAAGGCAAT [SEQ ID NO:57] |
| | 150 | 156 | Forward:<br>Reverse F:<br>Reverse E: | CAACGTCCTCCCTAACTACCC [SEQ ID NO:58]<br>CCGGCCCGAGAAGGCAAT [SEQ ID NO:59]<br>GACCTTGACCTAGAGAAGGCAAT [SEQ ID NO:60] |
| | 106 | 112 | Forward:<br>Reverse F:<br>Reverse E: | CCTGCTCTGCACACTTCTTG [SEQ ID NO:61]<br>SAME<br>SAME |
| Ya5ac2265 | 187 | 189 | Forward:<br>Reverse F:<br>Reverse E: | CAGCTCAGTCCTAAGCCACA [SEQ ID NO:62]<br>CCGGCCCAGTTTCTTAATG [SEQ ID NO:63]<br>CATGAATTCAGTTTCTTAATGATAAGG [SEQ ID NO:64] |
| | 102 | 103 | Forward:<br>Reverse F:<br>Reverse E: | AGAAGAGTGAATGCACATTTATGA [SEQ ID NO:65]<br>CCGGCCCAGTTTCTTAATG [SEQ ID NO:66]<br>CATGAATTCAGTTTCTTAATGATAAGG [SEQ ID NO:67] |
| Ya5aca1153 | 123 | 125 | Forward:<br>Reverse F:<br>Reverse E: | CAGTGAAAGCTTCTTAGGGGAAT [SEQ ID NO:68]<br>CCGGCCCTGTGTCTTCTT [SEQ ID NO:69]<br>TGTCCTTCTGTGTCTTCTTAAATATC [SEQ ID NO:70] |
| Yb7AD155 | 100 | 101 | Forward:<br>Reverse F:<br>Reverse E: | GTACACATTAAGCACATGGAAGTCA [SEQ ID NO:71]<br>GCCCGGCCGTTCTTTTTC [SEQ ID NO:72]<br>GCATGAAATGTTCTTTTTCATCTC [SEQ ID NO:73] |
| Yb8NBC622 | 150 | 150 | Forward:<br>Reverse F:<br>Reverse E: | TCAAAACTTGCGGATTTTCC [SEQ ID NO:74]<br>GCGCAATCTCGGCTCCTT [SEQ ID NO:75]<br>TGTGCAGGGGAATTCCTTCTAA [SEQ ID NO:76] |
| | 118 | 118 | Forward:<br>Reverse F:<br>Reverse E: | TGGAATACAATGTAACTGGGGATATG [SEQ ID NO:77]<br>SAME<br>SAME |

FIG. 10C

| LOCUS | Filled | Empty | Primer Sequence | |
|---|---|---|---|---|
| Ya5NBC327 | 173 | 171 | Forward:<br>Reverse F:<br>Reverse E: | CTGGGGATATTTTCATAGATGC [SEQ ID NO:78]<br>GCCCGGCCCTCATTATTC [SEQ ID NO:79]<br>CCCATTCTCATTATTCTTATTCAACA [SEQ ID NO:80] |
| | 128 | 134 | Forward:<br>Reverse F:<br>Reverse E: | TGATGTCATGTACAAACAGGGATA [SEQ ID NO:81]<br>GCCCGGCCCTCATTATTC [SEQ ID NO:82]<br>CAAGGATACCCATTCTCATTATTCTTA [SEQ ID NO:83] |
| SVA<br>(chr 2) | 113 | 112 | Forward:<br>Reverse F:<br>Reverse E: | aagccctgaaaagtgaaat [SEQ ID NO:84]<br>GGAGAGGGGTCAAATTCTTa [SEQ ID NO:85]<br>tttctggtTCAAATTCTTatctatcaa [SEQ ID NO:86] |
| HS-1<br>(chr 1) | 110 | 109 | Forward:<br>Reverse F:<br>Reverse E: | aaacaggaagcatttcgaggt [SEQ ID NO:87]<br>GCCCAGCCTCACATAGAt [SEQ ID NO:88]<br>aaaaatgGCACATAGAtgttgaa [SEQ ID NO:89] |
| Y<br>(chr 1) | 102 | 101 | Forward:<br>Reverse F:<br>Reverse E: | ccctgaatctgagtgggact [SEQ ID NO:90]<br>CCGGCCGGCACTTTTatg [SEQ ID NO:91]<br>tgcatGGCACTTTTatgact [SEQ ID NO:92] |
| | 108 | 108 | Forward:<br>Reverse F:<br>Reverse E: | SAME<br>SAME<br>cagaaatgcatGGCACTTTTat [SEQ ID NO:93] |
| YC1<br>(Chr 1 or 2) | 119 | 118 | Forward:<br>Reverse F:<br>Reverse E: | ttcctcttttctccatttgtt [SEQ ID NO:94]<br>GGCCTCCCAAGGATTCTTTa [SEQ ID NO:95]<br>ccttgcttggGGATTCTTTa [SEQ ID NO:96] |
| YE5<br>(Chr1 or 2) | 55111 | 100 | Forward:<br>Reverse F:<br>Reverse E: | ggtgtagcagaacagacaggag [SEQ ID NO:97]<br>AAGTGCTGGCTGTTCACCAc [SEQ ID NO:98]<br>ggtttCTGTTCACCActttca [SEQ ID NO:99] |
| | 100 | 100 | Forward:<br>Reverse F:<br>Reverse E: | tagcagaacagacaggagacca [SEQ ID NO:100]<br>SAME<br>ttggggtttCTGTTCACCAc [SEQ ID NO:101] |
| | 100 | 105 | Forward:<br>Reverse F:<br>Reverse E: | ggtgtagcagaacagacaggag [SEQ ID NO:102]<br>AAGTGCTGGCTGTTCACCAc [SEQ ID NO:103]<br>ggtttCTGTTCACCActttca [SEQ ID NO:104] |
| YG6<br>(chr 1 or 2) | 100 | 100 | Forward:<br>Reverse F:<br>Reverse E: | acagctgggcaatacgttct [SEQ ID NO:105]<br>CCGGCCAAGATTTTCATTt [SEQ ID NO:106]<br>gagccaAAGATTTTCATTttgatg [SEQ ID NO:107] |
| | 100 | 102 | Forward:<br>Reverse F:<br>Reverse E: | SAME<br>SAME<br>cagagccaAAGATTTTCATTtt [SEQ ID NO:108] |
| YG6<br>(chr 1 or 2) | 100 | 101 | Forward:<br>Reverse F:<br>Reverse E: | ttgcagaatgggtttggaag [SEQ ID NO:109]<br>CCGGCCTTTACCAAACTT [SEQ ID NO:110]<br>gctgaacTTTACCAAACTTttaaagaa [SEQ ID NO:110] |

FIG. 10D

| LOCUS | Filled | Empty | Primer Sequence | |
|---|---|---|---|---|
| YA1 (chr 1 or 2) | 103 | 100 | Forward:<br>Reverse F:<br>Reverse E: | agaaggaagaagctccaaacgtg [SEQ ID NO:112]<br>CTCCTGCGTGGCTTCATT [SEQ ID NO:113]<br>tgacttGGCTTCATTCTTcggtga [SEQ ID NO:114] |
| | 103 | 102 | Forward:<br>Reverse F:<br>Reverse E: | SAME<br>SAME<br>actgacttGGCTTCATTCTTcg [SEQ ID NO:115] |
| YA4 (chr 1) | 111 | 111 | Forward:<br>Reverse F:<br>Reverse E: | ttaagaaagtcagcagaaaacttc [SEQ ID NO:116]<br>CCCGGCCCAGATTTTACT [SEQ ID NO:117]<br>ggtcttaCAGATTTTACTTttatttgc [SEQ ID NO:118] |
| YA5 (chr 2) | 102 | 100 | Forward:<br>Reverse F:<br>Reverse E: | acagaggccaccctgtaggt [SEQ ID NO:119]<br>ACCTGGCCCTGGGTGACTg [SEQ ID NO:120]<br>tgagaCTGGGTGACTgtgtttt [SEQ ID NO:121] |
| | 102 | 105 | Forward:<br>Reverse F:<br>Reverse E: | SAME<br>SAME<br>tgaaatgagaCTGGGTGACTgt [SEQ ID NO:122] |
| SVA (chr 3) | 101 | 102 | Forward:<br>Reverse F:<br>Reverse E: | aaagctgggtttccttttgc [SEQ ID NO:123]<br>GCTGGCCGGAAGTCTTaat [SEQ ID NO:124]<br>tgaaggataGAAGTCTTaatgcag [SEQ ID NO:125] |
| YC1 (chr 3) | 110 | 113 | Forward:<br>Reverse F:<br>Reverse E: | cccaataaaatcagcaaatatga [SEQ ID NO:126]<br>CCGGCCCCCACATTTCTT [SEQ ID NO:127]<br>tgacttttCCACATTTCTTacattg [SEQ ID NO:128] |
| YB8 (chr 3) | 105 | 108 | Forward:<br>Reverse F:<br>Reverse E: | tgctgcccttaatctttacca [SEQ ID NO:129]<br>CCCGGCCTTCATTTCTaag [SEQ ID NO:130]<br>ataagagactTTCATTTCTaagatgtc [SEQ ID NO:131] |
| YA5 (chr 4) | 103 | 101 | Forward:<br>Reverse F:<br>Reverse E: | ccattaaaggaacaagaatgga [SEQ ID NO:132]<br>GCCCGGCCAGTAATCTTTa [SEQ ID NO:133]<br>ctggtcCAGTAATCTTTaatacact [SEQ ID NO:134] |
| Y (chr 5) | 100 | 100 | Forward:<br>Reverse F:<br>Reverse E: | gtttacctgccttctggctct [SEQ ID NO:135]<br>GCCCAGCCTACTCTTGTTa [SEQ ID NO:136]<br>attacctcTACTCTTGTTaaccaacca [SEQ ID NO:137] |
| YA5 (chr 5) | 100 | 101 | Forward:<br>Reverse F:<br>Reverse E: | tttcttagttctttaacaacagatgc [SEQ ID NO:138]<br>TATCCTTGCTAGAAGTTactgga [SEQ ID NO:139]<br>attccaaaaAGAAGTTactggat [SEQ ID NO:140] |
| YA5 (chr 5) | 100 | 101 | Forward:<br>Reverse F:<br>Reverse E: | aatacagccaaatgaactggaga [SEQ ID NO:141]<br>TCTGGCCTCCATTTAGTatttt [SEQ ID NO:142]<br>gcactctctATTTAGTattttctcg [SEQ ID NO:143] |
| LINE (chr 7) | 103 | 101 | Forward:<br>Reverse F:<br>Reverse E: | tgcacacgtatgtttattgcag [SEQ ID NO:144]<br>TCCTCCCCTCCATTTTCTTa [SEQ ID NO:145]<br>atatatgCCATTTTCTTaatccagtc [SEQ ID NO:146] |

FIG. 10E

| LOCUS | Filled | Empty | Primer Sequence | |
|---|---|---|---|---|
| YB8 (chr 7) | 100 | 100 | Forward:<br>Reverse F:<br>Reverse E: | taatatgaggtgatgggggtta [SEQ ID NO:147]<br>CCGGCCGCCAGTTTCTTa [SEQ ID NO:148]<br>cccagaaCCAGTTTCTTaaatagc [SEQ ID NO:149] |
| YB8 (chr 7) | 110 | 113 | Forward:<br>Reverse F:<br>Reverse E: | tcttgataacatagggaaaatcacttc [SEQ ID NO:150]<br>CCGGCCCAGAGTTCTTaat [SEQ ID NO:151]<br>tgttttgtaCAGAGTTCTTaattgcag [SEQ ID NO:152] |
| YB8 (chr 7) | 106 | 107 | Forward:<br>Reverse F:<br>Reverse E: | ggctagccatatggagaagaa [SEQ ID NO:153]<br>CCGGCCGGAATTCTTatag [SEQ ID NO:154]<br>ttcttctGGAATTCTTatagtttgagg [SEQ ID NO:155] |
| LINE (chr 8) | 101 | 100 | Forward:<br>Reverse F:<br>Reverse E: | agcttgagggtggctgtgt [SEQ ID NO:156]<br>GCTCACGCTCTGTGAGTGtt [SEQ ID NO:157]<br>agagagattTGTGAGTGtttaaagatg [SEQ ID NO:158] |
| SG1 (chr 8) | 103 | 100 | Forward:<br>Reverse F:<br>Reverse E: | ttttcggttgtgaactgaagg [SEQ ID NO:159]<br>CCCAGCCTTAAACTGACCat [SEQ ID NO:160]<br>gccccTAAACTGACCattctt [SEQ ID NO:161] |
|  | 103 | 103 | Forward:<br>Reverse F:<br>Reverse E: | SAME<br>SAME<br>ccagccccTAAACTGACCat [SEQ ID NO:162] |
| LINE (chr 9) | 119 | 118 | Forward:<br>Reverse F:<br>Reverse E: | aagacccaaattagcgaaagaa [SEQ ID NO:163]<br>AAACCTAGGCATTACCTTTTCaa [SEQ ID NO:164]<br>catttgtcgtTTACCTTTTCaa [SEQ ID NO:165] |
| YG9 (chr 9) | 114 | 106 | Forward:<br>Reverse F:<br>Reverse E: | ctctatatgcactacagttttgtga [SEQ ID NO:166]<br>CCGGCCCCAAGTGTTtta [SEQ ID NO:167]<br>ccccagaattaCCAAGTGTTtt [SEQ ID NO:168] |
| YG6 (chr 10) | 100 | 105 | Forward:<br>Reverse F:<br>Reverse E: | gaacatccagcaccaaatcc [SEQ ID NO:169]<br>CCCGGCCCTACCTTCtta [SEQ ID NO:170]<br>cctggttgtgtgtTACCTTCtt [SEQ ID NO:171] |
| YC1 (chr 10) | 100 | 104 | Forward:<br>Reverse F:<br>Reverse E: | aggcaggcagatcacttgag [SEQ ID NO:172]<br>CGCGCCCCTAATTCTTTct [SEQ ID NO:173]<br>ccatgcctggCTAATTCTTTc [SEQ ID NO:174] |
| YC1 (chr 10) | 111 | 114 | Forward:<br>Reverse F:<br>Reverse E: | aggggtgagggataaaaga [SEQ ID NO:175]<br>TGAGCCACCGATGAATAAGTT [SEQ ID NO:176]<br>ggtatttggttacATGAATAAGTTCt [SEQ ID NO:177] |
| YC2 (chr 12) | 109 | 117 | Forward:<br>Reverse F:<br>Reverse E: | gagcacattacctataggcagaca [SEQ ID NO:178]<br>GCCCGGCCTTATTTTAGttt [SEQ ID NO:179]<br>tgggttgatagttattTTATTTTAGtt [SEQ ID NO:180] |
| YA5 (chr 13) | 101 | 104 | Forward:<br>Reverse F:<br>Reverse E: | gggattggatagaatgaagaaagg [SEQ ID NO:181]<br>GCCCGGCCTCTCTCTTTag [SEQ ID NO:182]<br>cgcgctctctcTCTCTCTTTag [SEQ ID NO:183] |

FIG. 10F

| LOCUS | Filled | Empty | Primer Sequence | |
|---|---|---|---|---|
| YA5 (chr 13) | 103 | 111 | Forward:<br>Reverse F:<br>Reverse E: | agaagagtgaatgcacatttatga [SEQ ID NO:184]<br>CCCGGCCCAGTTTCTTaat [SEQ ID NO:185]<br>gggagtcatgaattCAGTTTCTTa [SEQ ID NO:186] |
| LINE (chr 15) | 105 | 104 | Forward:<br>Reverse F:<br>Reverse E: | tcctactctcatttcttcacattca [SEQ ID NO:187]<br>CTTGTAAATTTGTCTTGAGTTcattg [SEQ ID NO:188]<br>ggctgtgtgcttTTGAGTTc [SEQ ID NO:189] |
| Sp (chr 17) | 109 | 110 | Forward:<br>Reverse F:<br>Reverse E: | gggaggacattgaaggtaaaca [SEQ ID NO:190]<br>ACCTGGCTGATTGCAGtttt [SEQ ID NO:191]<br>gggccattTGATTGCAGtt [SEQ ID NO:192] |
| Y (chr 17) | 103 | 110 | Forward:<br>Reverse F:<br>Reverse E: | gaggctgcagtgagctatga [SEQ ID NO:193]<br>GCCCGGCCAATTTACAGc [SEQ ID NO:194]<br>aagaactcattcagaAATTTACAGc [SEQ ID NO:195] |
| Y (chr 19) | 105 | 110 | Forward:<br>Reverse F:<br>Reverse E: | tagagtgctgctgtggcaaa [SEQ ID NO:196]<br>GCCCAGCCTAGTGTCCTCT [SEQ ID NO:197]<br>ttctcctggttacTAGTGTCCTCTc [SEQ ID NO:198] |
| YA5 (chr 20) | 108 | 112 | Forward:<br>Reverse F:<br>Reverse E: | ccaagtcaggtataagcctcaga [SEQ ID NO:199]<br>GCCGGATGTCCACTCTtaaa [SEQ ID NO:200]<br>acagaaaggatgtCCACTCtta [SEQ ID NO:201] |
| YA5 (chr 3) | 145 | 141 | Forward:<br>Reverse F:<br>Reverse E: | caggcctggtggtaacaaat [SEQ ID NO:202]<br>CTCGGCCTCCCAATCAAC [SEQ ID NO:203]<br>ggccaatatTCAACATTCTTa [SEQ ID NO:204] |
| YA5 (chr 3) | 158 | 145 | Forward:<br>Reverse F:<br>Reverse E: | ccctggacttaccctatctca [SEQ ID NO:205]<br>TGCTGGGATTACATGGATTTT [SEQ ID NO:206]<br>ggagaatgtgtgTGGATTTTATTc [SEQ ID NO:207] |
| SP Chr 22 | 110 | | Forward:<br>Reverse F:<br>Reverse E: | ctttggccctgagagagatg [SEQ ID NO:208]<br>ACACCCCACCAAAACTGAAT [SEQ ID NO:209]<br>ttttaaaaccgAATGCCTTt [SEQ ID NO:210] |
| YE (chr 1) | 117 | 113 | Forward:<br>Reverse F:<br>Reverse E: | agcagctctgggtgtagcag [SEQ ID NO:211]<br>CCAAAGTGCTGGCTGTTCA [SEQ ID NO:212]<br>tggggtttCTGTTCACCAct [SEQ ID NO:213] |
| YG6 (chr 2) | 103 | 102 | Forward:<br>Reverse F:<br>Reverse E: | acagctgggcaatacgttct [SEQ ID NO:214]<br>CGCCCGGCCAAGATTTTC [SEQ ID NO:215]<br>cagagccaAAGATTTTCATTtt [SEQ ID NO:216] |
| YC1 (chr 2) | 125 | 122 | Forward:<br>Reverse F:<br>Reverse E: | tctttcctcttttctccattttg [SEQ ID NO:217]<br>CTCGGCCTCCCAAGGATT [SEQ ID NO:218]<br>ccttgcttggGGATTCTTTa [SEQ ID NO:219] |
| Ya5/8 (Chr 1) | 149 | 144 | Forward:<br>Reverse F:<br>Reverse E: | gtctgcagcttcactcctga [SEQ ID NO:220]<br>CATTCTCCTGCGTGGCTTC [SEQ ID NO:221]<br>tgacttGGCTTCATTCTTcg [SEQ ID NO:222] |

FIG. 10G

| LOCUS | Filled | Empty | Primer Sequence | |
|---|---|---|---|---|
| YB3A2 (chr 4) | 105 | 103 | Forward: Reverse F: Reverse E: Forward: Reverse F: Reverse E: | caggagaacatggccttcac [SEQ ID NO:223] CGCCCAGCCTATCCTTTT [SEQ ID NO:224] atgtctTATCCTTTTgccttttg [SEQ ID NO:225] SAME SAME ttgcctttatgtctTATCCTTTTg [SEQ ID NO:226] |
| YB10 (chr 5) | 110 | 115 | Forward: Reverse F: Reverse E: | agatatgcccaaaggacacaa [SEQ ID NO:227] GCCCGGCCGAAACTATTa [SEQ ID NO:228] tcccctccatgtGAAACTATTa [SEQ ID NO:229] |
| Y (chr 5) | | | Forward: Reverse F: Reverse E: | ctcattccctttcccactc [SEQ ID NO:230] GCCCAGCCTACTCTTGTTa [SEQ ID NO:231] attacctcTACTCTTGTTaaccaacca [SEQ ID NO:232] |
| Y (chr 5) | | | Forward: Reverse F: Reverse E: | SAME SAME tgctaacattacctcTACTCTTGTTa [SEQ ID NO:233] |
| YB8 (chr 5) | | | Forward: Reverse F: Reverse E: | gtcaacagcctggtgtcatc [SEQ ID NO:234] AGCCACCGCTCCTTGTAAC [SEQ ID NO:235] actggcctcCTTGTAACTTTCc [SEQ ID NO:236] |
| Ya5 (chr 5) | 101 | 100 | Forward: Reverse F: Reverse E: | tttcttagttctttaacaacagatgc [SEQ ID NO:237] TATCCTTGCTAGAAGTTactgga [SEQ ID NO:238] attccaaaaAGAAGTTactggat [SEQ ID NO:239] |
| Ya5 (chr 5) | 101 | 101 | Forward: Reverse F: Reverse E: | aatacagccaaatgaactggaga [SEQ ID NO:240] TCTGGCCTCCATTTAGTatttt [SEQ ID NO:241] gcactctctATTTAGTattttctcg [SEQ ID NO:242] |
| | 163 | 168 | Forward: Reverse F: Reverse E: | aagtgtcaaggagaacaaaatgc [SEQ ID NO:243] GCCTCTGGCCTCCATTTA [SEQ ID NO:244] gctccaagagcactctctATTTAGTa [SEQ ID NO:245] |
| YB3A1 (chr 5) | 104 | 107 | Forward: Reverse F: Reverse E: | cccttttgtgtccctcttca [SEQ ID NO:246] ACCGCGCCTGGCCTAAAGT [SEQ ID NO:247] catgtatcccagaactTAAAGTAAAa [SEQ ID NO:248] |
| YA5 (chr 6) | 153 | 149 | Forward: Reverse F: Reverse E: | ttgccacttaggcaattaagg [SEQ ID NO:249] GCCTCGGCCTCCCACAAG [SEQ ID NO:250] ctctgtgcaCACAAGTTTTTCa [SEQ ID NO:251] |
| YA5 (chr 6) | | | Forward: Reverse F: Reverse E: | aaagggaagcccatcagact [SEQ ID NO:252] CCCGGCCGAAAATTCTTt [SEQ ID NO:253] ctgggttGAAAATTCTTttcttt [SEQ ID NO:254] |
| YB7 (chr 6) | 117 | 116 | Forward: Reverse F: Reverse E: | tgtccaggttaaacttcagttgc [SEQ ID NO:255] GCCCGGCCCGAAAGAAGT [SEQ ID NO:256] ggggcaatGAAAGAAGTTt [SEQ ID NO:257] |

FIG. 10H

| LOCUS | Filled | Empty | Primer Sequence | |
|---|---|---|---|---|
| YA5 (chr 10) | 150 | 156 | Forward:<br>Reverse F:<br>Reverse E: | ttagctgagggagtcactgga[SEQ ID NO: 258]<br>CCCGGCCGAAGATTTgtt[SEQ ID NO: 259]<br>gcatgtctcctgtGAAGATTTg[SEQ ID NO: 260] |
| YB7 (chr 10) | 125 | 130 | Forward:<br>Reverse F:<br>Reverse E: | tggccaacaaatacgtgaaa[SEQ ID NO: 261]<br>GCGCCCGGCCCTTAACTT[SEQ ID NO: 262]<br>cagcatctgttgttttCTTAACTTtt[SEQ ID NO: 263] |
| YC1 (chr 10) | 100 | 103 | Forward:<br>Reverse F:<br>Reverse E: | aggcaggcagatcacttg[SEQ ID NO: 264]<br>CGCGCCCCTAATTCTTTct[SEQ ID NO: 265]<br>ccatgcctggCTAATTCTTTc[SEQ ID NO: 266] |
| YC1 (chr 10) | 150 | 152 | Forward:<br>Reverse F:<br>Reverse E: | tgaaatggactgtggggact[SEQ ID NO: 267]<br>CGTGAGCCACCGATGAATA[SEQ ID NO: 268]<br>tggtatttggttacATGAATAAGGTCt[SEQ ID NO: 269] |
| YG6 (chr 10) | 162 | 163 | Forward:<br>Reverse F:<br>Reverse E: | ctcggcataaataaaactttaagga[SEQ ID NO: 270]<br>GCGCCCGGCCAATTCTAC[SEQ ID NO: 271]<br>ggcttgctcagAATTCTACCTTc[SEQ ID NO: 272] |
| YG6 (chr 10) | 100 | 105 | Forward:<br>Reverse F:<br>Reverse E: | gaacatccagcaccaaatcc[SEQ ID NO: 273]<br>CCCGGCCCTACCTTCtta[SEQ ID NO: 274]<br>cctggttgtgtgtTACCTTCtt[SEQ ID NO: 275] |
| YA5 (chr 11) | 162 | 165 | Forward:<br>Reverse F:<br>Reverse E: | ccttgacaggcactaaccact[SEQ ID NO: 276]<br>CTCCCAAAGTGCGGTTCTC[SEQ ID NO: 277]<br>gaatgtggagtacatGGTTCTCTTTa[SEQ ID NO: 278] |
| YA5 (chr 11) | 158 | 157 | Forward:<br>Reverse F:<br>Reverse E: | aggagaattgcttgaacctg[SEQ ID NO: 279]<br>TCCCAAGCTGAGATCCTTTC[SEQ ID NO: 280]<br>ggtatgctgagaTCCTTTCTc[SEQ ID NO: 281] |
| YA5 (chr 11) | 132 | 132 | Forward:<br>Reverse F:<br>Reverse E: | ggttttaccaggaatgtagtttgg[SEQ ID NO: 282]<br>GCCCGGCCTCATCCATTC[SEQ ID NO: 283]<br>gcctccctTCATCCATTCTTa[SEQ ID NO: 284] |
| YX (chr 11) | 117 | 118 | Forward:<br>Reverse F:<br>Reverse E: | ccagatggaagacatgcaca[SEQ ID NO: 285]<br>GCCCGGCCCATTCAGTCT[SEQ ID NO: 286]<br>ggagggttCATTCAGTCTTttg[SEQ ID NO: 287] |
| YB8 (chr 11) | 151 | 153 | Forward:<br>Reverse F:<br>Reverse E: | tcaaaaagactatctttccccatt[SEQ ID NO: 288]<br>TGGGACTGGGACTTAGGA[SEQ ID NO: 289]<br>aaagttatgggagTTAGGATTTCaa[SEQ ID NO: 290] |
| YC2 (chr 11) | | | Forward:<br>Reverse F:<br>Reverse E: | gcggaaaactaaaggcaaag[SEQ ID NO: 291]<br>CGCCCGGCCTTATTTTAG[SEQ ID NO: 292]<br>tgggttgatagttattTTATTTTAGtt[SEQ ID NO: 293] |

FIG. 10I

| LOCUS | Filled | Empty | Primer Sequence | |
|---|---|---|---|---|
| YA5 (chr 12) | | | Forward:<br>Reverse F:<br>Reverse E: | tgatccatgaacattcactctg [SEQ ID NO: 294]<br>GCCCGGCCCAGATCTTTC[SEQ ID NO: 295]<br>cagtgcactttCAGATCTTTCTtta[SEQ ID NO: 296] |
| YA5 (chr 13) | 101 | 104 | Forward:<br>Reverse F:<br>Reverse E: | gggattggatagaatgaagaaagg[SEQ ID NO: 297]<br>GCCCGGCCTCTCTCTTTag[SEQ ID NO: 298]<br>cgcgctctctcTCTCTCTTTag[SEQ ID NO: 299] |
| YA5 (chr 13) | | | Forward:<br>Reverse F:<br>Reverse E: | gggattggatagaatgaagaaagg[SEQ ID NO: 300]<br>GCCCGGCCTCTCTCTTTag[SEQ ID NO: 301]<br>cgcgctctctcTCTCTCTTTag[SEQ ID NO: 302] |
| YA5 (chr 13) | 120 | 126 | Forward:<br>Reverse F:<br>Reverse E: | acatggacacgcatgaaaga[SEQ ID NO: 303]<br>CCGGCCACAACCCTCATT[SEQ ID NO: 304]<br>ggtagttaccttacaACCCTCATTTTTa[SEQ ID NO: 305] |
| YA5 (chr 13) | 103 | 110 | Forward:<br>Reverse F:<br>Reverse E: | aagaagagtgaatgcacatttatga[SEQ ID NO: 306]<br>CCCGGCCCAGTTTCTTaat[SEQ ID NO: 307]<br>gggagtcatgaattCAGTTTCTTa[SEQ ID NO: 308] |
| YA1 (chr 15) | 160 | 158 | Forward:<br>Reverse F:<br>Reverse E: | cccaagtctaaaccaggaagaa[SEQ ID NO: 309]<br>CCCAGCTACCAGTTCCTCTTT[SEQ ID NO: 310]<br>atggtaccagcgCCTCTTTg[SEQ ID NO: 311] |
| YA5 (chr 15) | 132 | 133 | Forward:<br>Reverse F:<br>Reverse E: | tgtttttccttgccacactg[SEQ ID NO: 312]<br>GCGCCCGGCCTTACTCTC[SEQ ID NO: 313]<br>tcttcgtggtcTTACTCTCTCTTc[SEQ ID NO: 314] |
| Sp (chr 17) | 158 | 155 | Forward:<br>Reverse F:<br>Reverse E: | agctgccaataaggctgaaa[SEQ ID NO: 315]<br>CCGCACCTGGCTGATTGC[SEQ ID NO: 316]<br>gggccattTGATTGCAGtt[SEQ ID NO: 317] |
| Y (chr 17) | 156 | 162 | Forward:<br>Reverse F:<br>Reverse E: | cctagctactaggaagcctgag[SEQ ID NO: 318]<br>CGCCCGGCCAATTTACAG[SEQ ID NO: 319]<br>aagaactcattcagaAATTTACAGc[SEQ ID NO: 320] |
| Y (chr 19) | 105 | 105 | Forward:<br>Reverse F:<br>Reverse E: | tagagtgctgctgtggcaaa[SEQ ID NO: 321]<br>GCCCAGCCTAGTGTCCTCT[SEQ ID NO: 322]<br>tggttacCTAGTGGCCTCTct[SEQ ID NO: 323] |
| YA5 (chr 20) | 108 | 112 | Forward:<br>Reverse F:<br>Reverse E: | ccaagtcaggtataagcctcaga[SEQ ID NO: 324]<br>GCCGGATGTCCACTCttaaa[SEQ ID NO: 325]<br>acagaaaggatgtCCACTCtta[SEQ ID NO: 326] |
| YA5 (chr 20) | 157 | 161 | Forward:<br>Reverse F:<br>Reverse E: | tggcttccttttctttccta[SEQ ID NO: 327]<br>GCCCGGCCAAAATGACTG[SEQ ID NO: 328]<br>caagcagtgagaAAAATGACTGt[SEQ ID NO: 329] |
| YA5 (Y) | 204 | 208 | Forward:<br>Reverse F:<br>Reverse E: | tgctgttccagaaacacactt[SEQ ID NO: 330]<br>GCCCGGCCGACACTTCTT[SEQ ID NO: 331]<br>cacaatcaccttGACACTTTTTa[SEQ ID NO: 332] |

FIG. 10J

| LOCUS | Filled | Empty | Primer Sequence | |
|---|---|---|---|---|
| YB8 (Y) | 116 | 115 | Forward:<br>Reverse F:<br>Reverse E: | tgatggggatagaggaagaaga[SEQ ID NO: 333]<br>CGCCCGGCCTGTCTACCA[SEQ ID NO: 334]<br>gcatctctTGTCTACCAGTTTTaa[SEQ ID NO: 335] |
| YB8 (Y) | 159 | 162 | Forward:<br>Reverse F:<br>Reverse E: | cctaaggtgagtaaggttaaatcctg[SEQ ID NO: 336]<br>CGCCCGGCCTGGATTCTT[SEQ ID NO: 337]<br>tgttgtagctgtTGGATTCTTa[SEQ ID NO: 338] |
| SC (X) | 163 | 164 | Forward:<br>Reverse F:<br>Reverse E: | ccgaattcaaagaaggatca[SEQ ID NO: 339]<br>ACGCCCAGTCCTTAGGCTAC[SEQ ID NO: 340]<br>tgaccaacactCTTAAGCTACTTt[SEQ ID NO: 341] |
| SC (X) | 124 | 126 | Forward:<br>Reverse F:<br>Reverse E: | ctgtatcctcatgttctgttgga[SEQ ID NO: 342]<br>CTGCCCACTCATTTTCTTagg[SEQ ID NO: 343]<br>ccactcgttttctcTTTCTTag[SEQ ID NO: 344] |
| YA3A1 (X) | 158 | 157 | Forward:<br>Reverse F:<br>Reverse E: | acttgttgaccgagccacat[SEQ ID NO: 345]<br>GCCCGGCCAAGAAACTGG[SEQ ID NO: 346]<br>tccagttAAGAAACTGGTCCCttc[SEQ ID NO: 347] |
| YD8 (X) | 196 | 196 | Forward:<br>Reverse F:<br>Reverse E: | cagccagaagtggcttccta[SEQ ID NO: 348]<br>CCCGGCCGTCCTTTCATT[SEQ ID NO: 349]<br>gccccaatTCCTTTCATTtt[SEQ ID NO: 350] |
| YA4 (X) | 164 | 166 | Forward:<br>Reverse F:<br>Reverse E: | tgctggtcagatagaccctgt[SEQ ID NO: 351]<br>GCCCGGCCAACACTGCTT[SEQ ID NO: 352]<br>ggggtgaagtAACACTGCTTTt[SEQ ID NO: 353] |
| YG6 (X) | 162 | 162 | Forward:<br>Reverse F:<br>Reverse E: | gaatctagcccttcccttgc[SEQ ID NO: 354]<br>CCCGGCAGCCAAGAAGTC[SEQ ID NO: 355]<br>aaccagAGCCAAGAAGTCTTatg[SEQ ID NO: 356] |
| Y (X) | 159 | 162 | Forward:<br>Reverse F:<br>Reverse E: | tggtaaaaatggggtgacaaa[SEQ ID NO: 357]<br>CACCCGGCCTACAATTTTT[SEQ ID NO: 358]<br>gccacagatgatTACAATTTTTCaa[SEQ ID NO: 359] |
| SVA (Chr 1) | 160 | 161 | Forward:<br>Reverse F:<br>Reverse E: | ccagtgcctgtgtatctaagtga[SEQ ID NO: 360]<br>GAGAGGGAGAGGGAACTGAA[SEQ ID NO: 361]<br>tcaatggagtacaGAACTGAATCTTa[SEQ ID NO: 362] |
| SVA (Chr 1) | 212 | 116 | Forward:<br>Reverse F:<br>Reverse E: | gaaatgaataagcttcttggatagtg[SEQ ID NO: 363]<br>GGGAGAGGGAGAGGTCATTA[SEQ ID NO: 364]<br>cggccaatcTCATTATTTTCa[SEQ ID NO: 365] |
| SVA (Chr 3) | 102 | 110 | Forward:<br>Reverse F:<br>Reverse E: | aaagctgggtttcctttgc[SEQ ID NO: 366]<br>GGCTGGCCGGAAGTCTTa[SEQ ID NO: 367]<br>tggtgtcttgaaggataGAAGTCTTa[SEQ ID NO: 368] |
| SVA (Chr 19) | 171 | 174 | Forward:<br>Reverse F:<br>Reverse E: | cgtggtgatgtgcacttta[SEQ ID NO: 369]<br>TTAAATTTTTGACCGGGTTT[SEQ ID NO: 370]<br>gaaggaaaagtagttaaGGGTTTTTg[SEQ ID NO: 371] |

FIG. 10K

| LOCUS | Filled | Empty | Primer Sequence | |
|---|---|---|---|---|
| SVA (Chr 22) | 160 | 158 | Forward:<br>Reverse F:<br>Reverse E: | ccctgctatcctaaatgctg [SEQ ID NO: 372]<br>GTGATGGCGGGCTTAACCT[SEQ ID NO: 373]<br>cagcccaccCTTAACCTCTa[SEQ ID NO: 374] |
| LINE (Chr 2) | 152 | 154 | Forward:<br>Reverse F:<br>Reverse E: | tttcctcttgttcgtgatgg[SEQ ID NO: 375]<br>GGTGGTTCCAAGCTGTTTTC[SEQ ID NO: 376]<br>ccaaaaacccatAGCTGTTTTCTa[SEQ ID NO: 377] |
| LINE (Chr 2) | 176 | 172 | Forward:<br>Reverse F:<br>Reverse E: | tgggcatcactcagctctaa[SEQ ID NO: 378]<br>CTCCTCCTTCCGGCACTG[SEQ ID NO: 379]<br>acttctCGGCACTGGCTTt[SEQ ID NO: 380] |
| LINE (Chr 5) | 150 | 154 | Forward:<br>Reverse F:<br>Reverse E: | ttgctcagagcccataagga[SEQ ID NO: 381]<br>TGGCTCCTCCAAGCCTTC[SEQ ID NO: 382]<br>ctacacattaaattAAGCCTTCAAAtt[SEQ ID NO: 383] |
| LINE (Chr 6) | 156 | 153 | Forward:<br>Reverse F:<br>Reverse E: | tgaataccatgatatgccaaa[SEQ ID NO: 384]<br>TGATTGCCATTCACACTCC[SEQ ID NO: 385]<br>gaaattgcCACACTCCTTTTc[SEQ ID NO: 386] |
| LINE (Chr 7) | 167 | 166 | Forward:<br>Reverse F:<br>Reverse E: | agcagcatgatttataatcctttt[SEQ ID NO: 387]<br>GGTCCCCTAACAGGAGCAC[SEQ ID NO: 388]<br>tgtggagaaatatGAACACTTTTac[SEQ ID NO: 389] |
| LINE (Chr 8) | 150 | 151 | Forward:<br>Reverse F:<br>Reverse E: | taacatttgaccaaacagttgag[SEQ ID NO: 390]<br>CCCACTTTTTGACCTTTCa[SEQ ID NO: 391]<br>ccgctgcttctaACCTTTCa[SEQ ID NO: 392] |
| LINE (Chr 8) | 160 | 159 | Forward:<br>Reverse F:<br>Reverse E: | ttctcttcttccctctctgagc[SEQ ID NO: 393]<br>CTTGGCTCCTCCTGCAAAT[SEQ ID NO: 394]<br>tctctgctcatTGCAAATCTa[SEQ ID NO: 395] |
| LINE (Chr 8) | 133 | 134 | Forward:<br>Reverse F:<br>Reverse E: | ctctggagaagggtgcattg[SEQ ID NO: 396]<br>CGTCGCTCACGCTCTGTG[SEQ ID NO: 397]<br>ttagagagagagattTGTGAGTGtt[SEQ ID NO: 398] |
| LINE (Chr 10) | 150 | 148 | Forward:<br>Reverse F:<br>Reverse E: | tgctagtagaacccacgaggt[SEQ ID NO: 399]<br>GGCACAAGACAGGGATGC[SEQ ID NO: 400]<br>gaaaagacaaaGTTGCATTGTTa[SEQ ID NO: 401] |

FIG. 10L

| LOCUS | Filled | Empty | Primer Sequence | |
|---|---|---|---|---|
| Ya5 (Chr 1) | 129 | 124 | Forward: | Tcctaacaagggactttgcag [SEQ ID NO:402] |
| | | | Reverse F: | CGGCCTCCCAAAGAAGAT[SEQ ID NO:403] |
| | | | Reverse E: | gatgggaAAGATTCTCCACTTt[SEQ ID NO:404] |
| YA5 (chr 3) | 145 | 141 | Forward: | caggcctggtggtaacaaat[SEQ ID NO:405] |
| | | | Reverse F: | TCGGCCTCCCAATCAAC[SEQ ID NO:406] |
| | | | Reverse E: | ggccaatatTCAACATTCTTa[SEQ ID NO:407] |
| Ya5ACA1050 (chr 3) | 158 | 145 | Forward: | ccctggacttaccctatctca[SEQ ID NO:408] |
| | | | Reverse F: | TGCTGGGATTACATGGATTTT[SEQ ID NO:409] |
| | | | Reverse E: | ggagaatgtgtgTGGATTTTATTc[SEQ ID NO:410] |
| Ya5 (chr 3) | 153 | 155 | Forward: | aaaaacaagcaatggggaaa[SEQ ID NO:411] |
| | | | Reverse F: | GTGTCCGGCCACGTTTAAG[SEQ ID NO:412] |
| | | | Reverse E: | gttttaggtctaACGTTTAAGTCTTt[SEQ ID NO:413] |
| YB7 (chr 3) | 101 | 103 | Forward: | tgccaggaatggacttacaa[SEQ ID NO:414] |
| | | | Reverse F: | CCCGGCCATGAACTTCTaat[SEQ ID NO:415] |
| | | | Reverse E: | tgacctgcATGAACTTCTaataaaat[SEQ ID NO:416] |
| | | | Forward: | tgccaggaatggacttacaa[SEQ ID NO:414] |
| | | | Reverse F: | CCCGGCCATGAACTTCTaat[SEQ ID NO:415] |
| | | | Reverse E: | ttcatgacctgcATGAACTTCTa[SEQ ID NO:417] |
| YB7 (chr 3) | 101 | 107 | Forward: | ggtaatcaacagaagatcataagagga[SEQ ID NO:418] |
| | | | Reverse F: | gttAAGACTTGAGGCCGGG[SEQ ID NO:419] |
| | | | Reverse E: | cttctctcctccCTCAAGTCTTa[SEQ ID NO:420] |
| Yd8 (chr 4) | 118 | 125 | Forward: | caagtgctggggattacagg[SEQ ID NO:421] |
| | | | Reverse F: | AGACGGGGTTTCACCGTTAG[SEQ ID NO:422] |
| | | | Reverse E: | gcagagagacTAGGAGGCATtc[SEQ ID NO:423] |
| Y (chr 4) | 101 | 103 | Forward: | ccatggactcatggaatgct[SEQ ID NO:424] |
| | | | Reverse F: | AGCCTGCCACACTTCTTtag[SEQ ID NO:425] |
| | | | Reverse E: | ttccatgacggCACTTCTTt[SEQ ID NO:426] |
| YA8 (chr 4) | 107 | 114 | Forward: | tgtaggcaaaactttagtttcat[SEQ ID NO:427] |
| | | | Reverse F: | CCCGGCCCAGAAAGAACt[SEQ ID NO:428] |
| | | | Reverse E: | ctcccattatcttCAGAAAGAACt[SEQ ID NO:429] |
| YA5 (chr 4) | 102 | 101 | Forward: | ccattaaaggaacaagaatgga[SEQ ID NO:430] |
| | | | Reverse F: | GCCCGGCCAGTAATCTTTa[SEQ ID NO:431] |
| | | | Reverse E: | ctggtcCAGTAATCTTTaatacact[SEQ ID NO:432] |
| YA5 (chr 4) | 163 | 165 | Forward: | ctgagctggaggcataggtc[SEQ ID NO:433] |
| | | | Reverse F: | CCGGCCCGGCTATTTTTa[SEQ ID NO:434] |
| | | | Reverse E: | tgttgcccaGGCTATTTTTa[SEQ ID NO:435] |
| YA5 (chr 4) | 101 | 105 | Forward: | tggagagcattgacagttcat[SEQ ID NO:436] |
| | | | Reverse F: | CCGGCCCTGCTTCTTat[SEQ ID NO:437] |
| | | | Reverse E: | acacactcacCCTGCTTCTTa[SEQ ID NO:438] |

FIG. 10M

| LOCUS | Filled | Empty | Primer Sequence | |
|---|---|---|---|---|
| YI6 (chr 6) | 150 | 148 | Forward: | Aggtgctggcactgatgac [SEQ ID NO:439] |
| | | | Reverse F: | CTGGGATTACAAGCGTGAGG[SEQ ID NO:440] |
| | | | Reverse E: | tctcacaagtaagcaAGGTAGAt[SEQ ID NO:441] |
| YB8 (chr 6) | 153 | 153 | Forward: | ccttaagacctaagccctagtaga[SEQ ID NO:442] |
| | | | Reverse F: | CAGGCGTGAGCCACTAACTT[SEQ ID NO:443] |
| | | | Reverse E: | gtttcccaagccaCTAACTTTTa[SEQ ID NO:444] |
| Y (chr 7) | 133 | 125 | Forward: | gaatgcaagtaaaaaccatgagg[SEQ ID NO:445] |
| | | | Reverse F: | TTTAGTAGAGACGGGGTTAGCA[SEQ ID NO:446] |
| | | | Reverse E: | tccttgtgtctAGCATGTTTTg[SEQ ID NO:447] |
| Y (chr 7) | 150 | 148 | Forward: | aaccaaagtgactctgaagaagaaa[SEQ ID NO:448] |
| | | | Reverse F: | TCCTGGGTTCACGTATGATG[SEQ ID NO:449] |
| | | | Reverse E: | ttggaactggcTATGATGTTTg[SEQ ID NO:450] |
| YA5 (chr 7) | 157 | 159 | Forward: | ggttgatcatctgccgaaag[SEQ ID NO:451] |
| | | | Reverse F: | GCCACCGCGCCCTCTACT[SEQ ID NO:452] |
| | | | Reverse E: | caccttttaccacctTCTACTGTCTa[SEQ ID NO:453] |
| YA5 (chr 7) | 150 | 152 | Forward: | cttgagcccaggagtttgag[SEQ ID NO:454] |
| | | | Reverse F: | CGCCCGGCCTTATTTTTC[SEQ ID NO:455] |
| | | | Reverse E: | gagaggcccCCTTATTTTTCt[SEQ ID NO:456] |
| YA5 (chr 7) | 98 | 103 | Forward: | aacaaaattcccttcctcca[SEQ ID NO:457] |
| | | | Reverse F: | CGCCCGGCCAGAAGTTAG[SEQ ID NO:458] |
| | | | Reverse E: | ggatatatgctagCAGAAGTTAGATt[SEQ ID NO:459] |
| YB8 (chr 7) | 156 | 159 | Forward: | cctgaggtgtgtgcttaatcttc[SEQ ID NO:460] |
| | | | Reverse F: | CCCGGCCGCCAGTTTCTT[SEQ ID NO:461] |
| | | | Reverse E: | ttttcccagaaCCAGTTTCTTa[SEQ ID NO:462] |
| YA5 (chr 8) | 153 | 158 | Forward: | ctctcctgtgcccacttagg[SEQ ID NO:463] |
| | | | Reverse F: | ACGCCCGGCCATATTCTT[SEQ ID NO:464] |
| | | | Reverse E: | tggagtcatgtccatATATTCTTg[SEQ ID NO:465] |
| SG1 (chr 8) | 105 | 104 | Forward: | ttttcggttgtgaactgaagg[SEQ ID NO:466] |
| | | | Reverse F: | CGCCCAGCCTTAAACTGA[SEQ ID NO:467] |
| | | | Reverse E: | accagccccTAAACTGACCa[SEQ ID NO:468] |
| YA8 (chr 8) | 161 | 168 | Forward: | caggccatgtaagagtagaagga[SEQ ID NO:469] |
| | | | Reverse F: | GCCCGGCCAGAACACTAC[SEQ ID NO:470] |
| | | | Reverse E: | caaccctatgagattAGAACACTACa[SEQ ID NO:471] |
| Y (chr 10) | 122 | 126 | Forward: | cattgaatgaatggggaagaa[SEQ ID NO:472] |
| | | | Reverse F: | GCCTGGCGCAAAGATAtg[SEQ ID NO:473] |
| | | | Reverse E: | ttggaaccaaaGCAAAGATAtg[SEQ ID NO:474] |
| Y (chr 10) | 157 | 159 | Forward: | ggcaaagagtgaactagaatcca[SEQ ID NO:475] |
| | | | Reverse F: | GCGCCCGGCCTCAACTAC[SEQ ID NO:476] |
| | | | Reverse E: | ggaagagcacacTCAACTACTTTTa[SEQ ID NO:477] |

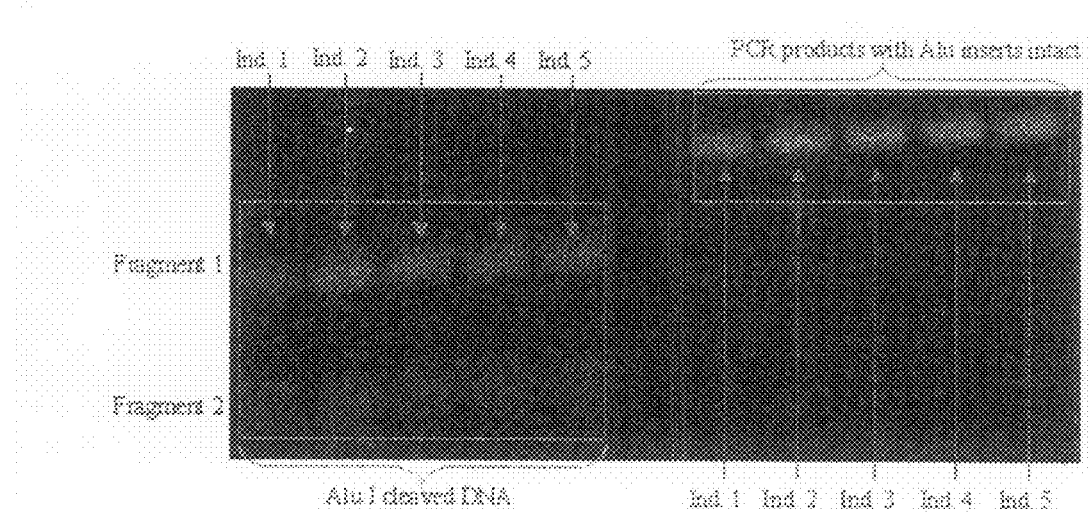

METHOD FOR GENETIC DETECTION USING INTERSPERSED GENETIC ELEMENTS

CLAIM OF PRIORITY

This application makes reference to, incorporates the same herein, and claims all benefits accruing under 35 U.S.C.§119 from an application earlier filed in the U.S. Patent & Trademark Office on 23 Feb. 2007 and there duly assigned Ser. No. 60/902,850.

BACKGROUND (a) Field of the Invention

The present invention relates to a method for genetic detection and a primer set for a polymorphic marker site. More particularly, the present invention relates to a primer set for a polymorphic marker site having a primer encompassing unique information, and to a method for genetic detection using the primer set.

(b) Description of the Related Art

Genomes ceased to be viewed as static entities when mobile interspersed genetic elements were first discovered in maize in the 1940's. Interspersed elements are DNA segments, which retain the ability to move their conserved sequence information from one genomic region to another via some enzyme-facilitated process. Since their discovery they have been found to reside ubiquitously throughout different genomes. They vary in frequency from one species to another and in most cases their function has remained questionable. Only recently has DNA sequencing technology shed light on the impact mobile genetic elements have on the genome in which they reside. The human genome project revealed a mobile element composition of approximately 45%.

There are several types of interspersed genetic elements in the human genome: Long INterspersed Elements (LINEs), Short INterspersed Elements (SINEs), SVA elements (other SINE, VNTR and Alu combination), and Human Endogenous Retroviruses (HERVs) to name a few. LINEs are a major retrotransposon group as they make up approximately 21% of the mass of the human genome. LINEs can be 4-6 kilobases in length and facilitate their own movement by producing mobilization enzymes. SINEs are elements approximately 300 base-pairs in length and produce no proteins with which to facilitate their movement. SINEs have, however, been extremely successful in the human genome, constituting more than 10% of the mass of the human genome.

Interspersed genetic elements have increased our understanding of the formation of human populations as well as non-human populations through the field of molecular evolution. Molecular evolution studies have identified human genetic diversity within and between continental populations. The fundamental basis for human identity testing is that genetic markers vary as to the presence/absence between individuals in the population. This is called polymorphism. Interspersed genetic elements are known for their contribution to human genetic variation because of their polymorphism. Recently, there have been large-scale, genome-wide studies geared to locating polymorphic elements. Because of these studies, advances have been made in the field of human population genetics. Geographic affiliation research now exists which utilizes these elements and is designed to identify the geographic origin of an unknown DNA sample. These polymorphic elements now have an entire public database devoted to their mapped chromosomal location.

There are several characteristics, which make interspersed genetic elements appealing to use as human identity testing markers and other genetic testing markers, and have an advantage over traditionally used Short Tandem Repeats (STRs). There is a distinct subfamily structure and this hierarchy is associated to how recently the Alu elements inserted into the genome. The "younger" elements are polymorphic in human populations. They are identical by descent markers: individuals that share an element do so because they share a common ancestor. They are stable inserts because once an element integrates there is no known excision mechanism with which to remove it from a genomic position. The possibility of another genetic element landing in the same genomic spot is essentially zero. Also, the ancestral state of an element is also known to be effectively the absence of that element. Currently used STRs are subject to mutation through the cells own DNA copying mechanisms and thus, can promote doubt in the mind of the tested participants.

Two previous publications (Novick et al., International Pediatrics 9: 60-68 (1994); Novick et al., Electrophoresis 16: 1596-1601 (1995)) utilizing Alu interspersed genetic elements for paternity and human identity testing was introduced, however, these studies were exclusive to using Alu elements because they were short enough in sequence, were not multiplex reactions, but single biological reactions, and used a different primer design methodology which will ultimately cause false results.

Interspersed genetic elements have the most potential to cause genomic deleterious effects because they are still actively mobilizing. They can cause insertion, recombination (swapping genetic material between sequences which are similar) mutations and transduce genetic material from one chromosomal location to another. Insertion mutation can occur when the element integrates into a promoter region, coding region or non-coding region. Alteration or complete halt of gene expression has been attributed to a few insertions. Homologous recombination events can occur between elements which are in close genomic proximity to one another. Non-homologous recombination between elements has also been shown. It has been suggested that insertion and recombination mutagenesis caused by Alu elements accounts for approximately 0.4% of human genetic diseases.

Creating multiplex PCR reactions using interspersed genetic elements up till now has been problematic due to several reasons. These elements encompass roughly 45% of the entire mass of the human genome. This essentially means that the same sequence from a particular type of element is found millions of times scattered randomly throughout all human chromosomes. Because of this homology (sequence similarity) there is difficulty in targeting a single polymorphic marker site (one that varies from individual to individual) because the polymorphic marker sites are the same sequence as the fixed (a marker site that does not vary between individuals). Another difficulty is getting uniqueness from a single polymorphic marker site.

The above information disclosed in this Background section is only for enhancement of understanding of the background of the invention and therefore it may contain information that does not form the prior art that is already known in this country to a person of ordinary skill in the art.

SUMMARY OF THE INVENTION

Accordingly, the present invention provides an improved primer set and an improved genetic testing method.

According to an aspect of the present invention, a method for genetic detection, including: carrying out a polymerase chain reaction (PCR) on a DNA sample with a primer set to produce amplified DNA products, the primer set comprising a first primer for a filled site containing an interspersed element and an empty site which does not contain the interspersed element, a second primer for the filled site, and a third primer for the empty site, the first primer complementary to a first flanking genomic sequence in the filled site and the empty site, the second primer complementary to a sequence comprised of a second flanking genomic sequence, a direct repeat sequence next to the second flanking genomic sequence and a part of the interspersed element next to the direct repeat sequence in the filled site, the third primer complementary to a sequence comprised of the direct repeat sequence and third flanking genomic sequences on both sides of the direct repeat sequence in the empty site; and analyzing the amplified DNA products.

According to an aspect of the present invention, the direct repeat sequence is not more than about 14 base pairs in length, the third flanking sequences include at least three bases on either side of the direct repeat sequence, and the third primer is less than or equal to about 20 base pairs in length.

According to an embodiment of the present invention, a method for genetic detection, including: carrying out a polymerase chain reaction (PCR) on a DNA sample with primer sets to produce amplified DNA products, the primer sets comprising: a primer set for a filled site which contains an interspersed element, the primer set for the filled site comprising a forward primer complementary to a first flanking genomic sequence and a reverse primer complementary to a sequence comprised of a second flanking genomic sequence, a direct repeat sequence positioned at the 5' position of the interspersed element and next to the second flanking genomic sequence, and a part of the 5' sequence of the interspersed element next to the direct repeat sequence; and a primer set for an empty site which does not contain the interspersed element, the primer set for the empty site comprising a forward primer complementary to a fourth flanking genomic sequence and a reverse primer complementary to a sequence comprised of the direct repeat sequence and third flanking genomic sequences on both sides of the direct repeat sequence in the empty site; and analyzing the amplified DNA products.

According to another aspect of the present invention, a primer set for a polymorphic marker site, including: a first primer for a filled site containing an interspersed element and an empty site which does not contain the interspersed element, the first primer complementary to a first flanking genomic sequence in the filled site and the empty site; a second primer for the filled site, the second primer complementary to a sequence having a second flanking genomic sequence, a direct repeat sequence next to the second flanking genomic sequence and a part of the interspersed element next to the direct repeat sequence; and a third primer for the empty site, the third primer complementary to a sequence having the direct repeat sequence and third flanking genomic sequences on both sides of the direct repeat sequence.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein:

FIG. 2 shows sequence interpretation of primer design for Alu insertion PCR assay;

FIG. 5 shows the alignment of the Yb8AC1197, and sequence interpretation of primer design for Alu insertion PCR assay according to an embodiment of the present invention;

FIG. 6 shows the alignment of the Yb8AC1197, and another sequence interpretation of primer design for Alu insertion PCR assay according to an embodiment of the present invention;

FIG. 9 shows a locus of Yb8NBC126 with the candidate genomic region;

FIGS. 10A to 10M show the lists of the examples of the primers according to embodiments of the present invention;

FIG. 11 shows an example of the restriction sites (underlined), which are contained within the Alu interspersed genetic elements, of Alu I restriction enzyme;

FIG. 12 shows the enzyme-digested products compared with the undigested PCR products in a gel electrophoresis.

DETAILED DESCRIPTION OF THE EMBODIMENTS

Figure 1:
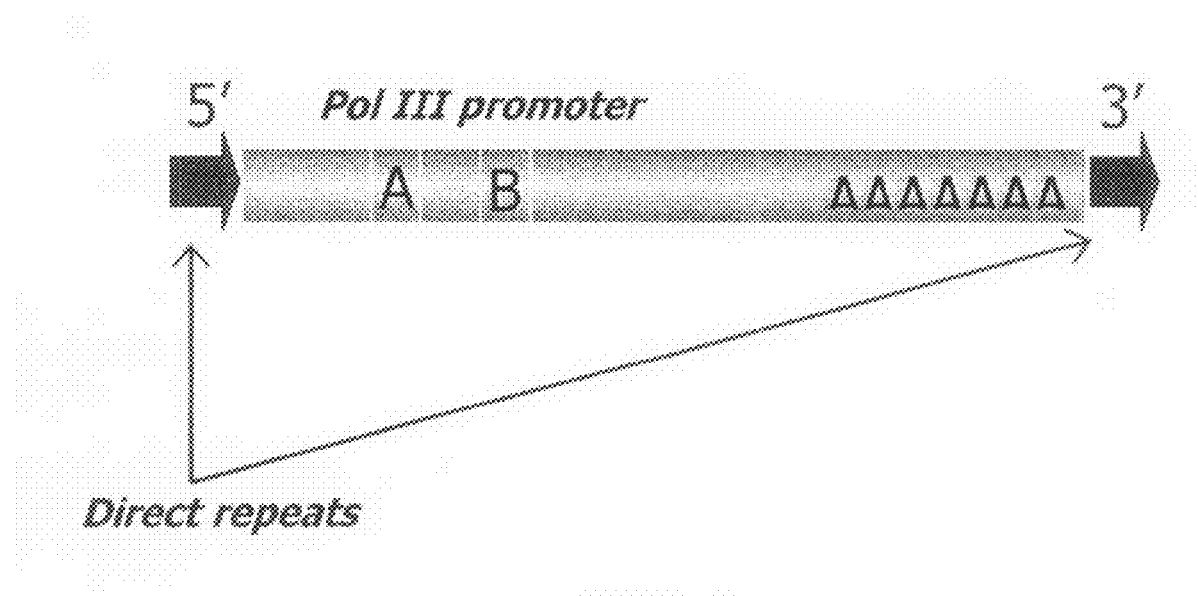
FIG. 1 shows an exemplary structure of the Alu interspersed genetic element.

According to an embodiment of the present invention, the uniqueness may be achieved by combining the interspersed genetic element sequence with the flanking genomic sequence, which results in a completely unique sequence. The way to design a "filled" (which contains an interspersed element) primer set to target a particular locus is to design one of the two primers such that it encompasses that unique information (e.g., interspersed element+flanking genomic sequence+direct repeat). The same holds true for an "empty" site in which at least one of the two primers can be designed such that the direct repeat sequence in addition to the flanking genomic sequence is included on both sides. In designing the "empty" site primer set, the primer designed around the direct repeat should not be too long, otherwise the primer will not be efficient because of its length and it will not have the same PCR specifications as the other primer sequence (e.g., "empty" site forward primer) it is working with. The primer designed around the direct repeat can be not more than approximately 20 base pairs in length. Therefore, it is important to target those interspersed genetic elements that have direct repeats of equal to or less than 14 base pairs in length. The "empty" site primer has the direct repeat sequence (of not more than 14 base pairs) plus 3 base pairs on either side of the element. Having only 3 base pairs of genomic sequence flanking the direct repeat is pushing the envelope on design uniqueness as one may experience non-specific binding of the primers to other homologous (genetically similar) genomic regions if there were any fewer bases added on the flanks.

This primer design according to embodiments of the present invention allows for the ability to test any type of interspersed genetic element containing characteristic direct repeat sequences (direct repeats). This gives the option of many new polymorphic marker sites because Alu elements are not the only interspersed genetic elements having direct repeats flanking their core sequence.

Design Methodology

Genetic variability between individuals is created by interspersed elements because interspersed elements are mobile and are inserted stably into chromosomal locations or locus. Some individuals may have insertions at a particular locus, while others lack an insertion at that locus. A "filled" site is a locus, which contains an inserted element. An "empty" site is a locus, which does not contain the element. Interspersed elements are inserted into the genome via an enzyme called L1 endonuclease, which makes a nick at a target genomic site. This endonuclease cuts the genomic target sites, and an element is inserted into the genome, subsequently forming characteristic direct repeating units (direct repeats), which are created at both ends just adjacent to the interspersed genetic element (Van Arsdell et al., Direct repeats flank three small nuclear RNA pseudogenes in the human genome, Cell. 1981 October; 26(1 Pt 1):11-7). This sequence is identical at both ends of the element and can span anywhere from 5-25 base pairs in length.

An example of the primer design for the Alu interspersed element is described hereinbelow, but the present invention is not limited thereto. The present invention can be applied to other interspersed elements as well as the Alu element with the same principle.

An exemplary structure of the Alu interspersed genetic element is given in FIG. 1. The element is about 300 base pairs long. There is a poly-adenine (poly-A) rich tail, which helps with incorporation of the element into the genome and A and B RNA polymerase promoter boxes that facilitate enzymatic copying of the element.

The direct repeats are produced upon insertion of the element at a particular chromosomal location or locus. These direct repeats give the Alu insertions their uniqueness. There are approximately 1 million copies of Alu in the human genome and they all differ by only a few base pair mutations within their core sequence so they are all very similar to each other. However, the flanking genomic sequence next to an individual Alu insertion is unique, which makes the direct repeat sequences in conjunction with the Alu sequence a uniquely identifiable genetic region.

These direct repeats are the basis for our unique primer design and make possible the amplification of multiple interspersed elements in one reaction (multiplex), which has been unobtainable until now.

If, in designing an interspersed genetic element multiplex primer sets for the "filled" and "empty" sites, the primer sets have the exact same forward and reverse primer sets, this design was insufficient and provided inconsistent results due to the following.

For example, as shown in FIG. 2, if the PCR amplification of the Yb8AC locus by using the same primers (for the filled site and the empty site, the "filled" and "empty" site amplicon fragments produced are 411 and 85 base pairs in length, respectively. In FIG. 2, the primers are in italic, and are the same sequences for both "filled" and "empty" sites. The "filled" locus contains an Alu interspersed genetic element (gray), direct repeat sequences (bold) flanking the Alu and flanking genomic sequences. The "empty" site reverse primer contains the direct repeat sequence in its natural state before the insertion of an Alu or other interspersed genetic element in addition to flanking genomic sequences on both sides. The entire amplified fragments from both "filled" and "empty" sites are underlined.

Figure 3A:
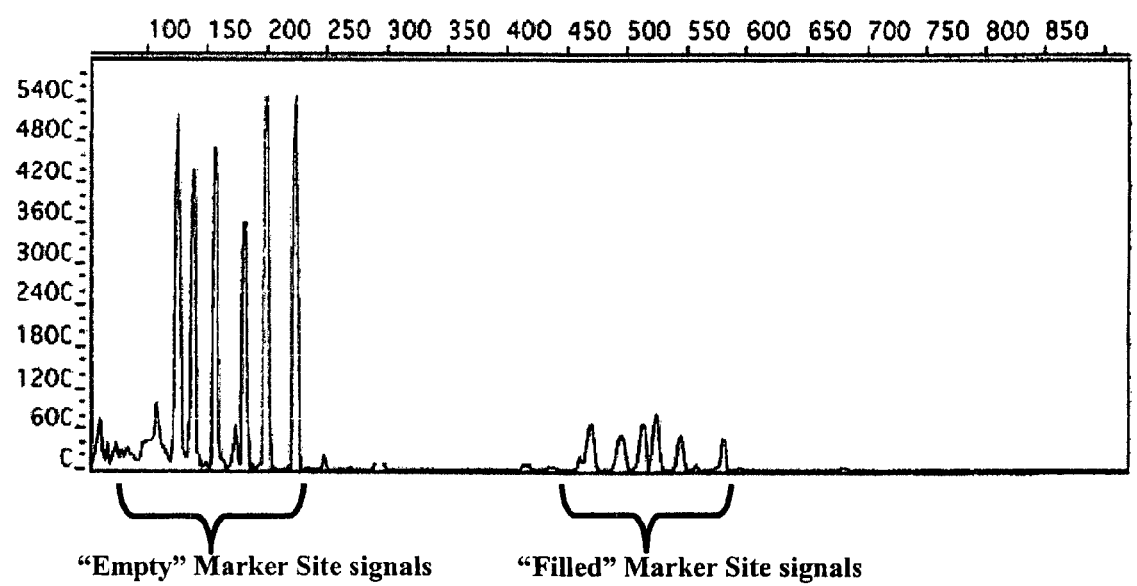
FIGS. 3A and 3B show examples of data from ABI 3100 DNA sequencer electropherogram using the primer design wherein the primer sets for the "filled" and "empty" sites have the exact same forward and reverse primer sets.
Figure 3B:
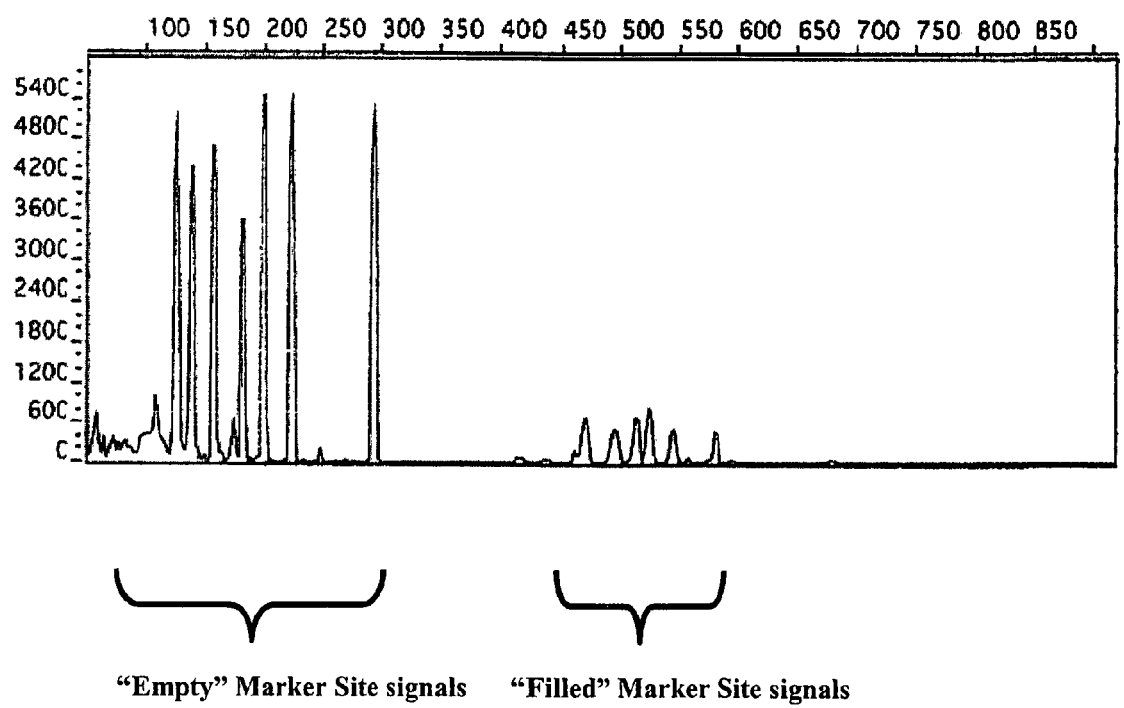

However, this strategy has been tried on individuals that have both sites present on their chromosomes and there exists too much competition between the "filled" and "empty" sites because the shortest fragment ("empty" site) has the advantage of being $\frac{1}{4}^{th}$ the length of the "filled" site fragment. Therefore, it is easier to amplify the "empty" site fragments in PCR. The result of this occurrence is noted in FIG. 3A and FIG. 3B. The heights of the peaks in FIG. 3A and FIG. 3B represent how well the fragments are amplifying in PCR. Note the large disparity in peak height between "filled" and "empty" site markers. PCR is an exponential process of increasing fragment sizes, so once the shorter fragments begin to increase in number during PCR cycles, it will overwhelmingly consume the chemical resources (e.g., dNTPs, $MgCl_2$, Taq Polymerase, etc.) that the "filled" site primers will also need thus causing the "dropping out" (or inability to amplify) of the "filled" site amplicon fragments. When this occurs, the individual who actually has an Alu on one chromosome would be interpreted as having no interspersed element at that marker site because the "filled" site could not compete with its shorter counterpart, the "empty" site.

Figure 4:
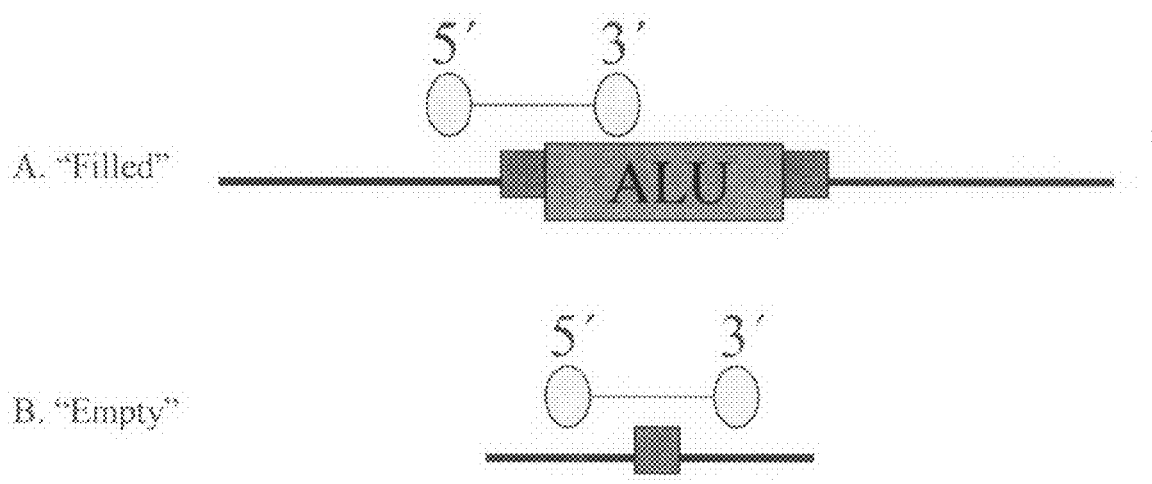
FIG. 4 shows fluorescently labeled probes designed to detect different sequences in an amplicon.

A second form of detection has to do with annealing fluorescently labeled probes to the amplicon fragments produced in PCR. These probes are designed to hybridize to a complementary sequence either during PCR or some other process through which the DNA fragments are separated into single strands exposing the complementary sequence amplified. FIG. 4 shows the process whereby a probe hybridizes to a specific locus. This detection technology is also based on the amplicon fragments produced during PCR, making PCR the key step in all fluorescent detection platforms. The same problem occurs with this technology as with fragment analysis using the ABI 3100 genetic analyzer, reason being difficulty in efficient amplification of the "filled" site amplicon when it is in direct competition with "empty" site amplification in the same reaction.

Therefore, if the primer sets for the "filled" and "empty" sites have the exact same forward and reverse primer sets, this design was insufficient and provided inconsistent results.

According to an embodiment of the present invention, when designing a primer set to target a marker, our novel design takes advantage of the direct repeat sequence at the 5' position (in front of or left side of the element, given a 5'-3' orientation of the DNA sequence) of the element. A DNA primer set is designed such that the "filled" and "empty" sites share the same forward primer, however, the reverse primer for the "filled" site, contains some of the 5' sequence of the interspersed element, the direct repeat sequence and the flanking genomic sequence. The reverse primer for the "empty" site encompasses the whole direct repeat sequence plus the flanking genomic sequence on both sides of the direct repeat, thus making this site completely unique. This design exploits the uniqueness of a single locus. This is difficult to do because all primer sets should create DNA fragments substantially the same length to avoid inter-PCR competition as well as all be amenable to the same PCR conditions. Also, the direct repeats are not more than about 14 base pairs in length for primer design, in order to create an "empty" site reverse primer because primers need to be less than or equal to about 20 base pairs in length for good PCR efficiency and there needs to be at least three bases of sequence on either side of the direct repeat sequence (in designing the primer) in order to increase the genomic specificity.

EXAMPLES

The following sections describe the methods used to design primer sets to target specific interspersed genetic elements, which are located on different chromosomal sites which are referred to as DNA marker sites. Polymorphic Alu interspersed genetic elements from two publications were used to create a triplex (Carter et al., Genomics 1: 167-178, 2004 and Otieno et al., Journal of Molecular Biology 342: 109-118, 2004, which are incorporated herein by reference).

Computational Analyses

Screening of the National Center for Biotechnology Information's (NCBI) Genbank non-redundant human genome database and the University of California Santa Cruz's human genome draft sequence was performed using a local installation of BLAST (Basic Local Alignment Search Tool), available at the website of NCBI to identify interspersed genetic elements in the human genome and extract their sequence as well as the flanking genomic sequence in order to design oligonucleotide primers (Altschul et al., J Mol Biol 215:403-410, 1990). A 700-1200 base pair fragment that included the Alu element and adjacent genomic DNA sequences were extracted from individual insertion sites and placed into the University of Washington Genome Center's RepeatMasker Web server to annotate repeat sequence content as described.

Primer Design

Oligonucleotide primers for the PCR amplification of each Alu element were designed using the 700-1200 base pair flanking unique sequence fragments and Primer3 software (Whitehead Institute of Biomedical Research, Cambridge, Mass., USA) and the oligonucleotide primers were synthesized and obtained from Operon (Alameda, Calif.). The program Reverse Complement was used from the Harvard Medical Technology Group and Lipper Center for Computational Genomics. The primers were subsequently screened against the GenBank nonredundant database to verify that they were unique DNA sequence.

Extraction and Quantitation of DNA

The DNA from anonymous donor samples was obtained from blood drawn in EDTA vacutainer tubes or buccal swabs and were extracted by ChargeSwitch® MP DNA extraction. The quantity of human DNA was determined by Quantifiler™ human DNA quantitation kit (Applied Biosystems) or Molecular Probes Pico Green DNA detection.

PCR and DNA Sequence Analysis

PCR amplification was performed in 25 µl reactions using 5 ng (total) of target DNA, 1 µL of each oligonucleotide primer (25 µM), 0.25 µL dNTP's (25 mM) in 2.5 µL of 10×PCR Buffer (AppliedBiosystems, Inc.), 2.5 µL of 25 mM $MgCl_2$ and 0.5 µL Taq DNA polymerase. Each sample was subjected to an initial denaturation step of 94° C. for 150 seconds, followed by 32 cycles of PCR at one minute of denaturation at 94° C., one minute at the 60° C. annealing temperature, one minute of extension at 72° C., followed by a final extension step at 72° C. for ten minutes and 4° C. to infinity. DNA fragment size analysis was performed using the Hitachi/Applied Biosystems 3100 DNA sequencer using the Sanger method of chain termination sequencing (Sanger et al. 1977).

Primer Design

The multiplex (multiple DNA markers in one reaction) in this study was designed from three Alu interspersed elements (Table 1) which had known population frequencies. In Table 1, "Locus" refers to name of the interspersed genetic marker site as given in the publications (Carter et al., Genomics 1: 167-178, 2004 and Otieno et al., Journal of Molecular Biology 342: 109-118, 2004, which are incorporated herein by reference), "FP" refers to forward primer, "RP Filled" refers to filled site reverse primer, and "RP Empty" refers to empty site reverse primer. "Size" refers to DNA fragment size produced by primers, and "Dye" refers to fluorescent tag placed on reverse primer for detection during DNA sequencing fragment analysis using ABI 3100 DNA sequencer. A screening of Alu polymorphic elements was performed to find a few candidates that would be the most amenable to PCR using the unique design methodology.

TABLE 1

| Locus | Target | Primer Sequence | Size | DYE |
|---|---|---|---|---|
| Yb8AC1197 | FP | TGCTGCCCTTAATCTTTACCA (SEQ ID Nk: 3) | | |
| | RP Filled | CCCGGCCTTCATTTCTAAG* (SEQ ID NO: 4) | 105 | FAM |
| | RP Empty | GAGACTTTCATTTCTAAGATGTCTGG* (SEQ ID NO: 5) | 104 | JOE |
| Yb8AC1439 | FP | TGCTGAGCTCCATGCTATTC (SEQ ID NO: 6) | | |
| | RP Filled | AGACGGGGTACCAGCTCTTG* (SEQ ID NO: 7) | 159 | FAM |
| | RP Empty | GCTCACCAGCTCTTGACGTA* (SEQ ID NO: 8) | 154 | JOE |
| Yb8NBC126 | FP | AGCTCCTGGAAAAGGGAAAG (SEQ ID NO: 9) | | |
| | RP Filled | ATCCGATTGGGGCACCTTA* (SEQ ID NO: 10) | 177 | FAM |
| | RP Empty | ATGATGATTGGGGCACCTTA* (SEQ ID NO: 11) | 178 | JOE |

FIG. 5 shows the alignment of the Yb8AC1197. The primers are in italic. The forward primer is the same sequence for both "filled" and "empty" sites. The "filled" marker site reverse primer contains some Alu interspersed genetic element (gray), the direct repeat sequence (bold) and the flanking genomic sequence in the reverse primer. The "empty" site reverse primer contains the direct repeat sequence in addition to the flanking genomic sequence on either side. The entire amplified fragments from both "filled" and "empty" sites are underlined. This locus is approximately 100 base pairs for both "filled" and "empty" sites. FIG. 6 shows an alternative primer set. Both sites produce amplicon sizes that are approximately 65 base pairs in length.

Figure 7:
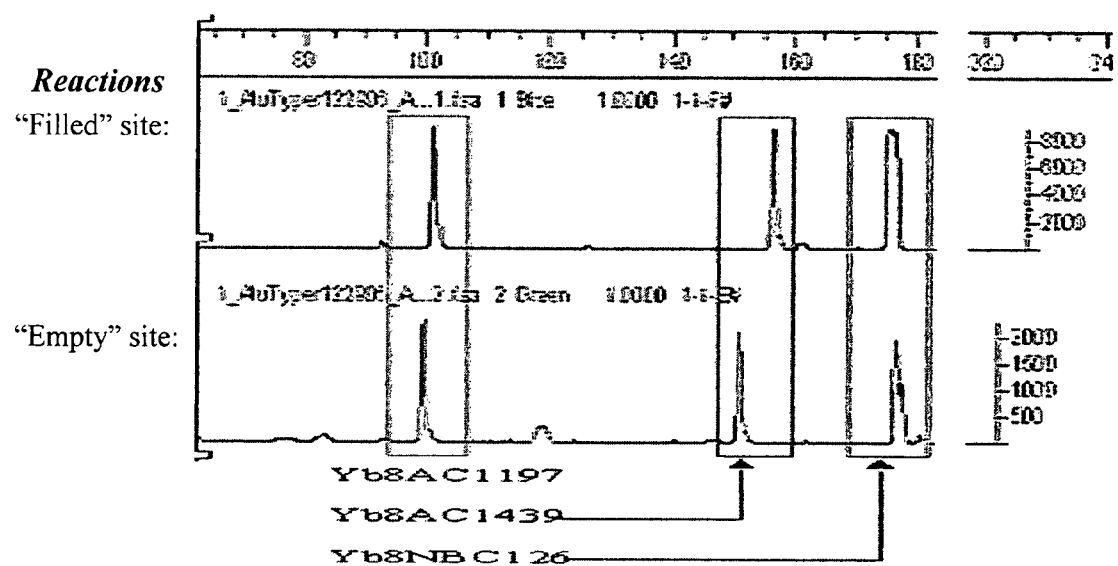
FIG. 7 shows electropherogram of the triplex (3-marker multiplex) performed on an individual DNA sample according to an embodiment of the present invention.

FIG. 7 shows electropherogram of the triplex (3-marker multiplex) performed on an individual DNA sample. The "filled" marker site reaction contains the forward primer and the reverse primer "filled" (see Table 1: RP Filled) to detect whether or not the tested individual contains an Alu interspersed element for the individual marker sites. The empty site reaction detects the absence of the Alu marker at the marker site. All "filled" and "empty" site reactions are held separately. In all three markers, a clear result was ascertained, for both "filled" and "empty" site reactions. Peaks in both reactions, at the same marker site denote that on one chromosome there is an Alu and the other chromosome is absent for an insertion so the individual.

There is no significant disparity of amplification in a single reaction, thus solving the problem of preferential amplification as shown in FIGS. 3A and 3B.

Figure 8:
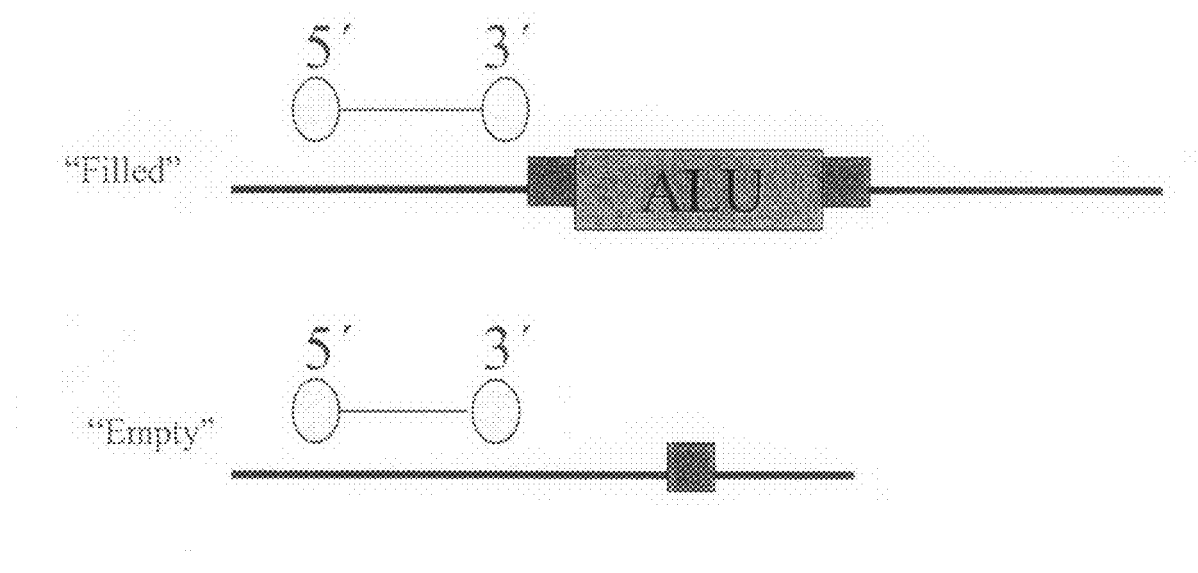
FIG. 8 shows fluorescently labeled probes designed to detect different sequences in an amplicon according to an embodiment of the present invention.

Using the primer design as described above, amplified PCR product was produced and detected using hybridization probes which contain target site complementary genomic sequence. Attached to the probes are fluorescent molecules which give off fluorescence when the probe has annealed directly to the target PCR product. The probe sequence is locus specific, however "filled" and "empty" site reactions are performed independently with the same probe being used for both reactions. Amplification specificity lies within the primer design. FIG. 8 illustrates the concept behind the hybridization probes in conjunction with PCR amplification.

A hybridization probe which has complementary sequence common to both "filled" and "empty" site products can be used. FIG. 9 shows a locus of Yb8NBC126 with the candidate genomic region (underlined) amplified between forward and reverse primers (in italic), which was used to design the hybridization probes. The complementary sequence that is within the probe is common to both "filled" and "empty" site PCR amplicons. The forward and reverse primer sets for each site amplification are in italic. Bold letters denote direct repeat sequence which is contained within one of the primers (i.e., the reverse primer) and gray letters, in "filled" site reactions only, denote the Alu insertion.

The examples of the primers according to embodiments of the present invention are listed in FIGS. 10A to 10M, wherein "Locus" refers to name of the interspersed genetic element marker site, "Filled" and "Empty" refer to the amplicon sizes of the filled site and the empty site, respectively, "FORWARD" refers to forward primer, "Reverse F" refers to filled site reverse primer, and "Reverse E" refers to empty site reverse primer.

System Detection Platforms

It may be possible that the genetic testing system according to an embodiment of the present invention may be applied on various detection platforms including the Applied Biosystems 3100 series of DNA sequencers, Luminex system, Biomodular Multi-Scale systems, and the Hitachi FMBIO® laser detection system.

In interspersed genetic element scientific literature, there are few hybridization techniques that have been employed for the purpose of detection. One type of technique is the dot blot hybridization, which has been used only for academic research and mainly involves the analysis of element characteristics, transcriptional and mobility dynamics. Further research involved, which is a pertinent subject here, concerned human population structure and genetic variability between individuals which could ultimately be used for human identification purposes. Dot blot detection involves isolating high molecular weight genomic DNA, denaturing the DNA and then dot blotting onto a nylon membrane. Baking, prehybridization, hybridization and washes are also performed, making this a very labor-intensive form of detection. Another form of probe hybridization applied to interspersed genetic element detection (namely Alu) was FISH (Fluorescence IN-SITU Hybridization). It is a relatively new technology utilizing fluorescently labeled DNA probes to detect or confirm gene or chromosome abnormalities that are generally beyond the resolution of routine Cytogenetics. Since interspersed genetic elements are found scattered throughout all chromosomes and are very similar in sequence, they are good candidates for comprehensive chromosomal structure analysis (Arcot et al. 1998). Another method of hybridization probe detection that has been seen again, for Alu, is the use of padlock probes. Padlock probes, are circularizing oligonucleotide probes having properties that should prove valuable in a wide range of genetic investigations, including in situ analyses, genotyping and measurement of gene expression. However, padlock probes can be difficult to obtain by standard oligonucleotide synthesis because they are relatively long and require intact 5'- and 3'-end sequences to function.

Particularly, the LUMINEX system is based on laboratory multianalyte profiling (LabMAP™) technology that uses up to 100 color-coded bead sets, each of which can be conjugated with a different specific reactant. Thus, up to 100 different species can be simultaneously measured in a single tube or microplate well. LUMINEX assays involve the interaction of immobilized "bead-bound" capture molecules with a reaction partner (analyte) in solution. A reporter molecule, specific for the analyte, is used to quantify the interaction. The constituents of each well are drawn up into the flow-based LUMINEX array reader where each reaction (bead set) is identified by its spectral signature after excitation by the red classification laser. The attendant reporter signal from each reaction is simultaneously quantified by fluorescence generated by the green reporter laser. The software provides automated data analysis and the generation of detailed summary reports. This level of sophistication in hybridization probe detection of interspersed genetic elements has never before been published.

Also, in order to eliminate or reduce the problem of differential amplification of filled and empty ALU insertion location for detection, capillary electrophoresis of fluorescently labeled products can be used. The amplified products may be analyzed by using a gene chip which may be also referred to as micro array.

Utilization of a Restriction Enzyme Before or After PCR

Cleaving the genetic material with a restriction enzyme, either pre or post PCR, is useful in reducing the possibility of cross-reactivity products being generated, which can result in a false positive signal and also in eliminating intra-locus competition between "filled" and "empty" sites. False results are caused by primer cross-reactivity of "empty site" primer sets creating an amplified "filled site" product due to similarity (homology) between the "empty" and "filled" site primer sequences. This restriction enzyme is specific for sequences within the interspersed genetic element and is applied before a detection platform is used to analyze the PCR amplified product. FIG. 11 shows an example of the restriction sites (underlined) of Alu I restriction enzyme that are contained within the Alu interspersed genetic elements of SpACchr2. The Alu I restriction enzyme recognizes the AGCT site and cuts between the G and C leaving a product with blunt ends (as opposed to overhanging or protruding ends). This element is 315 base pairs long with characteristic direct repeats (bold) flanking the 5' and 3' sides of the element. The flanking unique genomic sequence is found in lowercase letters. Utilization of the ALU I restriction endonuclease in FIG. 11 results in the cleaving of the Alu element into three separate fragments that are 174, 60, and 79 base pairs in length.

This restriction enzyme would be used in "empty" site reactions to eliminate the possibility of the "empty" site primers amplifying a "filled" site product, subsequently producing a false positive for the empty site.

Cross-reactivity is typically low-level and the ALU I enzyme can reduce the false positive signal by recognizing an amplified PCR product that contains an Alu and cutting it into smaller fragments.

This enzyme digestion of the amplified post PCR product will contribute to increased accuracy of results, especially when using molecular probes such as the LUMINEX probe based detection system, which uses biotin-tagged probes.

The oligonucleotide primer sets used to amplify individual genomic locations (loci) that were designed for this genetic system, are similar in sequence to a certain degree, depending on the individual locus. This sequence homology could potentially cause some low-level cross-reactivity. To reduce any potential low-level cross-reactivity to below instrumentation detection thresholds, the enzyme is used to chop the Alu filled amplicon in the "empty" site reaction. FIG. 12 shows the enzyme-digested products in a gel electrophoresis. DNA samples from five individuals were PCR amplified with a single Alu element marker. Half of the sample was digested after PCR amplification (left side of the illustration) with ALU I and the other half of the sample was not digested (right side of the illustration). The enzyme-digested products show three, smaller fragments being produced compared to the undigested PCR products of the same individuals.

This chopping up of the PCR amplified DNA product will lead to a cleaner result, particularly when a molecular probe-based method of detection is used.

Applications

The applications of the primer design according to an embodiment of the present invention include, but are not limited to, genetic disease testing as well as human identity testing. In addition, the amplified products can be used for identification of cell lines, bacterial strains, to identify plants, seeds and genetically modified products, to detect agents of Bio-terrorism, to identify ethnic affiliation of individuals, identification of old degraded bones and other human remains due to the ability of the method to generate small amplicons from degraded DNA.

FBI Missing Persons Database

Forensic cases often involve victim remains found in areas where decomposition can easily take place. In such situations, the DNA evidence can become quickly degraded. Often most, if not all, soft tissue has been eliminated and hard tissue, like bones/teeth, are all that's left of the victim. Bones and teeth are harder to obtain full DNA profiles. Currently used DNA testing kits use Short Tandem Repeats (STRs), which have markers that range from 100-450 base pairs in length. STR kits are not ideal for getting genetic profiles from hard tissue. Also, there are activated enzymes called DNA nucleases with the aim of destroying the cell's DNA template in the nucleus. These enzymes cut the DNA into fragments of 200 base pairs and smaller, so half of the range that STRs would be useful is ruled out, thus preventing the acquisition of a full genetic profile. Given that a number of STR marker variations are very common in human populations, if one were only to acquire half a genetic profile from a suspect, there is a higher chance that a random individual would match the evidence sample, leading to a mistake in identity. Furthermore, DNA can degrade into fragments smaller than 200 base pairs over time due to other environmental perturbations such as heat, pH changes, UV light, etc. The interspersed genetic elements can be designed such that the fragment size of all markers is not more than 100 base pairs, which greatly increases the chances of acquiring a full genetic profile and make this system useful for extracting full profiles from hard tissue such as bone/teeth.

Paternity Tests

Paternity testing largely entails using DNA extracted from buccal swabs (cotton swabs) and applying STR markers to obtain a genetic profile. DNA from cells collected with a buccal swab are subject to degradation through environmental and bacterial insults like forensic evidence samples, thus decreasing the chances of acquiring a full DNA profile from one or more of the tested participants (a duo or trio). Again, STR markers range from 100-400 base pairs and if degradation takes place typically at 200 base pairs, half of the profile range for STRs is eliminated. A system that is approximately 100 base pairs is ideal for this situation. Also, there are situations where the STR variations in tested participants are too common in the population and therefore the probability of paternity can fall below the state or company requirements. These cases require more testing, the use of more markers and the cost of more time. In some cases, there is no other way to bring the probability up because all STR markers have been exhausted. The paternity testing field could use another marker system such as the interspersed genetic element system in order to rectify these issues where STR markers are exhausted.

Nuclear DNA Detection in Hair Samples Using Alu Elements

Nuclear DNA is the most discriminating DNA that is contained within our cells. Detection of nuclear DNA for the purposes of human identity testing using hair, the most common crime scene evidence sample, is a method research teams and companies in the field of development have been trying to accomplish for some time due to its great importance. DNA extraction of crime scene hair samples involves retrieving maternally inherited mitochondrial DNA that lies within cells in many copies. Although mitochondrial DNA is more accessible in hair, the variation of the genetic markers is less, so it ceases to be as effective a discriminating tool as nuclear DNA. Shed or cut hair is particularly problematic in retrieving DNA because the hair has no root. The root itself has skin cells at the base and these skin cells can be used to increase the chances of ascertaining a DNA profile. Our data presented here pushes the envelope on genetic detection by using shed/cut hair.

Figure 13:
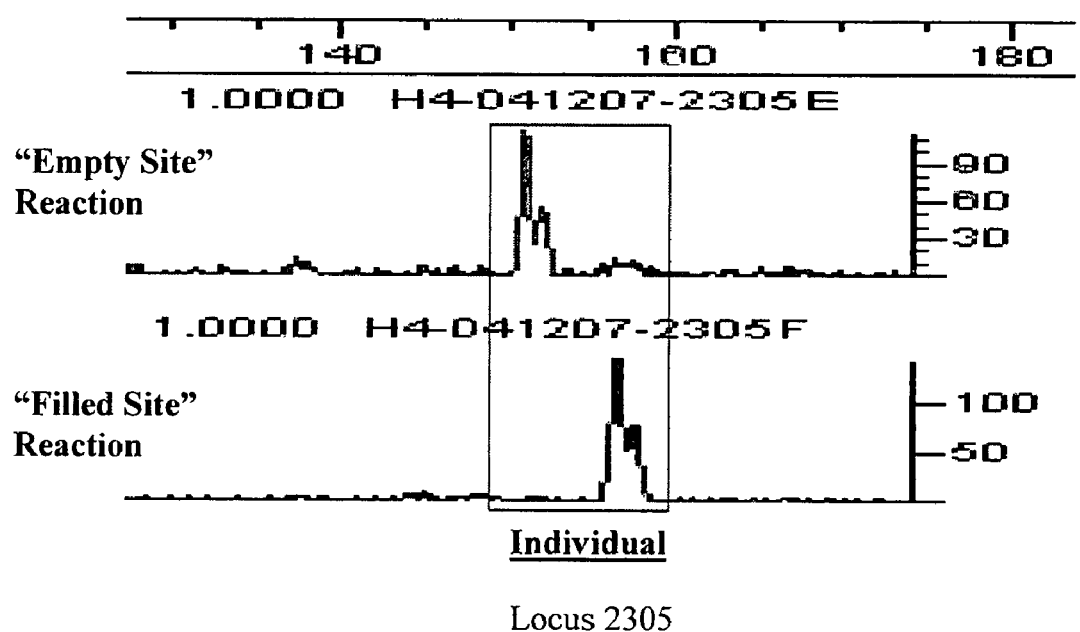
FIG. 13 shows empirical evidence using fluorescently labeled oligonucleotide primers targeted to amplify a polymorphic interspersed genetic element in a single locus reaction.

To our knowledge, hard evidence of proof of this concept has not been publicly published. We demonstrate here our empirical evidence using fluorescently labeled oligonucleotide primers targeted to amplify a polymorphic interspersed genetic element in a single locus reaction (FIG. 13).

The DNA template was extracted from 4 centimeter long shed/cut hair samples. Genetic detection took place on an Applied Biosystems 3100 genetic analyzer. The sample was a 4-centimeter hair sample that had been cut (contained no root) from the tested participant. The peak in the first row represents amplification of the "empty" site reaction. This 3100 data has been compared with a reference sample consisting of buccal cells (epithelial cheek cells). The data show that this individual was absent of an Alu element at least one of the two chromosomes. The peak in the second row represents amplification of the "filled" site reaction, which is evidence that this individual contains an Alu element at that locus for at least one of the two chromosomes. The data shows that this person contains one Alu element inserted on one of the two chromosomes. This person is considered to be a heterozygote for the locus 2305. That is, there was a peak produced for the "filled" site and "empty" site reactions. This equates to there being only one Alu element present on one of the two chromosomes that contain this locus.

While this invention has been particularly shown and described with reference to embodiments thereof, it will be understood by those skilled in the art that various changes in form and details may be made therein without departing from the spirit and scope of the invention as defined by the appended claims.

What is claimed is:

1. A method for genetic detection, comprising:
carrying out a polymerase chain reaction (PCR) on a DNA sample with a primer set to produce amplified DNA products, the primer set comprising a first primer for both a filled site containing an interspersed element and an empty site which does not contain the interspersed element, a second primer for the filled site, and a third primer for the empty site, the first primer complementary to a first flanking genomic sequence in the filled site and the empty site, the second primer complementary to a sequence comprised of a second flanking genomic sequence, a direct repeat sequence next to the second flanking genomic sequence and a part of the interspersed element next to the direct repeat sequence in the filled site, the third primer complementary to a sequence comprised of the direct repeat sequence and third flanking genomic sequences on both sides of the direct repeat sequence in the empty site; and
analyzing the amplified DNA products to detect presence or absence of the interspersed element insertion at the site.

2. The method of claim 1, wherein the direct repeat sequence is not more than about 14 base pairs in length, the third flanking sequences include at least three bases on either side of the direct repeat sequence, and the third primer is less than or equal to about 20 base pairs in length.

3. The method of claim 1, wherein the first primer is a forward primer for the filled site and the empty site, the second primer is a reverse primer for the filled site, and the third primer is a reverse primer for the empty site.

4. The method of claim 1, wherein, in the filled site, the first flanking genomic sequence is in front of the second flanking genomic sequence, the direct repeat is present on the 5' flanking side of the interspersed element and the part of the interspersed element included in the sequence complementary to the second primer is part of the 5' sequence of the interspersed element.

5. The method of claim 1, wherein the amplified DNA products from the filled site and the empty site have substantially the same length.

6. The method of claim 1, wherein the interspersed element is selected from the group consisting of an Alu sequence, a long interspersed element (LINE), a short interspersed element (SINE), a human endogenous retrovirus (HERV), and a combination thereof.

7. The method of claim 6, wherein the interspersed element is an Alu sequence.

8. The method of claim 1, wherein the interspersed element is 50 to 200 base pairs in length.

9. The method of claim 1, wherein the analysis of the amplified DNA products comprises sequencing the amplified DNA products.

10. The method of claim 1, wherein the analysis of the amplified DNA products comprises quantitating the filled site and the empty site.

11. The method of claim 1, wherein the analysis of the amplified DNA products is one selected from the group consisting of identifying paternity in human or animal, identifying a plant, a seed or a genetically modified product, detecting an agent of bio-terrorism, and identifying ethnic affiliation of an individual.

12. The method of claim 1, wherein the analysis of the amplified DNA products comprises using at least one of a real-time PCR system, a DNA sequencer, a laser detection system, a detection platform, a gene chip, or capillary electrophoresis of the amplified DNA products which are fluorescently labeled.

13. The method of claim 1, wherein the analysis of the amplified DNA products comprises using fluorescently labeled hybridization probes.

14. The method of claim 1, wherein the analysis of the amplified DNA products comprises using an identical hybridization probe for the filled site and the empty site to hybridize to a homologous region in front of the interspersed element in view of a 5' to 3' orientation of the DNA sequence.

15. The method of claim 1, further comprising, before or after the polymerase chain reaction, cleaving a genetic material in the DNA sample with a restriction enzyme specific for sequences within the interspersed element.

16. The method of claim 15, wherein the restriction enzyme is ALU I.

17. The method of claim 1, wherein the polymerase chain reaction is a multiplex polymerase chain reaction with multiple primer sets.

18. The method of claim 1, wherein the interspersed element is Yb8AC1197, and the primer set comprises the first primer containing the sequence of TGCTGCCCTTAATCTT-TACCA (SEQ ID NO: 3), the filled site second primer containing the sequence of CCCGGCCTTCATTTCTAAG (SEQ ID NO: 4), and the empty site third primer containing the sequence of GAGACTTTCATTTCTAAGATGTCTGG (SEQ ID NO: 5).

19. The method of claim 1, wherein the interspersed element is Yb8AC1439, and the primer set comprises the first primer containing the sequence of TGCTGAGCTCCATGC-TATTC (SEQ ID NO: 6), the filled site second primer containing the sequence of AGACGGGGTACCAGCTCTTG (SEQ ID NO: 7), and the empty site third primer containing the sequence of GCTCACCAGCTCTTGACGTA (SEQ ID NO: 8).

20. The method of claim 1, wherein the interspersed element is Yb8NBC126, and the primer set comprises the first primer containing one of the sequence of AGCTCCTG-GAAAAGGGAAAG (SEQ ID NO: 9) and the sequence of CTGTGAAGGCTCACCTGGAG (SEQ ID NO: 42), the filled site second primer containing the sequence of ATCCGATTGGGGCACCTTA (SEQ ID NO: 10), and the empty site third primer containing the sequence of ATGATGATTGGGGCACCTTA (SEQ ID NO: 11).

21. The method of claim 1, wherein the interspersed element is Yb8AC1197, and the primer set comprises the first primer containing the sequence of CCTCCCTACAGAA (SEQ ID NO: 479), the filled site second primer containing the sequence of CGCCCGGCCTTCATTTCT (SEQ ID NO: 480), and the empty site third primer containing the sequence of GAGACTTTCATTTCTAAGATG (SEQ ID NO: 481).

22. The method of claim 17, wherein the interspersed element comprises Yb8AC1197, Yb8AC1439, and Yb8NBC126, and the primer sets comprise:

a primer set for Yb8AC1197 comprising a first primer containing the sequence of TGCTGCCCTTAATCTT-TACCA (SEQ ID NO: 3), a filled site second primer containing the sequence of CCCGGCCTTCATTTCTAAG (SEQ ID NO: 4), and an empty site third primer containing the sequence of GAGACTTTCATTTCTAAGATGTCTGG (SEQ ID NO: 5);

a primer set for Yb8AC1439 comprising a first primer containing the sequence of TGCTGAGCTCCATGC-TATTC (SEQ ID NO: 6), a filled site second primer containing the sequence of AGACGGGGTACCAGCTCTTG (SEQ ID NO: 7), and an empty site third primer containing the sequence of GCTCACCAGCTCTTGACGTA (SEQ ID NO: 8); and a primer set for Yb8NBC126 comprising a first primer containing the sequence of AGCTCCTGGAAAAGG-GAAAG (SEQ ID NO: 9), a filled site second primer containing the sequence of ATCCGATTGGGGCAC-CTTA (SEQ ID NO: 10), and an empty site third primer containing the sequence of ATGATGATTGGGGCAC-CTTA (SEQ ID NO: 11).

23. The method of claim 1, wherein a set of the interspersed element, the first primer, the second primer, and the third primer are one of a set as shown in the below table:

| Interspersed Element | Primer Sequence | |
|---|---|---|
| Yb8NBC67 | First primer | TGTGTCAAAGAGCGAGATGAACA (SEQ ID NO: 18) |
| | Second primer | GGGTTCACGCCATTCTAGC (SEQ ID NO: 19) |
| | Third primer | TTCATAGCAGCCTATTCTAGCAG (SEQ ID NO: 20) |
| Ya5NBC241 | First primer | aaacataatttagttccccacaa (SEQ ID NO: 21) |
| | Second primer | cccggccaagatccattc (SEQ ID NO: 22) |
| | Third primer | cccccagaagaaccattct (SEQ ID NO: 23) |
| Yb8NBC237 | First primer | GCCACTCGTAGGCAGTCATT (SEQ ID NO: 24) |
| | Second primer | GCCCGGCCGTTACGGTTT (SEQ ID NO: 25) |
| | Third primer | AGCATGTCAACTGTTACGTATG (SEQ ID NO: 26) |
| YC1NBC60 | First primer | CATAGCACCAGGTGACCACA (SEQ ID NO: 27) |
| | Second primer | GCGCCCGGCCTCTTTCTT (SEQ ID NO: 28) |
| | Third primer | AAAGGTTAAACCATCTTCTTTCTACA (SEQ ID NO: 29) |
| | First primer | GCACTTCACACCATTTCTGC (SEQ ID NO: 30) |
| | Second primer | GCGCCCGGCCTCTTTCTT (SEQ ID NO: 31) |
| | Third primer | AAAGGTTAAACCATCTTCTTTCTACA (SEQ ID NO: 32) |
| Ya5AC2305 | First primer | AGGACAGGTTAATAATCCAGAAAAA (SEQ ID NO: 33) |

-continued

| Interspersed Element | Primer | Sequence |
|---|---|---|
| | Second primer | CGGCCCCAATTACAACTCT (SEQ ID NO: 34) |
| | Third primer | CTTTGATTACAACTCTTAAGGAAACG (SEQ ID NO: 35) |
| Ya5ACA1736 | First primer | CCTGCTCTGCACACTTCTTG (SEQ ID NO: 36) |
| | Second primer | CCGGCCCGAGAAGGCAAT (SEQ ID NO: 37) |
| | Third primer | GACCTTGACCTAGAGAAGGCAAT (SEQ ID NO: 38) |
| | First primer | CAACGTCCTCCCTAACTACCC (SEQ ID NO: 39) |
| | Second primer | (SEQ ID NO: 37) |
| | Third primer | TGACCTTGACCTAGAGAAGGCAA (SEQ ID NO: 40) |
| | First primer | CCACCTCATGAACTCCCACT (SEQ ID NO: 41) |
| | Second primer | (SEQ ID NO: 37) |
| | Third primer | (SEQ ID NO: 40) |
| Yb8AC1197 | First primer | TGCTGCCCTTAATCTTTACCA (SEQ ID NO: 3) |
| | Second primer | CCCGGCCTTCATTTCTAAG (SEQ ID NO: 4) |
| | Third primer | GAGACTTTCATTTCTAAGATGTCTGG (SEQ ID NO: 5) |
| Yb8NBC126 | First primer | AGCTCCTGGAAAAGGGAAAG (SEQ ID NO: 9) |
| | Second primer | ATCCGATTGGGGCACCTTA (SEQ ID NO: 10) |
| | Third primer | ATGATGATTGGGGCACCTTA (SEQ ID NO: 11) |
| | First primer | CTGTGAAGGCTCACCTGGAG (SEQ ID NO: 42) |
| | Second primer | (SEQ ID NO: 43) |
| | Third primer | (SEQ ID NO: 44) |
| Ya5ac2458 | First primer | AGGGGGAATCGAGTGCTTAT (SEQ ID NO: 45) |
| | Second primer | GGCCCCCTGGAATCTTAAC (SEQ ID NO: 46) |
| | Third primer | GACCCTCCTGGAATCTTAACC (SEQ ID NO: 47) |
| | First primer | TGTTGGATATCCTGGCTGAA (SEQ ID NO: 48) |
| | Second primer | (SEQ ID NO: 46) |
| | Third primer | (SEQ ID NO: 47) |
| | First primer | AGGGGGAATCGAGTGCTTAT (SEQ ID NO: 49) |
| | Second primer | GGCCCCCTGGAATCTTAAC (SEQ ID NO: 50) |
| | Third primer | GACCCTCCTGGAATCTTAACC (SEQ ID NO: 51) |
| Ya5ACA1736 | First primer | TTCCATCTACCTAGAAGTTCCTCA (SEQ ID NO: 52) |
| | Second primer | CGAGAAGGCAATTTTCTACTTAGG (SEQ ID NO: 53) |
| | Third primer | TTGACCTAGAGAAGGCAATTTTC (SEQ ID NO: 54) |
| | First primer | CCACCTCATGAACTCCCACT (SEQ ID NO: 55) |
| | Second primer | CCGGCCCGAGAAGGCAAT (SEQ ID NO: 56) |
| | Third primer | GACCTTGACCTAGAGAAGGCAAT (SEQ ID NO: 57) |

-continued

| Interspersed Element | Primer | Sequence |
|---|---|---|
| | First primer | CAACGTCCTCCCTAACTACCC (SEQ ID NO: 58) |
| | Second primer | (SEQ ID NO: 59) |
| | Third primer | (SEQ ID NO: 60) |
| | First primer | CCTGCTCTGCACACTTCTTG (SEQ ID NO: 61) |
| | Second primer | (SEQ ID NO: 59) |
| | Third primer | (SEQ ID NO: 60) |
| Ya5ac2265 | First primer | CAGCTCAGTCCTAAGCCACA (SEQ ID NO: 62) |
| | Second primer | CCGGCCCAGTTTCTTAATG (SEQ ID NO: 63) |
| | Third primer | CATGAATTCAGTTTCTTAATGATAAGG (SEQ ID NO: 64) |
| | First primer | AGAAGAGTGAATGCACATTTATGA (SEQ ID NO: 65) |
| | Second primer | CCGGCCCAGTTTCTTAATG (SEQ ID NO: 66) |
| | Third primer | CATGAATTCAGTTTCTTAATGATAAGG (SEQ ID NO: 67) |
| Ya5aca1153 | First primer | CAGTGAAAGCTTCTTAGGGGAAT (SEQ ID NO: 68) |
| | Second primer | CCGGCCCTGTGTCTTCTT (SEQ ID NO: 69) |
| | Third primer | TGTCCTTCTGTGTCTTCTTAAATATC (SEQ ID NO: 70) |
| Yb7AD155 | First primer | GTACACATTAAGCACATGGAAGTCA (SEQ ID NO: 71) |
| | Second primer | GCCCGGCCGTTCTTTTTC (SEQ ID NO: 72) |
| | Third primer | GCATGAAATGTTCTTTTTCATCTC (SEQ ID NO: 73) |
| Yb8NBC622 | First primer | TCAAAACTTGCGGATTTTCC (SEQ ID NO: 74) |
| | Second primer | GCGCAATCTCGGCTCCTT (SEQ ID NO: 75) |
| | Third primer | TGTGCAGGGGAATTCCTTCTAA (SEQ ID NO: 76) |
| | First primer | TGGAATACAATGTAACTGGGGATATG (SEQ ID NO: 77) |
| | Second primer | (SEQ ID NO: 75) |
| | Third primer | (SEQ ID NO: 76) |
| Ya5NBC327 | First primer | CTGGGGATATTTTCATAGATGC (SEQ ID NO: 78) |
| | Second primer | GCCCGGCCCTCATTATTC (SEQ ID NO: 79) |
| | Third primer | CCCATTCTCATTATTCTTATTCAACA (SEQ ID NO: 80) |
| | First primer | TGATGTCATGTACAAACAGGGATA (SEQ ID NO: 81) |
| | Second primer | GCCCGGCCCTCATTATTC (SEQ ID NO: 82) |
| | Third primer | CAAGGATACCCATTCTCATTATTCTTA (SEQ ID NO: 83) |
| SVA (chr 2) | First primer | aagcccctgaaaagtgaaat (SEQ ID NO: 84) |
| | Second primer | GGAGAGGGGTCAAATTCTTa (SEQ ID NO: 85) |
| | Third primer | tttctggtCAAATTCTTatctatcaa (SEQ ID NO: 86) |

-continued

| Interspersed Element | Primer | Sequence |
|---|---|---|
| HS-1 (chr 1) | First primer | aaacaggaagcatttcgaggt (SEQ ID NO: 87) |
| | Second primer | GCCCAGCCTCACATAGAt (SEQ ID NO: 88) |
| | Third primer | aaaaatgGCACATAGAtgttgaa (SEQ ID NO: 89) |
| Y (chr 1) | First primer | ccctgaatctgagtgggact (SEQ ID NO: 90) |
| | Second primer | CCGGCCGGCACTTTTatg (SEQ ID NO: 91) |
| | Third primer | tgcatGGCACTTTTatgact (SEQ ID NO: 92) |
| | First primer | (SEQ ID NO: 90) |
| | Second primer | (SEQ ID NO: 91) |
| | Third primer | cagaaatgcatGGCACTTTTat (SEQ ID NO: 93) |
| YC1 (Chr 1 or 2) | First primer | ttcctcttttttctccattttgtt (SEQ ID NO: 94) |
| | Second primer | GGCCTCCCAAGGATTCTTTa (SEQ ID NO: 95) |
| | Third primer | ccttgcttggGGATTCTTTa (SEQ ID NO: 96) |
| YE5 (Chr1 or 2) | First primer | ggtgtagcagaacagacaggag (SEQ ID NO: 97) |
| | Second primer | AAGTGCTGGCTGTTCACCAc (SEQ ID NO: 98) |
| | Third primer | ggtttCTGTTCACCActttca (SEQ ID NO: 99) |
| | First primer | tagcagaacagacaggagacca (SEQ ID NO: 100) |
| | Second primer | (SEQ ID NO: 98) |
| | Third primer | ttggggtttCTGTTCACCAc (SEQ ID NO: 101) |
| | First primer | ggtgtagcagaacagacaggag (SEQ ID NO: 102) |
| | Second primer | AAGTGCTGGCTGTTCACCAc (SEQ ID NO: 103) |
| | Third primer | ggtttCTGTTCACCActttca (SEQ ID NO: 104) |
| YG6 (chr 1 or 2) | First primer | acagctgggcaatacgttct (SEQ ID NO: 105) |
| | Second primer | CCGGCCAAGATTTTCATTt (SEQ ID NO: 106) |
| | Third primer | gagccaAAGATTTTCATTttgatg (SEQ ID NO: 107) |
| | First primer | (SEQ ID NO: 105) |
| | Second primer | (SEQ ID NO: 106) |
| | Third primer | cagagccaAAGATTTTCATTtt (SEQ ID NO: 108) |
| YG6 (chr 1 or 2) | First primer | ttgcagaatgggtttggaag (SEQ ID NO: 109) |
| | Second primer | CCGGCCTTTACCAAACTT (SEQ ID NO: 110) |
| | Third primer | gctgaacTTTACCAAACTTttaaagaa (SEQ ID NO: 111) |
| YA1 (chr 1 or 2) | First primer | agaaggaagaagctccaaacgtg (SEQ ID NO: 112) |
| | Second primer | CTCCTGCGTGGCTTCATT (SEQ ID NO: 113) |
| | Third primer | tgacttGGCTTCATTCTTcggtga (SEQ ID NO: 114) |
| | First primer | (SEQ ID NO: 112) |
| | Second primer | (SEQ ID NO: 113) |
| | Third primer | actgacttGGCTTCATTCTTcg (SEQ ID NO: 115) |
| YA4 (chr 1) | First primer | ttaagaaagtcagcagaaaaacttc (SEQ ID NO: 116) |
| | Second primer | CCCGGCCCAGATTTTACT (SEQ ID NO: 117) |
| | Third primer | ggtcttaCAGATTTTACTTttatttgc (SEQ ID NO: 118) |
| YA5 (chr 2) | First primer | acagaggccaccctgtaggt (SEQ ID NO: 119) |
| | Second primer | ACCTGGCCTGGGTGACTg (SEQ ID NO: 120) |
| | Third primer | tgagaCTGGGTGACTgtgttttt (SEQ ID NO: 121) |
| | First primer | (SEQ ID NO: 119) |
| | Second primer | (SEQ ID NO: 120) |
| | Third primer | tgaaatgagaCTGGGTGACTgt (SEQ ID NO: 122) |
| SVA (chr 3) | First primer | aaagctgggtttccttttgc (SEQ ID NO: 123) |
| | Second primer | GCTGGCCGGAAGTCTTaat (SEQ ID NO: 124) |
| | Third primer | tgaaggataGAAGTCTTaatgcag (SEQ ID NO: 125) |
| YC1 (chr 3) | First primer | cccaataaaatcagcaaatatga (SEQ ID NO: 126) |
| | Second primer | CCGGCCCCACATTTCTT (SEQ ID NO: 127) |
| | Third primer | tgacttttCCACATTTCTTacattg (SEQ ID NO: 128) |
| YB8 (chr 3) | First primer | tgctgcccttaatctttacca (SEQ ID NO: 129) |
| | Second primer | CCCGGCCTTCATTTCTaag (SEQ ID NO: 130) |
| | Third primer | ataagagactTTCATTTCTaagatgtc (SEQ ID NO: 131) |
| YA5 (chr 4) | First primer | ccattaaaggaacaagaatgga (SEQ ID NO: 132) |
| | Second primer | GCCCGGCCAGTAATCTTTa (SEQ ID NO: 133) |
| | Third primer | ctggtcCAGTAATCTTTaatacact (SEQ ID NO: 134) |
| Y (chr 5) | First primer | gtttacctgccttctggctct (SEQ ID NO: 135) |
| | Second primer | GCCCAGCCTACTCTTGTTa (SEQ ID NO: 136) |
| | Third primer | attacctcTACTCTTGTTaaccaacca (SEQ ID NO: 137) |
| YA5 (chr 5) | First primer | tttcttagttcttaacaacagatgc (SEQ ID NO: 138) |
| | Second primer | TATCCTTGCTAGAAGTTactgga (SEQ ID NO: 139) |
| | Third primer | attccaaaaAGAAGTTactggat (SEQ ID NO: 140) |
| YA5 (chr 5) | First primer | aatacagccaaatgaactggaga (SEQ ID NO: 141) |
| | Second primer | TCTGGCCTCCATTTAGTattttt (SEQ ID NO: 142) |
| | Third primer | gcactctctATTTAGTattttctcg (SEQ ID NO: 143) |

-continued

| Interspersed Element | Primer Sequence |
|---|---|
| LINE (chr 7) | First primer tgcacacgtatgtttattgcag (SEQ ID NO: 144) |
| | Second primer TCCTCCCCTCCATTTTCTTa (SEQ ID NO: 145) |
| | Third primer atatatgCCATTTTCTTaatccagtc (SEQ ID NO: 146) |
| YB8 (chr 7) | First primer taatatgaggtgatgggggtta (SEQ ID NO: 147) |
| | Second primer CCGGCCGCCAGTTTCTTa (SEQ ID NO: 148) |
| | Third primer cccagaaCCAGTTTCTTaaatagc (SEQ ID NO: 149) |
| YB8 (chr 7) | First primer tcttgataacatagggaaaatcacttc (SEQ ID NO: 150) |
| | Second primer CCGGCCCAGAGTTCTTaat (SEQ ID NO: 151) |
| | Third primer tgttttgtaCAGAGTTCTTaattgcag (SEQ ID NO: 152) |
| YB8 (chr 7) | First primer ggctagccatatggagaagaa (SEQ ID NO: 153) |
| | Second primer CCGGCCGGAATTCTTatag (SEQ ID NO: 154) |
| | Third primer ttcttctGGAATTCTTatagtttgag (SEQ ID NO: 155) |
| LINE (chr 8) | First primer agcttgagggtggctgtgt (SEQ ID NO: 156) |
| | Second primer GCTCACGCTCTGTGAGTGtt (SEQ ID NO: 157) |
| | Third primer agagagattTGTGAGTGtttaaagatg (SEQ ID NO: 158) |
| SG1 (chr 8) | First primer ttttcggttgtgaactgaagg (SEQ ID NO: 159) |
| | Second primer CCCAGCCTTAAACTGACCat (SEQ ID NO: 160) |
| | Third primer gccccTAAACTGACCattcct (SEQ ID NO: 161) |
| | First primer (SEQ ID NO: 159) |
| | Second primer (SEQ ID NO: 160) |
| | Third primer ccagccccTAAACTGACCat (SEQ ID NO: 162) |
| LINE (chr 9) | First primer aagacccaaattagcgaaagaa (SEQ ID NO: 163) |
| | Second primer AAACCTAGGCATTACCTTTTCaa (SEQ ID NO: 164) |
| | Third primer catttgtcgtTTACCTTTTCaa (SEQ ID NO: 165) |
| YG9 (chr 9) | First primer ctctatatgcactacagttttgtga (SEQ ID NO: 166) |
| | Second primer CCGGCCCCAAGTGTTta (SEQ ID NO: 167) |
| | Third primer ccccagaattaCCAAGTGTTt (SEQ ID NO: 168) |
| YG6 (chr 10) | First primer gaacatccagcaccaaatcc (SEQ ID NO: 169) |
| | Second primer CCCGGCCCTACCTTCtta (SEQ ID NO: 170) |
| | Third primer cctggttgtgtgtTACCTTCtt (SEQ ID NO: 171) |
| YC1 (chr 10) | First primer aggcaggcagatcacttgag (SEQ ID NO: 172) |
| | Second primer CGCGCCCCTAATTCTTTct (SEQ ID NO: 173) |
| | Third primer ccatgcctggCTAATTCTTTc (SEQ ID NO: 174) |
| YC1 (chr 10) | First primer aggggtgagggataaaaga (SEQ ID NO: 175) |
| | Second primer TGAGCCACCGATGAATAAGTT (SEQ ID NO: 176) |
| | Third primer ggtatttggttacATGAATAAGTTCt (SEQ ID NO: 177) |
| YC2 (chr 12) | First primer gagcacattacctataggcagaca (SEQ ID NO: 178) |
| | Second primer GCCCGGCCTTATTTTAGttt (SEQ ID NO: 179) |
| | Third primer tgggttgatagttattTTATTTTAGtt (SEQ ID NO: 180) |
| YA5 (chr 13) | First primer gggattggatagaatgaagaaagg (SEQ ID NO: 181) |
| | Second primer GCCCGGCCTCTCTCTTTag (SEQ ID NO: 182) |
| | Third primer cgcgctctctcTCTCTCTTTag (SEQ ID NO: 183) |
| YA5 (chr 13) | First primer agaagagtgaatgcacatttatga (SEQ ID NO: 184) |
| | Second primer CCCGGCCCAGTTTCTTaat (SEQ ID NO: 185) |
| | Third primer gggagtcatgaattCAGTTTCTTa (SEQ ID NO: 186) |
| LINE (chr 15) | First primer tcctactctcatttcttcacattca (SEQ ID NO: 187) |
| | Second primer CTTGTAAATTTGTCTTGAGTTcattg (SEQ ID NO: 188) |
| | Third primer ggctgtgtgctttTTGAGTTc (SEQ ID NO: 189) |
| Sp (chr 17) | First primer gggaggacattgaaggtaaaca (SEQ ID NO: 190) |
| | Second primer ACCTGGCTGATTGCAGtttt (SEQ ID NO: 191) |
| | Third primer gggccattTGATTGCAGtt (SEQ ID NO: 192) |
| Y (chr 17) | First primer gaggctgcagtgagctatga (SEQ ID NO: 193) |
| | Second primer GCCCGGCCAATTTACAGc (SEQ ID NO: 194) |
| | Third primer aagaactcattcagaAATTTACAGc (SEQ ID NO: 195) |
| Y (chr 19) | First primer tagagtgctgctgtggcaaa (SEQ ID NO: 196) |
| | Second primer GCCCAGCCTAGTGTCCTCT (SEQ ID NO: 197) |
| YA5 | Third primer ttctcctggttacTAGTGTCCTCTc (SEQ ID NO: 198) |
| YA5 (chr 20) | First primer ccaagtcaggtataagcctcaga (SEQ ID NO: 199) |
| | Second primer GCCGGATGTCCACTCttaaa (SEQ ID NO: 200) |
| | Third primer acagaaaggatgtCCACTCtta (SEQ ID NO: 201) |
| YA5 (chr 3) | First primer caggcctggtggtaacaaat (SEQ ID NO: 202) |
| | Second primer CTCGGCCTCCCAATCAAC (SEQ ID NO: 203) |
| | Third primer ggccaatatTCAACATTCTTa (SEQ ID NO: 204) |

-continued

| Interspersed Element | Primer | Sequence |
|---|---|---|
| YA5 (chr 3) | First primer | ccctggacttaccctatctca (SEQ ID NO: 205) |
| | Second primer | TGCTGGGATTACATGGATTTT (SEQ ID NO: 206) |
| | Third primer | ggagaatgtgtgTGGATTTTATTc (SEQ ID NO: 207) |
| SP Chr 22 | First primer | ctttggccctgagagagatg (SEQ ID NO: 208) |
| | Second primer | ACACCCCACCAAAACTGAAT (SEQ ID NO: 209) |
| | Third primer | ttttaaaaccGAATGCCTTt (SEQ ID NO: 210) |
| YE (chr 1) | First primer | agcagctctgggtgtagcag (SEQ ID NO: 211) |
| | Second primer | CCAAAGTGCTGGCTGTTCA (SEQ ID NO: 212) |
| | Third primer | tggggtttCTGTTCACCAct (SEQ ID NO: 213) |
| YG6 (chr 2) | First primer | acagctgggcaatacgttct (SEQ ID NO: 214) |
| | Second primer | CGCCCGGCCAAGATTTTC (SEQ ID NO: 215) |
| | Third primer | cagagccaAAGATTTTCATTt (SEQ ID NO: 216) |
| YC1 (chr 2) | First primer | tctttcctcttttttctccattttg (SEQ ID NO: 217) |
| | Second primer | CTCGGCCTCCCAAGGATT (SEQ ID NO: 218) |
| | Third primer | ccttgcttggGGATTCTTTa (SEQ ID NO: 219) |
| Ya5/8 (Chr 1) | First primer | gtctgcagcttcactcctga (SEQ ID NO: 220) |
| | Second primer | CATTCTCCTGCGTGGCTTC (SEQ ID NO: 221) |
| | Third primer | tgacttGGCTTCATTCTTcg (SEQ ID NO: 222) |
| Ya5 (Chr 1) | First primer | tcctaacaagggacttttgcag (SEQ ID NO: 402) |
| | Second primer | CGGCCTCCCAAAGAAGAT (SEQ ID NO: 403) |
| | Third primer | gatgggaAAGATTCTCCACTTt (SEQ ID NO: 404) |
| YA5 (chr 3) | First primer | caggcctggtggtaacaaat (SEQ ID NO: 405) |
| | Second primer | TCGGCCTCCCAATCAAC (SEQ ID NO: 406) |
| | Third primer | ggccaatatTCAACATTCTTa (SEQ ID NO: 407) |
| Ya5ACA1050 (chr 3) | First primer | ccctggacttaccctatctca (SEQ ID NO: 408) |
| | Second primer | TGCTGGGATTACATGGATTTT (SEQ ID NO: 409) |
| | Third primer | ggagaatgtgtgTGGATTTTATTc (SEQ ID NO: 410) |
| Ya5 (chr 3) | First primer | aaaaacaagcaatggggaaa (SEQ ID NO: 411) |
| | Second primer | GTGTCCGGCCACGTTTAAG (SEQ ID NO: 412) |
| | Third primer | gttttaggtctaACGTTTAAGTCTTt (SEQ ID NO: 413) |
| YB7 (chr 3) | First primer | tgccaggaatggacttacaa (SEQ ID NO: 414) |
| | Second primer | CCCGGCCATGAACTTCTaat (SEQ ID NO: 415) |
| | Third primer | tgacctgcATGAACTTCTaataaaat (SEQ ID NO: 416) |
| | First primer | (SEQ ID NO: 414) |
| | Second primer | (SEQ ID NO: 415) |
| | Third primer | ttcatgacctgcATGAACTTCTa (SEQ ID NO: 417) |
| YB7 (chr 3) | First primer | ggtaatcaacagaagatcataagagga (SEQ ID NO: 418) |
| | Second primer | gttAAGACTTGAGGCCGGG (SEQ ID NO: 419) |
| | Third primer | cttctctcctccCTCAAGTCTTa (SEQ ID NO: 420) |
| Yd8 (chr 4) | First primer | caagtgctggggattacagg (SEQ ID NO: 421) |
| | Second primer | AGACGGGGTTTCACCGTTAG (SEQ ID NO: 422) |
| | Third primer | gcagagagacTAGGAGGCATtc (SEQ ID NO: 423) |
| Y (chr 4) | First primer | ccatggactcatggaatgct (SEQ ID NO: 424) |
| | Second primer | AGCCTGCCACACTTCTTtag (SEQ ID NO: 425) |
| | Third primer | ttccatgacggCACTTCTTt (SEQ ID NO: 426) |
| YA8 (chr 4) | First primer | tgtaggcaaaactttagtttcat (SEQ ID NO: 427) |
| | Second primer | CCCGGCCCAGAAAGAACt (SEQ ID NO: 428) |
| | Third primer | ctcccattatcttCAGAAAGAACt (SEQ ID NO: 429) |
| YA5 (chr 4) | First primer | ccattaaaggaacaagaatgga (SEQ ID NO: 430) |
| | Second primer | GCCCGGCCAGTAATCTTTa (SEQ ID NO: 431) |
| | Third primer | ctggtcCAGTAATCTTTaatacact (SEQ ID NO: 432) |
| YA5 (chr 4) | First primer | ctgagctggaggcataggtc (SEQ ID NO: 433) |
| | Second primer | CCCGGCCCGGCTATTTTa (SEQ ID NO: 434) |
| | Third primer | tgttgcccaGGCTATTTTa (SEQ ID NO: 435) |
| YA5 (chr 4) | First primer | tggagagcattgacagttcat (SEQ ID NO: 436) |
| | Second primer | CCGGCCCCTGCTTCTTat (SEQ ID NO: 437) |
| | Third primer | acacactcacCCTGCTTCTTa (SEQ ID NO: 438) |
| YB3A2 (chr 4) | First primer | caggagaacatggccttcac (SEQ ID NO: 223) |
| | Second primer | CGCCCAGCCTATCCTTTT (SEQ ID NO: 224) |
| | Third primer | atgtctTATCCTTTTgccttttg (SEQ ID NO: 225) |
| | First primer | (SEQ ID NO: 223) |
| | Second primer | (SEQ ID NO: 224) |
| | Third primer | ttgcctttatgtctTATCCTTTTg (SEQ ID NO: 226) |
| YB10 (chr 5) | First primer | agatatgcccaaaggacacaa (SEQ ID NO: 227) |
| | Second primer | GCCCGGCCGAAACTATTa (SEQ ID NO: 228) |
| | Third primer | tccccttccatgtGAAACTATTa (SEQ ID NO: 229) |

-continued

| Interspersed Element | Primer | Sequence |
|---|---|---|
| Y (chr 5) | First primer | ctcattcccttcccactc (SEQ ID NO: 230) |
| | Second primer | GCCCAGCCTACTCTTGTTa (SEQ ID NO: 231) |
| | Third primer | attacctcTACTCTTGTTaaccaacca (SEQ ID NO: 232) |
| Y (chr 5) | First primer | (SEQ ID NO: 230) |
| | Second primer | (SEQ ID NO: 231) |
| | Third primer | tgctaacattacctcTACTCTTGTTa (SEQ ID NO: 233) |
| YB8 (chr 5) | First primer | gtcaacagcctggtgtcatc (SEQ ID NO: 234) |
| | Second primer | AGCCACCGCTCCTTGTAAC (SEQ ID NO: 235) |
| | Third primer | actggcctcCTTGTAACTTTCc (SEQ ID NO: 236) |
| Ya5 (chr 5) | First primer | tttcttagttcttaacaacagatgc (SEQ ID NO: 237) |
| | Second primer | TATCCTTGCTAGAAGTTactgga (SEQ ID NO: 238) |
| | Third primer | attccaaaaAGAAGTTactggat (SEQ ID NO: 239) |
| Ya5 (chr 5) | First primer | aatacagccaaatgaactggaga (SEQ ID NO: 240) |
| | Second primer | TCTGGCCTCCATTTAGTattttt (SEQ ID NO: 241) |
| | Third primer | gcactctctATTTAGTattttctcg (SEQ ID NO: 242) |
| | First primer | aagtgtcaaggagaacaaaatgc (SEQ ID NO: 243) |
| | Second primer | GCCTCTGGCCTCCATTTA (SEQ ID NO: 244) |
| | Third primer | gctccaagagcactctctATTTAGTa (SEQ ID NO: 245) |
| YB3A1 (chr 5) | First primer | cccttttgtgtccctcttca (SEQ ID NO: 246) |
| | Second primer | ACCGCGCCTGGCCTAAAGT (SEQ ID NO: 247) |
| | Third primer | catgtatcccagaactTAAAGTAAAa (SEQ ID NO: 248) |
| YA5 (chr 6) | First primer | ttgccacttaggcaattaagg (SEQ ID NO: 249) |
| | Second primer | GCCTCGGCCTCCCACAAG (SEQ ID NO: 250) |
| | Third primer | ctctgtgcaCACAAGTTTTTCa (SEQ ID NO: 251) |
| YA5 (chr 6) | First primer | aaagggaagcccatcagact (SEQ ID NO: 252) |
| | Second primer | CCCGGCCGAAAATTCTTt (SEQ ID NO: 253) |
| | Third primer | ctgggttGAAAATTCTTtctttt (SEQ ID NO: 254) |
| YB7 (chr 6) | First primer | tgtccaggttaaacttcagttgc (SEQ ID NO: 255) |
| | Second primer | GCCCGGCCCGAAAGAAGT (SEQ ID NO: 256) |
| | Third primer | ggggcaatGAAAGAAGTTt (SEQ ID NO: 257) |
| YI6 (chr 6) | First primer | aggtgctggcactgatgac (SEQ ID NO: 439) |
| | Second primer | CTGGGATTACAAGCGTGAGG (SEQ ID NO: 440) |
| | Third primer | tctcacaagtaagcaAGGTAGAt (SEQ ID NO: 441) |
| YB8 (chr 6) | First primer | ccttaagacctaagccctagtaga (SEQ ID NO: 442) |
| | Second primer | CAGGCGTGAGCCACTAACTT (SEQ ID NO: 443) |
| | Third primer | gttccccaagccaCTAACTTTTa (SEQ ID NO: 444) |
| Y (chr 7) | First primer | gaatgcaagtaaaaaccatgagg (SEQ ID NO: 445) |
| | Second primer | TTTAGTAGAGACGGGGTTAGCA (SEQ ID NO: 446) |
| | Third primer | tccttgtgtctAGCATGTTTTTg (SEQ ID NO: 447) |
| Y (chr 7) | First primer | aaccaaagtgactctgaagaagaaa (SEQ ID NO: 448) |
| | Second primer | TCCTGGGTTCACGTATGATG (SEQ ID NO: 449) |
| | Third primer | ttggaactggcTATGATGTTTg (SEQ ID NO: 450) |
| YA5 (chr 7) | First primer | ggttgatcatctgccgaaag (SEQ ID NO: 451) |
| | Second primer | GCCACCGCGCCCTCTACT (SEQ ID NO: 452) |
| | Third primer | cacctttaccacctTCTACTGTCTa (SEQ ID NO: 453) |
| YA5 (chr 7) | First primer | cttgagcccaggagtttgag (SEQ ID NO: 454) |
| | Second primer | CGCCCGGCCTTATTTTTC (SEQ ID NO: 455) |
| | Third primer | gagaggcccCCTTATTTTCt (SEQ ID NO: 456) |
| YA5 (chr 7) | First primer | aacaaaattcccttcctcca (SEQ ID NO: 457) |
| | Second primer | CGCCCGGCCAGAAGTTAG (SEQ ID NO: 458) |
| | Third primer | ggatatatgctagCAGAAGTTAGATt (SEQ ID NO: 459) |
| YB8 (chr 7) | First primer | cctgaggtgtgtgcttaatcttc (SEQ ID NO: 460) |
| | Second primer | CCCGGCCGCCAGTTTCTT (SEQ ID NO: 461) |
| | Third primer | ttttcccagaaCCAGTTTCTTa (SEQ ID NO: 462) |
| YA5 (chr 8) | First primer | ctctcctgtgcccacttagg (SEQ ID NO: 463) |
| | Second primer | ACGCCCGGCCATATTCTT (SEQ ID NO: 464) |
| | Third primer | tggagtcatgtccatATATTCTTg (SEQ ID NO: 465) |
| SG1 (chr 8) | First primer | ttttcggttgtgaactgaagg (SEQ ID NO: 466) |
| | Second primer | CGCCCAGCCITAAACTGA (SEQ ID NO: 467) |
| | Third primer | accagccccTAAACTGACCa (SEQ ID NO: 468) |
| YA8 (chr 8) | First primer | caggccatgtaagagtagaagga (SEQ ID NO: 469) |
| | Second primer | GCCCGGCCAGAACACTAC (SEQ ID NO: 470) |
| | Third primer | caaccctatgagattAGAACACTACa (SEQ ID NO: 471) |
| Y (chr 10) | First primer | cattgaatgaatggggaagaa (SEQ ID NO: 472) |
| | Second primer | GCCTGGCGCAAAGATAtg (SEQ ID NO: 473) |

-continued

| Interspersed Element | Primer | Sequence |
|---|---|---|
| | Third primer | ttggaaccaaaGCAAAGATAtg (SEQ ID NO: 474) |
| Y (chr 10) | First primer | ggcaaagagtgaactagaatcca (SEQ ID NO: 475) |
| | Second primer | GCGCCCGGCCTCAACTAC (SEQ ID NO: 476) |
| | Third primer | ggaagagcacacTCAACTACTTTTa (SEQ ID NO: 477) |
| YA5 (chr 10) | First primer | ttagctgagggagtcactgga (SEQ ID NO: 258) |
| | Second primer | CCCGGCCGAAGATTTgtt (SEQ ID NO: 259) |
| | Third primer | gcatgtctcctgtGAAGATTTg (SEQ ID NO: 260) |
| YB7 (chr 10) | First primer | tggccaacaaatacgtgaaa (SEQ ID NO: 261) |
| | Second primer | GCGCCCGGCCCTTAACTT (SEQ ID NO: 262) |
| | Third primer | cagcatctgttgtttCTTAACTTtt (SEQ ID NO: 263) |
| YC1 (chr 10) | First primer | aggcaggcagatcacttg (SEQ ID NO: 264) |
| | Second primer | CGCGCCCCTAATTCTTTct (SEQ ID NO: 265) |
| | Third primer | ccatgcctggCTAATTCTTTc (SEQ ID NO: 266) |
| YC1 (chr 10) | First primer | tgaaatggactgtgggact (SEQ ID NO: 267) |
| | Second primer | CGTGAGCCACCGATGAATA (SEQ ID NO: 268) |
| | Third primer | tggtatttggttacATGAATAAGGTCt (SEQ ID NO: 269) |
| YG6 (chr 10) | First primer | ctcggcataaataaaactttaagga (SEQ ID NO: 270) |
| | Second primer | GCGCCCGGCCAATTCTAC (SEQ ID NO: 271) |
| | Third primer | ggcttgctcagAATTCTACCTTc (SEQ ID NO: 272) |
| YG6 (chr 10) | First primer | gaacatccagcaccaaatcc (SEQ ID NO: 273) |
| | Second primer | CCCGGCCCTACCTTCtta (SEQ ID NO: 274) |
| | Third primer | cctggttgtgtgtTACCTTCtt (SEQ ID NO: 275) |
| YA5 (chr 11) | First primer | ccttgacaggcactaaccact (SEQ ID NO: 276) |
| | Second primer | CTCCCAAAGTGCGGTTCTC (SEQ ID NO: 277) |
| | Third primer | gaatgtggagtacatGGTTCTCTTTa (SEQ ID NO: 278) |
| YA5 (chr 11) | First primer | aggagaattgcttgaacctg (SEQ ID NO: 279) |
| | Second primer | TCCCAAGCTGAGATCCTTTC (SEQ ID NO: 280) |
| | Third primer | ggtatgctgagaTCCTTTCTc (SEQ ID NO: 281) |
| YA5 (chr 11) | First primer | ggttttaccaggaatgtagtttgg (SEQ ID NO: 282) |
| | Second primer | GCCCGGCCTCATCCATTC (SEQ ID NO: 283) |
| | Third primer | gcctccctTCATCCATTCTTa (SEQ ID NO: 284) |
| YX (chr 11) | First primer | ccagatggaagacatgcaca (SEQ ID NO: 285) |
| | Second primer | GCCCGGCCCATTCAGTCT (SEQ ID NO: 286) |
| | Third primer | ggagggttCATrCAGTCTTttg (SEQ ID NO: 287) |
| YB8 (chr 11) | First primer | tcaaaaagactatctttccccatt (SEQ ID NO: 288) |
| | Second primer | TGGGACTGGGACTTAGGA (SEQ ID NO: 289) |
| | Third primer | aaagttatgggagTTAGGATTTCaa (SEQ ID NO: 290) |
| YC2 (chr 11) | First primer | gcggaaaactaaaggcaaag (SEQ ID NO: 291) |
| | Second primer | CGCCCGGCCTTATTTTAG (SEQ ID NO: 292) |
| | Third primer | tgggttgatagttattTTATTTTAGtt (SEQ ID NO: 293) |
| YA5 (chr 12) | First primer | tgatccatgaacattcactctg (SEQ ID NO: 294) |
| | Second primer | GCCCGGCCCAGATCTTTC (SEQ ID NO: 295) |
| | Third primer | cagtgcactttCAGATCTTTCTtta (SEQ ID NO: 296) |
| YA5 (chr 13) | First primer | gggattggatagaatgaagaaagg (SEQ ID NO: 297) |
| | Second primer | GCCCGGCCTCTCTCTTTag (SEQ ID NO: 298) |
| | Third primer | cgcgctctctcTCTCTCTTTag (SEQ ID NO: 299) |
| YA5 (chr 13) | First primer | gggattggatagaatgaagaaagg (SEQ ID NO: 300) |
| | Second primer | GCCCGGCCTCTCTCTTTag (SEQ ID NO: 301) |
| | Third primer | cgcgctctctcTCTCTCTTTag (SEQ ID NO: 302) |
| YA5 (chr 13) | First primer | acatggacacgcatgaaaga (SEQ ID NO: 303) |
| | Second primer | CCCGGCCACAACCCTCATT (SEQ ID NO: 304) |
| | Third primer | ggtagttaccttacaACCCTCATTTTTa (SEQ ID NO: 305) |
| YA5 (chr 13) | First primer | aagaagagtgaatgcacatttatga (SEQ ID NO: 306) |
| | Second primer | CCCGGCCCAGTTTCTTaat (SEQ ID NO: 307) |
| | Third primer | gggagtcatgaattCAGTTTCTTa (SEQ ID NO: 308) |
| YA1 (chr 15) | First primer | cccaagtctaaaccaggaagaa (SEQ ID NO: 309) |
| | Second primer | CCCAGCTACCAGTTCCTCTTT (SEQ ID NO: 310) |
| | Third primer | atggtaccagcgCCTCTTTg (SEQ ID NO: 311) |
| YA5 (chr 15) | First primer | tgttttccttgccacactg (SEQ ID NO: 312) |
| | Second primer | GCGCCCGGCCTTACTCTC (SEQ ID NO: 313) |
| | Third primer | tcttcgtggtcTTACTCTCTCTTc (SEQ ID NO: 314) |

-continued

| Interspersed Element | Primer | Sequence |
|---|---|---|
| Sp (chr 17) | First primer | agctgccaataaggctgaaa (SEQ ID NO: 315) |
| | Second primer | CCGCACCTGGCTGATTGC (SEQ ID NO: 316) |
| | Third primer | gggccattTGATTGCAGtt (SEQ ID NO: 317) |
| Y (chr 17) | First primer | cctagctactaggaagcctgag (SEQ ID NO: 318) |
| | Second primer | CGCCCGGCCAATTTACAG (SEQ ID NO: 319) |
| | Third primer | aagaactcattcagaAATTTACAGc (SEQ ID NO: 320) |
| Y (chr 19) | First primer | tagagtgctgctgtggcaaa (SEQ ID NO: 321) |
| | Second primer | GCCCAGCCTAGTGTCCTCT (SEQ ID NO: 322) |
| | Third primer | tggttacCTAGTGGCCTCTct (SEQ ID NO: 323) |
| YA5 (chr 20) | First primer | ccaagtcaggtataagcctcaga (SEQ ID NO: 324) |
| | Second primer | GCCGGATGTCCACTCttaaa (SEQ ID NO: 325) |
| | Third primer | acagaaaggatgtCCACTCtta (SEQ ID NO: 326) |
| YA5 (chr 20) | First primer | tggcttccttttctttcctta (SEQ ID NO: 327) |
| | Second primer | GCCCGGCCAAAATGACTG (SEQ ID NO: 328) |
| | Third primer | caagcagtgagaAAAATGACTGTt (SEQ ID NO: 329) |
| YA5 (Y) | First primer | tgctgttccagaaacacacttt (SEQ ID NO: 330) |
| | Second primer | GCCCGGCCGACACTTCTT (SEQ ID NO: 331) |
| | Third primer | cacaatcaccttGACACTTTTTa (SEQ ID NO: 332) |
| YB8 (Y) | First primer | tgatggggatagaggaagaaga (SEQ ID NO: 333) |
| | Second primer | CGCCCGGCCTGTCTACCA (SEQ ID NO: 334) |
| | Third primer | gcatctctTGTCTACCAGTTTTaa (SEQ ID NO: 335) |
| YB8 (Y) | First primer | cctaaggtgagtaaggttaaatcctg (SEQ ID NO: 336) |
| | Second primer | CGCCCGGCCTGGATTCTT (SEQ ID NO: 337) |
| | Third primer | tgttgtagctgtTGGATTCTTa (SEQ ID NO: 338) |
| SC (X) | First primer | ccgaattcaaagaaggatca (SEQ ID NO: 339) |
| | Second primer | ACGCCCAGTCCTTAGGCTAC (SEQ ID NO: 340) |
| | Third primer | tgaccaacactCTTAAGCTACTTtt (SEQ ID NO: 341) |
| SC (X) | First primer | ctgtatcctcatgttctgttgga (SEQ ID NO: 342) |
| | Second primer | CTGCCCACTCATTTTCTTagg (SEQ ID NO: 343) |
| | Third primer | ccactcgttttctcTTTCTTag (SEQ ID NO: 344) |
| YA3A1 (X) | First primer | acttgttgaccgagccacat (SEQ ID NO: 345) |
| | Second primer | GCCCGGCCAAGAAACTGG (SEQ ID NO: 346) |

-continued

| Interspersed Element | Primer | Sequence |
|---|---|---|
| | Third primer | tccagttAAGAAACTGGTCCCttc (SEQ ID NO: 347) |
| YD8 (X) | First primer | cagccagaagtggcttccta (SEQ ID NO: 348) |
| | Second primer | CCCGGCCGTCCTTTCATT (SEQ ID NO: 349) |
| | Third primer | gccccaatTCCTTTCATTtt (SEQ ID NO: 350) |
| YA4 (X) | First primer | tgctggtcagatagaccctgt (SEQ ID NO: 351) |
| | Second primer | GCCCGGCCAACACTGCTT (SEQ ID NO: 352) |
| | Third primer | ggggtgaagtAACACTGCTTTt (SEQ ID NO: 353) |
| YG6 (X) | First primer | gaatctagcccttcccttgc (SEQ ID NO: 354) |
| | Second primer | CCCGGCAGCCAAGAAGTC (SEQ ID NO: 355) |
| | Third primer | aaccagAGCCAAGAAGTCTTatg (SEQ ID NO: 356) |
| Y (X) | First primer | tggtaaaaatggggtgacaaa (SEQ ID NO: 357) |
| | Second primer | CACCCGGCCTACAATTTTT (SEQ ID NO: 358) |
| | Third primer | gccacagatgatTACAATTTTTCaa (SEQ ID NO: 359) |
| SVA (Chr 1) | First primer | ccagtgcctgtgtatctaagtga (SEQ ID NO: 360) |
| | Second primer | GAGAGGGAGAGGGAACTGAA (SEQ ID NO: 361) |
| | Third primer | tcaatggagtacaGAACTGAATCTTa (SEQ ID NO: 362) |
| SVA (Chr 1) | First primer | gaaatgaataagcttcttggatagtg (SEQ ID NO: 363) |
| | Second primer | GGGAGAGGGAGAGGTCATTA (SEQ ID NO: 364) |
| | Third primer | cggccaatcTCATTATTTTCa (SEQ ID NO: 365) |
| SVA (Chr 3) | First primer | aaagctgggtttcctttgc (SEQ ID NO: 366) |
| | Second primer | GGCTGGCCGGAAGTCTTa (SEQ ID NO: 367) |
| | Third primer | tggtgtcttgaaggataGAAGTCTTa (SEQ ID NO: 368) |
| SVA (Chr 19) | First primer | cgtggtgatgtgcactttta (SEQ ID NO: 369) |
| | Second primer | TTAAATTTTTGACCGGGTTT (SEQ ID NO: 370) |
| | Third primer | gaaggaaaagtagttaaGGGTTTTTg (SEQ ID NO: 371) |
| SVA (Chr 22) | First primer | ccctgctatcctaaatgctg (SEQ ID NO: 372) |
| | Second primer | GTGATGGCGGGCTTAACCT (SEQ ID NO: 373) |
| | Third primer | cagcccaccCTTAACCTCTa (SEQ ID NO: 374) |
| LINE (Chr 2) | First primer | tttcctcttgttcgtgatgg (SEQ ID NO: 375) |
| | Second primer | GGTGGTTCCAAGCTGTTTTC (SEQ ID NO: 376) |
| | Third primer | ccaaaaaccccatAGCTGTTTTCTa (SEQ ID NO: 377) |

-continued

| Interspersed Element | Primer | Sequence |
|---|---|---|
| LINE (Chr 2) | First primer | tgggcatcactcagctctaa (SEQ ID NO: 378) |
| | Second primer | CTCCTCCTTCCGGCACTG (SEQ ID NO: 379) |
| | Third primer | acttctCGGCACTGGCTTt (SEQ ID NO: 380) |
| LINE (Chr 5) | First primer | ttgctcagagcccataagga (SEQ ID NO: 381) |
| | Second primer | TGGCTCCTCCAAGCCTTC (SEQ ID NO: 382) |
| | Third primer | ctacacattaaattAAGCCTTCAAAt t (SEQ ID NO: 383) |
| LINE (Chr 6) | First primer | tgaataccatgatatgccaaa (SEQ ID NO: 384) |
| | Second primer | TGATTGCCATTCACACTCC (SEQ ID NO: 385) |
| | Third primer | gaaattgcCACACTCCTTTTc (SEQ ID NO: 386) |
| LINE (Chr 7) | First primer | agcagcatgatttataatccttt (SEQ ID NO: 387) |
| | Second primer | GGTCCCCTAACAGGAGCAC (SEQ ID NO: 388) |
| | Third primer | tgtggagaaatatGAACACTTTTac (SEQ ID NO: 389) |
| LINE (Chr 8) | First primer | taacatttgaccaaacagttgag (SEQ ID NO: 390) |
| | Second primer | CCCACTTTTTGACCTTTCa (SEQ ID NO: 391) |
| | Third primer | ccgctgcttctaACCTTTCa (SEQ ID NO: 392) |
| LINE (Chr 8) | First primer | ttctcttcttccctctctgagc (SEQ ID NO: 393) |
| | Second primer | CTTGGCTCCTCCTGCAAAT (SEQ ID NO: 394) |
| | Third primer | tctctgctcatTGCAAATCTTa (SEQ ID NO: 395) |
| LINE (Chr 8) | First primer | ctctggagaagggtgcattg (SEQ ID NO: 396) |
| | Second primer | CGTCGCTCACGCTCTGTG (SEQ ID NO: 397) |
| | Third primer | ttagagagagagattTGTGAGTGtt (SEQ ID NO: 398) |
| LINE (Chr 10) | First primer | tgctagtagaacccacgaggt (SEQ ID NO: 399) |
| | Second primer | GGCACAAGACAGGGATGC (SEQ ID NO: 400) |
| | Third primer | gaaaagacaaaGTTGCATTGTTa (SEQ ID NO: 401). |

24. A method for genetic detection, comprising:
carrying out a polymerase chain reaction (PCR) on a DNA sample with primer sets to produce amplified DNA products, the primer sets comprising:
a primer set for a filled site which contains an interspersed element, the primer set for the filled site comprising:
a forward primer complementary to a first flanking genomic sequence; and
a reverse primer complementary to a sequence comprised of a second flanking genomic sequence, a direct repeat sequence flanking the 3' side of the second flanking genomic sequence and the 5' side of the interspersed element, and a part of the 5' sequence of the interspersed element next to the direct repeat sequence; and
a primer set for an empty site which does not contain the interspersed element, the primer set for the empty site comprising:
said forward primer complementary to the first flanking genomic sequence existing in the empty site and the filled site; and
a reverse primer complementary to a sequence comprised of the direct repeat sequence and third flanking genomic sequences on both sides of the direct repeat sequence in the empty site; and
analyzing the amplified DNA products to detect presence or absence of the interspersed element insertion at the site.

25. A primer set for a polymorphic marker site, comprising:
a first primer for a filled site containing an interspersed element and an empty site which does not contain the interspersed element, the first primer complementary to a first flanking genomic sequence in the filled site and the empty site;
a second primer for the filled site, the second primer complementary to a sequence having a second flanking genomic sequence, a direct repeat sequence next to the second flanking genomic sequence and a part of the interspersed element next to the direct repeat sequence in the filled site; and
a third primer for the empty site, the third primer complementary to a sequence having the direct repeat sequence and third flanking genomic sequences on both sides of the direct repeat sequence in the empty site.

26. The primer set of claim 25, wherein the direct repeat sequence is not more than about 14 base pairs in length, and the third primer is less than or equal to about 20 base pairs in length.

27. The primer set of claim 25, wherein the first primer is a forward primer for the filled site and the empty site, the second primer is a reverse primer for the filled site, and the third primer is a reverse primer for the empty site.

28. The primer set of claim 25, wherein in the filled site, the first flanking genomic sequence is in front of the second flanking genomic sequence, the direct repeat is present on the 5' flanking side of the interspersed element and the part of the interspersed element included in the sequence complementary to the second primer is part of the 5' sequence of the interspersed element.

29. The primer set of claim 25, wherein the amplified DNA products for the filled site and the empty site have substantially the same length.

30. A kit for genetic detection, comprising a polymerase and the primer set of claim 25.

* * * * *

SEQUENCE LISTING

```
<160> NUMBER OF SEQ ID NOS: 481

<210> SEQ ID NO 1
<211> LENGTH: 430
<212> TYPE: DNA
<213> ORGANISM: Homo sapiens

<400> SEQUENCE: 1
cctccctaca gaaatcaact agatttcttt aaatttccca gacatcttag aaatgaaggc     60
cgggcgcggt ggctcacgcc tgtaatccca gcactttggg aggccgaggc gggtggatca    120
tgaggtcaag agatcgagac catcctggct aacaaggtga aaccccgtct ctactaaaaa    180
tacaaaaaat tagccgggcg cggtggcggg cgcctgtagt cccagctact cgggaggctg    240
aggcaggaga atggcgtgaa cccgggaagc ggagcttgca gtgagccgag attgcgccac    300
tgcagtccgc agtccggcct gggcgacaga gcgagactcc gtctcaaaaa aaaaaaaaaa    360
aaaaaaaaaa aaaagaaat gaaagtctct tatcttaata tagtttaaag gtgtgtttcc    420
cttgcccctc                                                          430

<210> SEQ ID NO 2
<211> LENGTH: 104
<212> TYPE: DNA
<213> ORGANISM: Homo sapiens

<400> SEQUENCE: 2
cctccctaca gaaatcaact agatttcttt aaatttccca gacatcttag aaatgaaagt     60
ctcttatctt aatatagttt aaaggtgtgt ttcccttgcc cctc                     104

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
tgctgccctt aatctttacc a                                              21

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
cccggccttc atttctaag                                                 19

<210> SEQ ID NO 5
<211> LENGTH: 26
<212> TYPE: DNA
<213> ORGANISM: Artificial
<220> FEATURE:
<223> OTHER INFORMATION: Primer

<400> SEQUENCE: 5
```

```
gagactttca tttctaagat gtctgg                                            26

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
tgctgagctc catgctattc                                                   20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
agacggggta ccagctcttg                                                   20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
gctcaccagc tcttgacgta                                                   20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
agctcctgga aagggaaag                                                    20

<210> SEQ ID NO 10
<211> LENGTH: 19
<212> TYPE: DNA
<213> ORGANISM: Artificial
<220> FEATURE:
<223> OTHER INFORMATION: Primer

<400> SEQUENCE: 10
atccgattgg ggcacctta                                                    19

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
atgatgattg gggcacctta                                                   20

<210> SEQ ID NO 12
<211> LENGTH: 761
<212> TYPE: DNA
```

<213> ORGANISM: Homo sapiens

<400> SEQUENCE: 12

```
acectttgta gagacagagt ttcactacat tgcccgggtt gaccaagcaa aatttcttac      60
atggtctcat taacagtttc tatttctgct gcccttaatc tttaccatct aagtgctttg     120
gaagtttcct ccctacagaa atcaactaga tttctttaaa tttcccagac atcttagaaa     180
tgaaggccgg gcgcggtggc tcacgcctgt aatcccagca ctttgggagg ccgaggcggg     240
tggatcatga ggtcaagaga tcgagaccat cctggctaac aaggtgaaac cccgtctcta     300
ctaaaaatac aaaaaattag ccgggcgcgg tggcgggcgc ctgtagtccc agctactcgg     360
gaggctgagg caggagaatg gcgtgaaccc gggaagcgga gcttgcagtg agccgagatt     420
gcgccactgc agtccgcagt ccggcctggg cgacagagcg agactccgtc tcaaaaaaaa     480
aaaaaaaaaa aaaaaaaaaa aagaaatgaa agtctcttat cttaatatag tttaaggtg      540
tgtttccctt gcccctcagt attgtaaata tctaaacaga tgtgttgcca caatggggc      600
aattttttaaa tttaaaaaca atttttttttt tgtatgtgtg ctggaccaaa ccgtggcatg    660
ggagtgattc ccacattaag gaatgtctca acatccttca tagcaattct tgactaccaa     720
atccagtctc aatatcaagc attaatagaa ctatgtatac c                        761
```

<210> SEQ ID NO 13
<211> LENGTH: 435
<212> TYPE: DNA
<213> ORGANISM: Homo sapiens

<400> SEQUENCE: 13

```
acectttgta gagacagagt ttcactacat tgcccgggtt gaccaagcaa aatttcttac      60
atggtctcat taacagtttc tatttctgct gcccttaatc tttaccatct aagtgctttg     120
gaagtttcct ccctacagaa atcaactaga tttctttaaa tttcccagac atcttagaaa     180
tgaaagtctc ttatcttaat atagtttaaa ggtgtgtttc ccttgcccct cagtattgta     240
aatatctaaa cagatgtgtt gccacaaatg gggcaatttt taaatttaaa acaattttt      300
tttttgtatg tgtgctggac caaaccgtgg catgggagtg attcccacat taaggaatgt     360
ctcaacatcc ttcatagcaa ttcttgacta ccaaatccag tctcaatatc aagcattaat     420
agaactatgt atacc                                                      435
```

<210> SEQ ID NO 14
<211> LENGTH: 430
<212> TYPE: DNA
<213> ORGANISM: Homo sapiens

<400> SEQUENCE: 14

```
cctccctaca gaaatcaact agatttcttt aaatttccca gacatcttag aaatgaaggc      60
cgggcgcggt ggctcacgcc tgtaatccca gcactttggg aggccgaggc gggtggatca     120
tgaggtcaag agatcgagac catcctggct aacaaggtga accccgtctc tactaaaaa      180
tacaaaaaat tagccgggcg cggtggcggg cgcctgtagt cccagctact cgggaggctg     240
aggcaggaga atggcgtgaa cccgggaagc ggagcttgca gtgagccgag attgcgccac     300
tgcagtccgc agtccggcct gggcgacaga gcgagactcc gtctcaaaaa aaaaaaaaaa     360
aaaaaaaaaa aaaagaaat gaaagtctct tatcttaata gtttaaag gtgtgtttcc       420
cttgcccctc                                                            430
```

<210> SEQ ID NO 15
<211> LENGTH: 104
<212> TYPE: DNA
<213> ORGANISM: Homo sapiens

<400> SEQUENCE: 15

```
cctccctaca gaaatcaact agatttcttt aaatttccca gacatcttag aaatgaaagt    60
ctcttatctt aatatagttt aaaggtgtgt ttcccttgcc cctc                    104
```

<210> SEQ ID NO 16
<211> LENGTH: 910
<212> TYPE: DNA
<213> ORGANISM: Homo sapiens

<400> SEQUENCE: 16

```
agatctgtat tttgcaaata ttttcttcaa tatgtggctt gtcttttgt tctcttgaca     60 aggtctcttc cagagtataa actgtaaata ttaagaaatc cacattgtca tttcttctgt   120
gtatatcaac cttctgtgtc atttgttaaa attcattacc aaacgcaaag gcacacagct   180
tttcctctat agtttcttct agaaattgta tagttttgca ttttagtgt aaggatgatt    240 ttgagtgatt atttgtgtaa gttgtaaagt tttcatctac atgcatatca tttcttatgg   300
tttccaatta atcattccct cactattttt gggaaagaca caggatagtg ggctctgtta   360
gagtagatag ctagctagac atgaacagga ggggagctc ctggaaaagg gaaagtctgt    420
gaaggctcac ctggagggac caccaaaaat gcacatatta gtagcatctc tagtgctgga   480
gtggatgggc acttgtcaat tgtggttagg agggagaaga ggtacctacg cagaaacacc   540
ctagaacttc tcttaaggtg ccccaatcgg atgggcgcgg tggctcacgc ctgtaatccc   600
agcactttgg gaggccgagg cgggtggatc atgaggtcag gagatcgaga ccatcctggc   660
taacaaggtg aaaccccgtc tctactaaaa atacaaaaaa ttagccgggc acggtggcgg   720
gcgcctgtag tcccagctct cgggaggct gaggcaggaa aatggcgtga acccgggaag    780
tggagcttgc attgagccga gattgcgcca ctgcagtccg cagtccggcc tgggcgacag   840
agcgagactc cgtctcaaaa aaaaaaaaa aaaaagatg ccccaatcat cattcactct     900
gcaataaaaa                                                          910
```

<210> SEQ ID NO 17
<211> LENGTH: 590
<212> TYPE: DNA
<213> ORGANISM: Homo sapiens

<400> SEQUENCE: 17

```
agatctgtat tttgcaaata ttttcttcaa tatgtggctt gtcttttgt tctcttgaca     60 aggtctcttc cagagtataa actgtaaata ttaagaaatc cacattgtca tttcttctgt   120
gtatatcaac cttctgtgtc atttgttaaa attcattacc aaacgcaaag gcacacagct   180
tttcctctat agtttcttct agaaattgta tagttttgca ttttagtgt aaggatgatt    240 ttgagtgatt atttgtgtaa gttgtaaagt tttcatctac atgcatatca tttcttatgg   300
tttccaatta atcattccct cactattttt gggaaagaca caggatagtg ggctctgtta   360
gagtagatag ctagctagac atgaacagga ggggagctc ctggaaaagg gaaagtctgt    420
gaaggctcac ctggagggac caccaaaaat gcacatatta gtagcatctc tagtgctgga   480
gtggatgggc acttgtcaat tgtggttagg agggagaaga ggtacctacg cagaaacacc   540
ctagaacttc tcttaaggtg ccccaatcat cattcactct gcaataaaaa              590
```

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18
tgtgtcaaag agcgagatga aca                                    23

<210> SEQ ID NO 19
<211> LENGTH: 19
<212> TYPE: DNA
<213> ORGANISM: Artificial
<220> FEATURE:
<223> OTHER INFORMATION: Primer

<400> SEQUENCE: 19
gggttcacgc cattctagc                                         19

<210> SEQ ID NO 20
<211> LENGTH: 23
<212> TYPE: DNA
<213> ORGANISM: Artificial
<220> FEATURE:
<223> OTHER INFORMATION: Reverse primer for empty Yb8NBC67

<400> SEQUENCE: 20
ttcatagcag cctattctag cag                                    23

<210> SEQ ID NO 21
<211> LENGTH: 23
<212> TYPE: DNA
<213> ORGANISM: Artificial
<220> FEATURE:
<223> OTHER INFORMATION: Primer

<400> SEQUENCE: 21
aaacataatt tagttcccca caa                                    23

<210> SEQ ID NO 22
<211> LENGTH: 18
<212> TYPE: DNA
<213> ORGANISM: Artificial
<220> FEATURE:
<223> OTHER INFORMATION: Primer

<400> SEQUENCE: 22
cccggccaag atccattc                                          18

<210> SEQ ID NO 23
<211> LENGTH: 19
<212> TYPE: DNA
<213> ORGANISM: Artificial
<220> FEATURE:
<223> OTHER INFORMATION: Primer

<400> SEQUENCE: 23
cccccagaag aaccattct                                         19

<210> SEQ ID NO 24
<211> LENGTH: 20
<212> TYPE: DNA
<213> ORGANISM: Artificial
<220> FEATURE:
<223> OTHER INFORMATION: Primer

```
<400> SEQUENCE: 24
gccactcgta ggcagtcatt                                              20

<210> SEQ ID NO 25
<211> LENGTH: 18
<212> TYPE: DNA
<213> ORGANISM: Artificial
<220> FEATURE:
<223> OTHER INFORMATION: Primer

<400> SEQUENCE: 25
gcccggccgt tacggttt                                                18

<210> SEQ ID NO 26
<211> LENGTH: 22
<212> TYPE: DNA
<213> ORGANISM: Artificial
<220> FEATURE:
<223> OTHER INFORMATION: Primer

<400> SEQUENCE: 26
agcatgtcaa ctgttacgta tg                                           22

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
catagcacca ggtgaccaca                                              20

<210> SEQ ID NO 28
<211> LENGTH: 18
<212> TYPE: DNA
<213> ORGANISM: Artificial
<220> FEATURE:
<223> OTHER INFORMATION: Primer

<400> SEQUENCE: 28
gcgcccggcc tctttctt                                                18

<210> SEQ ID NO 29
<211> LENGTH: 26
<212> TYPE: DNA
<213> ORGANISM: Artificial
<220> FEATURE:
<223> OTHER INFORMATION: Primer

<400> SEQUENCE: 29
aaaggttaaa ccatcttctt tctaca                                       26

<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
gcacttcaca ccatttctgc                                              20

<210> SEQ ID NO 31
```

```
<211> LENGTH: 18
<212> TYPE: DNA
<213> ORGANISM: Artificial
<220> FEATURE:
<223> OTHER INFORMATION: Reverse primer for filled YC1NBC60

<400> SEQUENCE: 31
gcgcccggcc tctttctt                                                   18

<210> SEQ ID NO 32
<211> LENGTH: 26
<212> TYPE: DNA
<213> ORGANISM: Artificial
<220> FEATURE:
<223> OTHER INFORMATION: Reverse primer for empty YC1NBC60

<400> SEQUENCE: 32
aaaggttaaa ccatcttctt tctaca                                          26

<210> SEQ ID NO 33
<211> LENGTH: 25
<212> TYPE: DNA
<213> ORGANISM: Artificial
<220> FEATURE:
<223> OTHER INFORMATION: Primer

<400> SEQUENCE: 33
aggacaggtt aataatccag aaaaa                                           25

<210> SEQ ID NO 34
<211> LENGTH: 19
<212> TYPE: DNA
<213> ORGANISM: Artificial
<220> FEATURE:
<223> OTHER INFORMATION: Primer

<400> SEQUENCE: 34
cggccccaat tacaactct                                                  19

<210> SEQ ID NO 35
<211> LENGTH: 26
<212> TYPE: DNA
<213> ORGANISM: Artificial
<220> FEATURE:
<223> OTHER INFORMATION: Primer

<400> SEQUENCE: 35
ctttgattac aactcttaag gaaacg                                          26

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
cctgctctgc acacttcttg                                                 20

<210> SEQ ID NO 37
<211> LENGTH: 18
<212> TYPE: DNA
<213> ORGANISM: Artificial
<220> FEATURE:
<223> OTHER INFORMATION: Primer

<400> SEQUENCE: 37
```

```
ccggcccgag aaggcaat                                                  18

<210> SEQ ID NO 38
<211> LENGTH: 23
<212> TYPE: DNA
<213> ORGANISM: Artificial
<220> FEATURE:
<223> OTHER INFORMATION: Primer

<400> SEQUENCE: 38
gaccttgacc tagagaaggc aat                                            23

<210> SEQ ID NO 39
<211> LENGTH: 21
<212> TYPE: DNA
<213> ORGANISM: Artificial
<220> FEATURE:
<223> OTHER INFORMATION: Primer

<400> SEQUENCE: 39
caacgtcctc cctaactacc c                                              21

<210> SEQ ID NO 40
<211> LENGTH: 22
<212> TYPE: DNA
<213> ORGANISM: Artificial
<220> FEATURE:
<223> OTHER INFORMATION: Primer

<400> SEQUENCE: 40
tgaccttgac ctagagaagg ca                                             22

<210> SEQ ID NO 41
<211> LENGTH: 20
<212> TYPE: DNA
<213> ORGANISM: Artificial
<220> FEATURE:
<223> OTHER INFORMATION: Primer

<400> SEQUENCE: 41
ccacctcatg aactcccact                                                20

<210> SEQ ID NO 42
<211> LENGTH: 20
<212> TYPE: DNA
<213> ORGANISM: Artificial
<220> FEATURE:
<223> OTHER INFORMATION: Primer

<400> SEQUENCE: 42
ctgtgaaggc tcacctggag                                                20

<210> SEQ ID NO 43
<211> LENGTH: 19
<212> TYPE: DNA
<213> ORGANISM: Artificial
<220> FEATURE:
<223> OTHER INFORMATION: Primer

<400> SEQUENCE: 43
atccgattgg ggcaccttta                                                19

<210> SEQ ID NO 44
<211> LENGTH: 20
<212> TYPE: DNA
```

```
<213> ORGANISM: Artificial
<220> FEATURE:
<223> OTHER INFORMATION: Primer

<400> SEQUENCE: 44
atgatgattg gggcacctta                                                    20

<210> SEQ ID NO 45
<211> LENGTH: 20
<212> TYPE: DNA
<213> ORGANISM: Artificial
<220> FEATURE:
<223> OTHER INFORMATION: Primer

<400> SEQUENCE: 45 aggggggaatc gagtgcttat                                                   20

<210> SEQ ID NO 46
<211> LENGTH: 19
<212> TYPE: DNA
<213> ORGANISM: Artificial
<220> FEATURE:
<223> OTHER INFORMATION: Primer

<400> SEQUENCE: 46 ggcccctgg aatcttaac                                                      19

<210> SEQ ID NO 47
<211> LENGTH: 21
<212> TYPE: DNA
<213> ORGANISM: Artificial
<220> FEATURE:
<223> OTHER INFORMATION: Primer

<400> SEQUENCE: 47
gaccctcctg gaatcttaac c                                                  21

<210> SEQ ID NO 48
<211> LENGTH: 20
<212> TYPE: DNA
<213> ORGANISM: Artificial
<220> FEATURE:
<223> OTHER INFORMATION: Forward primer for Ya5ac2458

<400> SEQUENCE: 48
tgttggatat cctggctgaa                                                    20

<210> SEQ ID NO 49
<211> LENGTH: 20
<212> TYPE: DNA
<213> ORGANISM: Artificial
<220> FEATURE:
<223> OTHER INFORMATION: Primer

<400> SEQUENCE: 49 aggggggaatc gagtgcttat                                                   20

<210> SEQ ID NO 50
<211> LENGTH: 19
<212> TYPE: DNA
<213> ORGANISM: Artificial
<220> FEATURE:
<223> OTHER INFORMATION: Primer

<400> SEQUENCE: 50 ggcccctgg aatcttaac                                                      19
```

<210> SEQ ID NO 51
<211> LENGTH: 21
<212> TYPE: DNA
<213> ORGANISM: Artificial
<220> FEATURE:
<223> OTHER INFORMATION: Primer

<400> SEQUENCE: 51
gaccctcctg gaatcttaac c                                      21

<210> SEQ ID NO 52
<211> LENGTH: 24
<212> TYPE: DNA
<213> ORGANISM: Artificial
<220> FEATURE:
<223> OTHER INFORMATION: Primer

<400> SEQUENCE: 52
ttccatctac ctagaagttc ctca                                   24

<210> SEQ ID NO 53
<211> LENGTH: 24
<212> TYPE: DNA
<213> ORGANISM: Artificial
<220> FEATURE:
<223> OTHER INFORMATION: Primer

<400> SEQUENCE: 53
cgagaaggca attttctact tagg                                   24

<210> SEQ ID NO 54
<211> LENGTH: 23
<212> TYPE: DNA
<213> ORGANISM: Artificial
<220> FEATURE:
<223> OTHER INFORMATION: Primer

<400> SEQUENCE: 54
ttgacctaga gaaggcaatt ttc                                    23

<210> SEQ ID NO 55
<211> LENGTH: 20
<212> TYPE: DNA
<213> ORGANISM: Artificial
<220> FEATURE:
<223> OTHER INFORMATION: Primer

<400> SEQUENCE: 55
ccacctcatg aactcccact                                        20

<210> SEQ ID NO 56
<211> LENGTH: 18
<212> TYPE: DNA
<213> ORGANISM: Artificial
<220> FEATURE:
<223> OTHER INFORMATION: Primer

<400> SEQUENCE: 56
ccggcccgag aaggcaat                                          18

<210> SEQ ID NO 57
<211> LENGTH: 23
<212> TYPE: DNA
<213> ORGANISM: Artificial
<220> FEATURE:

```
<223> OTHER INFORMATION: Primer

<400> SEQUENCE: 57
gaccttgacc tagagaaggc aat                                              23

<210> SEQ ID NO 58
<211> LENGTH: 21
<212> TYPE: DNA
<213> ORGANISM: Artificial
<220> FEATURE:
<223> OTHER INFORMATION: Primer

<400> SEQUENCE: 58
caacgtcctc cctaactacc c                                                21

<210> SEQ ID NO 59
<211> LENGTH: 18
<212> TYPE: DNA
<213> ORGANISM: Artificial
<220> FEATURE:
<223> OTHER INFORMATION: Primer

<400> SEQUENCE: 59
ccggcccgag aaggcaat                                                    18

<210> SEQ ID NO 60
<211> LENGTH: 23
<212> TYPE: DNA
<213> ORGANISM: Artificial
<220> FEATURE:
<223> OTHER INFORMATION: Primer

<400> SEQUENCE: 60
gaccttgacc tagagaaggc aat                                              23

<210> SEQ ID NO 61
<211> LENGTH: 20
<212> TYPE: DNA
<213> ORGANISM: Artificial
<220> FEATURE:
<223> OTHER INFORMATION: Primer

<400> SEQUENCE: 61
cctgctctgc acacttcttg                                                  20

<210> SEQ ID NO 62
<211> LENGTH: 20
<212> TYPE: DNA
<213> ORGANISM: Artificial
<220> FEATURE:
<223> OTHER INFORMATION: Primer

<400> SEQUENCE: 62
cagctcagtc ctaagccaca                                                  20

<210> SEQ ID NO 63
<211> LENGTH: 19
<212> TYPE: DNA
<213> ORGANISM: Artificial
<220> FEATURE:
<223> OTHER INFORMATION: Primer

<400> SEQUENCE: 63
ccggcccagt ttcttaatg                                                   19
```

```
<210> SEQ ID NO 64
<211> LENGTH: 27
<212> TYPE: DNA
<213> ORGANISM: Artificial
<220> FEATURE:
<223> OTHER INFORMATION: Primer

<400> SEQUENCE: 64
catgaattca gtttcttaat gataagg                                              27

<210> SEQ ID NO 65
<211> LENGTH: 24
<212> TYPE: DNA
<213> ORGANISM: Artificial
<220> FEATURE:
<223> OTHER INFORMATION: Primer

<400> SEQUENCE: 65
agaagagtga atgcacattt atga                                                 24

<210> SEQ ID NO 66
<211> LENGTH: 19
<212> TYPE: DNA
<213> ORGANISM: Artificial
<220> FEATURE:
<223> OTHER INFORMATION: Primer

<400> SEQUENCE: 66
ccggcccagt ttcttaatg                                                       19

<210> SEQ ID NO 67
<211> LENGTH: 27
<212> TYPE: DNA
<213> ORGANISM: Artificial
<220> FEATURE:
<223> OTHER INFORMATION: Primer

<400> SEQUENCE: 67
catgaattca gtttcttaat gataagg                                              27

<210> SEQ ID NO 68
<211> LENGTH: 23
<212> TYPE: DNA
<213> ORGANISM: Artificial
<220> FEATURE:
<223> OTHER INFORMATION: Primer

<400> SEQUENCE: 68
cagtgaaagc ttcttagggg aat                                                  23

<210> SEQ ID NO 69
<211> LENGTH: 18
<212> TYPE: DNA
<213> ORGANISM: Artificial
<220> FEATURE:
<223> OTHER INFORMATION: Primer

<400> SEQUENCE: 69
ccggccctgt gtcttctt                                                        18

<210> SEQ ID NO 70
<211> LENGTH: 26
<212> TYPE: DNA
<213> ORGANISM: Artificial
<220> FEATURE:
<223> OTHER INFORMATION: Primer
```

```
<400> SEQUENCE: 70
tgtccttctg tgtcttctta aatatc                                          26

<210> SEQ ID NO 71
<211> LENGTH: 25
<212> TYPE: DNA
<213> ORGANISM: Artificial
<220> FEATURE:
<223> OTHER INFORMATION: Primer

<400> SEQUENCE: 71
gtacacatta agcacatgga agtca                                           25

<210> SEQ ID NO 72
<211> LENGTH: 18
<212> TYPE: DNA
<213> ORGANISM: Artificial
<220> FEATURE:
<223> OTHER INFORMATION: Primer

<400> SEQUENCE: 72
gcccggccgt tcttttc                                                    18

<210> SEQ ID NO 73
<211> LENGTH: 24
<212> TYPE: DNA
<213> ORGANISM: Artificial
<220> FEATURE:
<223> OTHER INFORMATION: Primer

<400> SEQUENCE: 73
gcatgaaatg ttcttttca tctc                                             24

<210> SEQ ID NO 74
<211> LENGTH: 20
<212> TYPE: DNA
<213> ORGANISM: Artificial
<220> FEATURE:
<223> OTHER INFORMATION: Primer

<400> SEQUENCE: 74
tcaaaacttg cggattttcc                                                 20

<210> SEQ ID NO 75
<211> LENGTH: 18
<212> TYPE: DNA
<213> ORGANISM: Artificial
<220> FEATURE:
<223> OTHER INFORMATION: Primer

<400> SEQUENCE: 75
gcgcaatctc ggctcctt                                                   18

<210> SEQ ID NO 76
<211> LENGTH: 22
<212> TYPE: DNA
<213> ORGANISM: Artificial
<220> FEATURE:
<223> OTHER INFORMATION: Primer

<400> SEQUENCE: 76
tgtgcagggg aattccttct aa                                              22

<210> SEQ ID NO 77
<211> LENGTH: 26
```

```
<210> SEQ ID NO 77
<211> LENGTH: 26
<212> TYPE: DNA
<213> ORGANISM: Artificial
<220> FEATURE:
<223> OTHER INFORMATION: Primer

<400> SEQUENCE: 77
tggaatacaa tgtaactggg gatatg                                            26

<210> SEQ ID NO 78
<211> LENGTH: 22
<212> TYPE: DNA
<213> ORGANISM: Artificial
<220> FEATURE:
<223> OTHER INFORMATION: Primer

<400> SEQUENCE: 78
ctggggatat tttcatagat gc                                                22

<210> SEQ ID NO 79
<211> LENGTH: 18
<212> TYPE: DNA
<213> ORGANISM: Artificial
<220> FEATURE:
<223> OTHER INFORMATION: Primer

<400> SEQUENCE: 79
gcccggccct cattattc                                                     18

<210> SEQ ID NO 80
<211> LENGTH: 26
<212> TYPE: DNA
<213> ORGANISM: Artificial
<220> FEATURE:
<223> OTHER INFORMATION: Primer

<400> SEQUENCE: 80
cccattctca ttattcttat tcaaca                                            26

<210> SEQ ID NO 81
<211> LENGTH: 24
<212> TYPE: DNA
<213> ORGANISM: Artificial
<220> FEATURE:
<223> OTHER INFORMATION: Primer

<400> SEQUENCE: 81
tgatgtcatg tacaaacagg gata                                              24

<210> SEQ ID NO 82
<211> LENGTH: 18
<212> TYPE: DNA
<213> ORGANISM: Artificial
<220> FEATURE:
<223> OTHER INFORMATION: Primer

<400> SEQUENCE: 82
gcccggccct cattattc                                                     18

<210> SEQ ID NO 83
<211> LENGTH: 27
<212> TYPE: DNA
<213> ORGANISM: Artificial
<220> FEATURE:
<223> OTHER INFORMATION: Primer

<400> SEQUENCE: 83
```

-continued caaggatacc cattctcatt attctta                                          27

<210> SEQ ID NO 84
<211> LENGTH: 20
<212> TYPE: DNA
<213> ORGANISM: Artificial
<220> FEATURE:
<223> OTHER INFORMATION: Primer

<400> SEQUENCE: 84
aagcccctga aaagtgaaat                                                  20

<210> SEQ ID NO 85
<211> LENGTH: 20
<212> TYPE: DNA
<213> ORGANISM: Artificial
<220> FEATURE:
<223> OTHER INFORMATION: Primer

<400> SEQUENCE: 85
ggagaggggt caaattctta                                                  20

<210> SEQ ID NO 86
<211> LENGTH: 27
<212> TYPE: DNA
<213> ORGANISM: Artificial
<220> FEATURE:
<223> OTHER INFORMATION: Primer

<400> SEQUENCE: 86
tttctggttc aaattcttat ctatcaa                                          27

<210> SEQ ID NO 87
<211> LENGTH: 21
<212> TYPE: DNA
<213> ORGANISM: Artificial
<220> FEATURE:
<223> OTHER INFORMATION: Primer

<400> SEQUENCE: 87
aaacaggaag catttcgagg t                                                21

<210> SEQ ID NO 88
<211> LENGTH: 18
<212> TYPE: DNA
<213> ORGANISM: Artificial
<220> FEATURE:
<223> OTHER INFORMATION: Primer

<400> SEQUENCE: 88
gcccagcctc acatagat                                                    18

<210> SEQ ID NO 89
<211> LENGTH: 23
<212> TYPE: DNA
<213> ORGANISM: Artificial
<220> FEATURE:
<223> OTHER INFORMATION: Primer

<400> SEQUENCE: 89
aaaaatggca catagatgtt gaa                                              23

<210> SEQ ID NO 90
<211> LENGTH: 20
<212> TYPE: DNA
<213> ORGANISM: Artificial

```
<220> FEATURE:
<223> OTHER INFORMATION: Primer

<400> SEQUENCE: 90
ccctgaatct gagtgggact                                           20

<210> SEQ ID NO 91
<211> LENGTH: 18
<212> TYPE: DNA
<213> ORGANISM: Artificial
<220> FEATURE:
<223> OTHER INFORMATION: Primer

<400> SEQUENCE: 91
ccggccggca cttttatg                                             18

<210> SEQ ID NO 92
<211> LENGTH: 20
<212> TYPE: DNA
<213> ORGANISM: Artificial
<220> FEATURE:
<223> OTHER INFORMATION: Primer

<400> SEQUENCE: 92
tgcatggcac ttttatgact                                           20

<210> SEQ ID NO 93
<211> LENGTH: 22
<212> TYPE: DNA
<213> ORGANISM: Artificial
<220> FEATURE:
<223> OTHER INFORMATION: Primer

<400> SEQUENCE: 93
cagaaatgca tggcactttt at                                        22

<210> SEQ ID NO 94
<211> LENGTH: 23
<212> TYPE: DNA
<213> ORGANISM: Artificial
<220> FEATURE:
<223> OTHER INFORMATION: Primer

<400> SEQUENCE: 94
ttcctctttt tctccatttt gtt                                       23

<210> SEQ ID NO 95
<211> LENGTH: 20
<212> TYPE: DNA
<213> ORGANISM: Artificial
<220> FEATURE:
<223> OTHER INFORMATION: Primer

<400> SEQUENCE: 95
ggcctcccaa ggattcttta                                           20

<210> SEQ ID NO 96
<211> LENGTH: 20
<212> TYPE: DNA
<213> ORGANISM: Artificial
<220> FEATURE:
<223> OTHER INFORMATION: Primer

<400> SEQUENCE: 96
ccttgcttgg ggattcttta                                           20
```

```
<210> SEQ ID NO 97
<211> LENGTH: 22
<212> TYPE: DNA
<213> ORGANISM: Artificial
<220> FEATURE:
<223> OTHER INFORMATION: Primer

<400> SEQUENCE: 97
ggtgtagcag aacagacagg ag                                              22

<210> SEQ ID NO 98
<211> LENGTH: 20
<212> TYPE: DNA
<213> ORGANISM: Artificial
<220> FEATURE:
<223> OTHER INFORMATION: Primer

<400> SEQUENCE: 98
aagtgctggc tgttcaccac                                                 20

<210> SEQ ID NO 99
<211> LENGTH: 21
<212> TYPE: DNA
<213> ORGANISM: Artificial
<220> FEATURE:
<223> OTHER INFORMATION: Primer

<400> SEQUENCE: 99
ggtttctgtt caccactttc a                                               21

<210> SEQ ID NO 100
<211> LENGTH: 22
<212> TYPE: DNA
<213> ORGANISM: Artificial
<220> FEATURE:
<223> OTHER INFORMATION: Primer

<400> SEQUENCE: 100
tagcagaaca gacaggagac ca                                              22

<210> SEQ ID NO 101
<211> LENGTH: 20
<212> TYPE: DNA
<213> ORGANISM: Artificial
<220> FEATURE:
<223> OTHER INFORMATION: Primer

<400> SEQUENCE: 101
ttggggtttc tgttcaccac                                                 20

<210> SEQ ID NO 102
<211> LENGTH: 22
<212> TYPE: DNA
<213> ORGANISM: Artificial
<220> FEATURE:
<223> OTHER INFORMATION: Primer

<400> SEQUENCE: 102
ggtgtagcag aacagacagg ag                                              22

<210> SEQ ID NO 103
<211> LENGTH: 20
<212> TYPE: DNA
<213> ORGANISM: Artificial
<220> FEATURE:
<223> OTHER INFORMATION: Primer
```

<400> SEQUENCE: 103
aagtgctggc tgttcaccac                                              20

<210> SEQ ID NO 104
<211> LENGTH: 21
<212> TYPE: DNA
<213> ORGANISM: Artificial
<220> FEATURE:
<223> OTHER INFORMATION: Primer

<400> SEQUENCE: 104
ggtttctgtt caccactttc a                                            21

<210> SEQ ID NO 105
<211> LENGTH: 20
<212> TYPE: DNA
<213> ORGANISM: Artificial
<220> FEATURE:
<223> OTHER INFORMATION: Primer

<400> SEQUENCE: 105
acagctgggc aatacgttct                                              20

<210> SEQ ID NO 106
<211> LENGTH: 19
<212> TYPE: DNA
<213> ORGANISM: Artificial
<220> FEATURE:
<223> OTHER INFORMATION: Primer

<400> SEQUENCE: 106
ccggccaaga ttttcattt                                               19

<210> SEQ ID NO 107
<211> LENGTH: 24
<212> TYPE: DNA
<213> ORGANISM: Artificial
<220> FEATURE:
<223> OTHER INFORMATION: Primer

<400> SEQUENCE: 107
gagccaaaga ttttcatttt gatg                                         24

<210> SEQ ID NO 108
<211> LENGTH: 22
<212> TYPE: DNA
<213> ORGANISM: Artificial
<220> FEATURE:
<223> OTHER INFORMATION: Primer

<400> SEQUENCE: 108
cagagccaaa gattttcatt tt                                           22

<210> SEQ ID NO 109
<211> LENGTH: 20
<212> TYPE: DNA
<213> ORGANISM: Artificial
<220> FEATURE:
<223> OTHER INFORMATION: Primer

<400> SEQUENCE: 109
ttgcagaatg ggtttggaag                                              20

<210> SEQ ID NO 110

<211> LENGTH: 18
<212> TYPE: DNA
<213> ORGANISM: Artificial
<220> FEATURE:
<223> OTHER INFORMATION: Primer

<400> SEQUENCE: 110
ccggccttta ccaaactt                                                 18

<210> SEQ ID NO 111
<211> LENGTH: 27
<212> TYPE: DNA
<213> ORGANISM: Artificial
<220> FEATURE:
<223> OTHER INFORMATION: Primer

<400> SEQUENCE: 111
gctgaacttt accaaacttt taaagaa                                       27

<210> SEQ ID NO 112
<211> LENGTH: 23
<212> TYPE: DNA
<213> ORGANISM: Artificial
<220> FEATURE:
<223> OTHER INFORMATION: Primer

<400> SEQUENCE: 112
agaaggaaga agctccaaac gtg                                           23

<210> SEQ ID NO 113
<211> LENGTH: 18
<212> TYPE: DNA
<213> ORGANISM: Artificial
<220> FEATURE:
<223> OTHER INFORMATION: Primer

<400> SEQUENCE: 113
ctcctgcgtg gcttcatt                                                 18

<210> SEQ ID NO 114
<211> LENGTH: 24
<212> TYPE: DNA
<213> ORGANISM: Artificial
<220> FEATURE:
<223> OTHER INFORMATION: Primer

<400> SEQUENCE: 114
tgacttggct tcattcttcg gtga                                          24

<210> SEQ ID NO 115
<211> LENGTH: 22
<212> TYPE: DNA
<213> ORGANISM: Artificial
<220> FEATURE:
<223> OTHER INFORMATION: Primer

<400> SEQUENCE: 115
actgacttgg cttcattctt cg                                            22

<210> SEQ ID NO 116
<211> LENGTH: 24
<212> TYPE: DNA
<213> ORGANISM: Artificial
<220> FEATURE:
<223> OTHER INFORMATION: Primer

<400> SEQUENCE: 116
ttaagaaagt cagcagaaaa cttc                                  24

<210> SEQ ID NO 117
<211> LENGTH: 18
<212> TYPE: DNA
<213> ORGANISM: Artificial
<220> FEATURE:
<223> OTHER INFORMATION: Primer

<400> SEQUENCE: 117
cccggcccag attttact                                         18

<210> SEQ ID NO 118
<211> LENGTH: 27
<212> TYPE: DNA
<213> ORGANISM: Artificial
<220> FEATURE:
<223> OTHER INFORMATION: Primer

<400> SEQUENCE: 118
ggtcttacag attttacttt tatttgc                               27

<210> SEQ ID NO 119
<211> LENGTH: 20
<212> TYPE: DNA
<213> ORGANISM: Artificial
<220> FEATURE:
<223> OTHER INFORMATION: Primer

<400> SEQUENCE: 119
acagaggcca ccctgtaggt                                       20

<210> SEQ ID NO 120
<211> LENGTH: 18
<212> TYPE: DNA
<213> ORGANISM: Artificial
<220> FEATURE:
<223> OTHER INFORMATION: Primer

<400> SEQUENCE: 120
acctggcctg ggtgactg                                         18

<210> SEQ ID NO 121
<211> LENGTH: 22
<212> TYPE: DNA
<213> ORGANISM: Artificial
<220> FEATURE:
<223> OTHER INFORMATION: Primer

<400> SEQUENCE: 121
tgagactggg tgactgtgtt tt                                    22

<210> SEQ ID NO 122
<211> LENGTH: 22
<212> TYPE: DNA
<213> ORGANISM: Artificial
<220> FEATURE:
<223> OTHER INFORMATION: Primer

<400> SEQUENCE: 122
tgaaatgaga ctgggtgact gt                                    22

<210> SEQ ID NO 123
<211> LENGTH: 20
<212> TYPE: DNA

<210> SEQ ID NO 123
<211> LENGTH: 20
<212> TYPE: DNA
<213> ORGANISM: Artificial
<220> FEATURE:
<223> OTHER INFORMATION: Primer

<400> SEQUENCE: 123
aaagctgggt ttccttttgc                                                    20

<210> SEQ ID NO 124
<211> LENGTH: 19
<212> TYPE: DNA
<213> ORGANISM: Artificial
<220> FEATURE:
<223> OTHER INFORMATION: Primer

<400> SEQUENCE: 124
gctggccgga agtcttaat                                                     19

<210> SEQ ID NO 125
<211> LENGTH: 24
<212> TYPE: DNA
<213> ORGANISM: Artificial
<220> FEATURE:
<223> OTHER INFORMATION: Primer

<400> SEQUENCE: 125
tgaaggatag aagtcttaat gcag                                               24

<210> SEQ ID NO 126
<211> LENGTH: 23
<212> TYPE: DNA
<213> ORGANISM: Artificial
<220> FEATURE:
<223> OTHER INFORMATION: Primer

<400> SEQUENCE: 126
cccaataaaa tcagcaaata tga                                                23

<210> SEQ ID NO 127
<211> LENGTH: 18
<212> TYPE: DNA
<213> ORGANISM: Artificial
<220> FEATURE:
<223> OTHER INFORMATION: Primer

<400> SEQUENCE: 127
ccggccccca catttctt                                                      18

<210> SEQ ID NO 128
<211> LENGTH: 25
<212> TYPE: DNA
<213> ORGANISM: Artificial
<220> FEATURE:
<223> OTHER INFORMATION: Primer

<400> SEQUENCE: 128 tgactttcc acatttctta cattg                                               25

<210> SEQ ID NO 129
<211> LENGTH: 21
<212> TYPE: DNA
<213> ORGANISM: Artificial
<220> FEATURE:
<223> OTHER INFORMATION: Primer

<400> SEQUENCE: 129
tgctgccctt aatctttacc a                                                  21

```
<210> SEQ ID NO 130
<211> LENGTH: 19
<212> TYPE: DNA
<213> ORGANISM: Artificial
<220> FEATURE:
<223> OTHER INFORMATION: Primer

<400> SEQUENCE: 130
cccggccttc atttctaag                                         19

<210> SEQ ID NO 131
<211> LENGTH: 27
<212> TYPE: DNA
<213> ORGANISM: Artificial
<220> FEATURE:
<223> OTHER INFORMATION: Primer

<400> SEQUENCE: 131
ataagagact ttcatttcta agatgtc                                27

<210> SEQ ID NO 132
<211> LENGTH: 22
<212> TYPE: DNA
<213> ORGANISM: Artificial
<220> FEATURE:
<223> OTHER INFORMATION: Primer

<400> SEQUENCE: 132
ccattaaagg aacaagaatg ga                                     22

<210> SEQ ID NO 133
<211> LENGTH: 19
<212> TYPE: DNA
<213> ORGANISM: Artificial
<220> FEATURE:
<223> OTHER INFORMATION: Primer

<400> SEQUENCE: 133
gcccggccag taatcttta                                         19

<210> SEQ ID NO 134
<211> LENGTH: 25
<212> TYPE: DNA
<213> ORGANISM: Artificial
<220> FEATURE:
<223> OTHER INFORMATION: Primer

<400> SEQUENCE: 134
ctggtccagt aatctttaat acact                                  25

<210> SEQ ID NO 135
<211> LENGTH: 21
<212> TYPE: DNA
<213> ORGANISM: Artificial
<220> FEATURE:
<223> OTHER INFORMATION: Primer

<400> SEQUENCE: 135
gtttacctgc cttctggctc t                                      21

<210> SEQ ID NO 136
<211> LENGTH: 19
<212> TYPE: DNA
<213> ORGANISM: Artificial
<220> FEATURE:
```

```
<223> OTHER INFORMATION: Primer

<400> SEQUENCE: 136
gcccagccta ctcttgtta                                                   19

<210> SEQ ID NO 137
<211> LENGTH: 27
<212> TYPE: DNA
<213> ORGANISM: Artificial
<220> FEATURE:
<223> OTHER INFORMATION: Primer

<400> SEQUENCE: 137
attacctcta ctcttgttaa ccaacca                                          27

<210> SEQ ID NO 138
<211> LENGTH: 26
<212> TYPE: DNA
<213> ORGANISM: Artificial
<220> FEATURE:
<223> OTHER INFORMATION: Primer

<400> SEQUENCE: 138
tttcttagtt ctttaacaac agatgc                                           26

<210> SEQ ID NO 139
<211> LENGTH: 23
<212> TYPE: DNA
<213> ORGANISM: Artificial
<220> FEATURE:
<223> OTHER INFORMATION: Primer

<400> SEQUENCE: 139
tatccttgct agaagttact gga                                              23

<210> SEQ ID NO 140
<211> LENGTH: 23
<212> TYPE: DNA
<213> ORGANISM: Artificial
<220> FEATURE:
<223> OTHER INFORMATION: Primer

<400> SEQUENCE: 140
attccaaaaa gaagttactg gat                                              23

<210> SEQ ID NO 141
<211> LENGTH: 23
<212> TYPE: DNA
<213> ORGANISM: Artificial
<220> FEATURE:
<223> OTHER INFORMATION: Primer

<400> SEQUENCE: 141
aatacagcca aatgaactgg aga                                              23

<210> SEQ ID NO 142
<211> LENGTH: 22
<212> TYPE: DNA
<213> ORGANISM: Artificial
<220> FEATURE:
<223> OTHER INFORMATION: Primer

<400> SEQUENCE: 142
tctggcctcc atttagtatt tt                                               22
```

<210> SEQ ID NO 143
<211> LENGTH: 25
<212> TYPE: DNA
<213> ORGANISM: Artificial
<220> FEATURE:
<223> OTHER INFORMATION: Primer

<400> SEQUENCE: 143
gcactctcta tttagtattt tctcg                                           25

<210> SEQ ID NO 144
<211> LENGTH: 22
<212> TYPE: DNA
<213> ORGANISM: Artificial
<220> FEATURE:
<223> OTHER INFORMATION: Primer

<400> SEQUENCE: 144
tgcacacgta tgtttattgc ag                                              22

<210> SEQ ID NO 145
<211> LENGTH: 20
<212> TYPE: DNA
<213> ORGANISM: Artificial
<220> FEATURE:
<223> OTHER INFORMATION: Primer

<400> SEQUENCE: 145
tcctcccctc cattttctta                                                 20

<210> SEQ ID NO 146
<211> LENGTH: 26
<212> TYPE: DNA
<213> ORGANISM: Artificial
<220> FEATURE:
<223> OTHER INFORMATION: Primer

<400> SEQUENCE: 146
atatatgcca ttttcttaat ccagtc                                          26

<210> SEQ ID NO 147
<211> LENGTH: 22
<212> TYPE: DNA
<213> ORGANISM: Artificial
<220> FEATURE:
<223> OTHER INFORMATION: Primer

<400> SEQUENCE: 147
taatatgagg tgatgggggt ta                                              22

<210> SEQ ID NO 148
<211> LENGTH: 18
<212> TYPE: DNA
<213> ORGANISM: Artificial
<220> FEATURE:
<223> OTHER INFORMATION: Primer

<400> SEQUENCE: 148
ccggccgcca gtttctta                                                   18

<210> SEQ ID NO 149
<211> LENGTH: 24
<212> TYPE: DNA
<213> ORGANISM: Artificial
<220> FEATURE:
<223> OTHER INFORMATION: Primer

<400> SEQUENCE: 149
cccagaacca gtttcttaaa tagc                                          24

<210> SEQ ID NO 150
<211> LENGTH: 27
<212> TYPE: DNA
<213> ORGANISM: Artificial
<220> FEATURE:
<223> OTHER INFORMATION: Primer

<400> SEQUENCE: 150
tcttgataac atagggaaaa tcacttc                                       27

<210> SEQ ID NO 151
<211> LENGTH: 19
<212> TYPE: DNA
<213> ORGANISM: Artificial
<220> FEATURE:
<223> OTHER INFORMATION: Primer

<400> SEQUENCE: 151
ccggcccaga gttcttaat                                                19

<210> SEQ ID NO 152
<211> LENGTH: 27
<212> TYPE: DNA
<213> ORGANISM: Artificial
<220> FEATURE:
<223> OTHER INFORMATION: Primer

<400> SEQUENCE: 152
tgttttgtac agagttctta attgcag                                       27

<210> SEQ ID NO 153
<211> LENGTH: 21
<212> TYPE: DNA
<213> ORGANISM: Artificial
<220> FEATURE:
<223> OTHER INFORMATION: Primer

<400> SEQUENCE: 153
ggctagccat atggagaaga a                                             21

<210> SEQ ID NO 154
<211> LENGTH: 19
<212> TYPE: DNA
<213> ORGANISM: Artificial
<220> FEATURE:
<223> OTHER INFORMATION: Primer

<400> SEQUENCE: 154
ccggccggaa ttcttatag                                                19

<210> SEQ ID NO 155
<211> LENGTH: 27
<212> TYPE: DNA
<213> ORGANISM: Artificial
<220> FEATURE:
<223> OTHER INFORMATION: Primer

<400> SEQUENCE: 155
ttcttctgga attcttatag tttgagg                                       27

<210> SEQ ID NO 156
<211> LENGTH: 19

```
<212> TYPE: DNA
<213> ORGANISM: Artificial
<220> FEATURE:
<223> OTHER INFORMATION: Primer

<400> SEQUENCE: 156
agcttgaggg tggctgtgt                                              19

<210> SEQ ID NO 157
<211> LENGTH: 20
<212> TYPE: DNA
<213> ORGANISM: Artificial
<220> FEATURE:
<223> OTHER INFORMATION: Primer

<400> SEQUENCE: 157
gctcacgctc tgtgagtgtt                                             20

<210> SEQ ID NO 158
<211> LENGTH: 27
<212> TYPE: DNA
<213> ORGANISM: Artificial
<220> FEATURE:
<223> OTHER INFORMATION: Primer

<400> SEQUENCE: 158
agagagattt gtgagtgttt aaagatg                                     27

<210> SEQ ID NO 159
<211> LENGTH: 21
<212> TYPE: DNA
<213> ORGANISM: Artificial
<220> FEATURE:
<223> OTHER INFORMATION: Primer

<400> SEQUENCE: 159
ttttcggttg tgaactgaag g                                           21

<210> SEQ ID NO 160
<211> LENGTH: 20
<212> TYPE: DNA
<213> ORGANISM: Artificial
<220> FEATURE:
<223> OTHER INFORMATION: Primer

<400> SEQUENCE: 160
cccagcctta aactgaccat                                             20

<210> SEQ ID NO 161
<211> LENGTH: 21
<212> TYPE: DNA
<213> ORGANISM: Artificial
<220> FEATURE:
<223> OTHER INFORMATION: Primer

<400> SEQUENCE: 161
gcccctaaac tgaccattct t                                           21

<210> SEQ ID NO 162
<211> LENGTH: 20
<212> TYPE: DNA
<213> ORGANISM: Artificial
<220> FEATURE:
<223> OTHER INFORMATION: Primer

<400> SEQUENCE: 162
``` ccagcccta aactgaccat        20

<210> SEQ ID NO 163
<211> LENGTH: 22
<212> TYPE: DNA
<213> ORGANISM: Artificial
<220> FEATURE:
<223> OTHER INFORMATION: Primer

<400> SEQUENCE: 163
aagacccaaa ttagcgaaag aa        22

<210> SEQ ID NO 164
<211> LENGTH: 23
<212> TYPE: DNA
<213> ORGANISM: Artificial
<220> FEATURE:
<223> OTHER INFORMATION: Primer

<400> SEQUENCE: 164
aaacctaggc attaccttt caa        23

<210> SEQ ID NO 165
<211> LENGTH: 22
<212> TYPE: DNA
<213> ORGANISM: Artificial
<220> FEATURE:
<223> OTHER INFORMATION: Primer

<400> SEQUENCE: 165
catttgtcgt ttaccttttc aa        22

<210> SEQ ID NO 166
<211> LENGTH: 25
<212> TYPE: DNA
<213> ORGANISM: Artificial
<220> FEATURE:
<223> OTHER INFORMATION: Primer

<400> SEQUENCE: 166
ctctatatgc actacagttt tgtga        25

<210> SEQ ID NO 167
<211> LENGTH: 18
<212> TYPE: DNA
<213> ORGANISM: Artificial
<220> FEATURE:
<223> OTHER INFORMATION: Primer

<400> SEQUENCE: 167
ccggccccaa gtgtttta        18

<210> SEQ ID NO 168
<211> LENGTH: 22
<212> TYPE: DNA
<213> ORGANISM: Artificial
<220> FEATURE:
<223> OTHER INFORMATION: Primer

<400> SEQUENCE: 168
ccccagaatt accaagtgtt tt        22

<210> SEQ ID NO 169
<211> LENGTH: 20
<212> TYPE: DNA
<213> ORGANISM: Artificial

```
<220> FEATURE:
<223> OTHER INFORMATION: Primer

<400> SEQUENCE: 169
gaacatccag caccaaatcc                                              20

<210> SEQ ID NO 170
<211> LENGTH: 18
<212> TYPE: DNA
<213> ORGANISM: Artificial
<220> FEATURE:
<223> OTHER INFORMATION: Primer

<400> SEQUENCE: 170
cccggcccta ccttctta                                                18

<210> SEQ ID NO 171
<211> LENGTH: 22
<212> TYPE: DNA
<213> ORGANISM: Artificial
<220> FEATURE:
<223> OTHER INFORMATION: Primer

<400> SEQUENCE: 171
cctggttgtg tgttaccttc tt                                           22

<210> SEQ ID NO 172
<211> LENGTH: 20
<212> TYPE: DNA
<213> ORGANISM: Artificial
<220> FEATURE:
<223> OTHER INFORMATION: Primer

<400> SEQUENCE: 172
aggcaggcag atcacttgag                                              20

<210> SEQ ID NO 173
<211> LENGTH: 19
<212> TYPE: DNA
<213> ORGANISM: Artificial
<220> FEATURE:
<223> OTHER INFORMATION: Primer

<400> SEQUENCE: 173 cgcgcccta attctttct                                                19

<210> SEQ ID NO 174
<211> LENGTH: 21
<212> TYPE: DNA
<213> ORGANISM: Artificial
<220> FEATURE:
<223> OTHER INFORMATION: Primer

<400> SEQUENCE: 174
ccatgcctgg ctaattcttt c                                            21

<210> SEQ ID NO 175
<211> LENGTH: 20
<212> TYPE: DNA
<213> ORGANISM: Artificial
<220> FEATURE:
<223> OTHER INFORMATION: Primer

<400> SEQUENCE: 175 aggggggtgag ggataaaaga                                             20
```

<210> SEQ ID NO 176
<211> LENGTH: 21
<212> TYPE: DNA
<213> ORGANISM: Artificial
<220> FEATURE:
<223> OTHER INFORMATION: Primer

<400> SEQUENCE: 176
tgagccaccg atgaataagt t                                              21

<210> SEQ ID NO 177
<211> LENGTH: 26
<212> TYPE: DNA
<213> ORGANISM: Artificial
<220> FEATURE:
<223> OTHER INFORMATION: Primer

<400> SEQUENCE: 177
ggtatttggt tacatgaata agttct                                         26

<210> SEQ ID NO 178
<211> LENGTH: 24
<212> TYPE: DNA
<213> ORGANISM: Artificial
<220> FEATURE:
<223> OTHER INFORMATION: Primer

<400> SEQUENCE: 178
gagcacatta cctataggca gaca                                           24

<210> SEQ ID NO 179
<211> LENGTH: 20
<212> TYPE: DNA
<213> ORGANISM: Artificial
<220> FEATURE:
<223> OTHER INFORMATION: Primer

<400> SEQUENCE: 179
gcccggcctt attttagttt                                                20

<210> SEQ ID NO 180
<211> LENGTH: 27
<212> TYPE: DNA
<213> ORGANISM: Artificial
<220> FEATURE:
<223> OTHER INFORMATION: Primer

<400> SEQUENCE: 180
tgggttgata gttattttat tttagtt                                        27

<210> SEQ ID NO 181
<211> LENGTH: 24
<212> TYPE: DNA
<213> ORGANISM: Artificial
<220> FEATURE:
<223> OTHER INFORMATION: Primer

<400> SEQUENCE: 181
gggattggat agaatgaaga aagg                                           24

<210> SEQ ID NO 182
<211> LENGTH: 19
<212> TYPE: DNA
<213> ORGANISM: Artificial
<220> FEATURE:
<223> OTHER INFORMATION: Primer

<400> SEQUENCE: 182
gcccggcctc tctctttag                                                    19

<210> SEQ ID NO 183
<211> LENGTH: 22
<212> TYPE: DNA
<213> ORGANISM: Artificial
<220> FEATURE:
<223> OTHER INFORMATION: Primer

<400> SEQUENCE: 183
cgcgctctct ctctctcttt ag                                                22

<210> SEQ ID NO 184
<211> LENGTH: 24
<212> TYPE: DNA
<213> ORGANISM: Artificial
<220> FEATURE:
<223> OTHER INFORMATION: Primer

<400> SEQUENCE: 184
agaagagtga atgcacattt atga                                              24

<210> SEQ ID NO 185
<211> LENGTH: 19
<212> TYPE: DNA
<213> ORGANISM: Artificial
<220> FEATURE:
<223> OTHER INFORMATION: Primer

<400> SEQUENCE: 185
cccggcccag tttcttaat                                                    19

<210> SEQ ID NO 186
<211> LENGTH: 24
<212> TYPE: DNA
<213> ORGANISM: Artificial
<220> FEATURE:
<223> OTHER INFORMATION: Primer

<400> SEQUENCE: 186
gggagtcatg aattcagttt ctta                                              24

<210> SEQ ID NO 187
<211> LENGTH: 25
<212> TYPE: DNA
<213> ORGANISM: Artificial
<220> FEATURE:
<223> OTHER INFORMATION: Primer

<400> SEQUENCE: 187
tcctactctc atttcttcac attca                                             25

<210> SEQ ID NO 188
<211> LENGTH: 26
<212> TYPE: DNA
<213> ORGANISM: Artificial
<220> FEATURE:
<223> OTHER INFORMATION: Primer

<400> SEQUENCE: 188
cttgtaaatt tgtcttgagt tcattg                                            26

<210> SEQ ID NO 189

<211> LENGTH: 21
<212> TYPE: DNA
<213> ORGANISM: Artificial
<220> FEATURE:
<223> OTHER INFORMATION: Primer

<400> SEQUENCE: 189
ggctgtgtgc tttttgagtt c         21

<210> SEQ ID NO 190
<211> LENGTH: 22
<212> TYPE: DNA
<213> ORGANISM: Artificial
<220> FEATURE:
<223> OTHER INFORMATION: Primer

<400> SEQUENCE: 190
gggaggacat tgaaggtaaa ca        22

<210> SEQ ID NO 191
<211> LENGTH: 20
<212> TYPE: DNA
<213> ORGANISM: Artificial
<220> FEATURE:
<223> OTHER INFORMATION: Primer

<400> SEQUENCE: 191
acctggctga ttgcagtttt           20

<210> SEQ ID NO 192
<211> LENGTH: 19
<212> TYPE: DNA
<213> ORGANISM: Artificial
<220> FEATURE:
<223> OTHER INFORMATION: Primer

<400> SEQUENCE: 192
gggccatttg attgcagtt            19

<210> SEQ ID NO 193
<211> LENGTH: 20
<212> TYPE: DNA
<213> ORGANISM: Artificial
<220> FEATURE:
<223> OTHER INFORMATION: Primer

<400> SEQUENCE: 193
gaggctgcag tgagctatga           20

<210> SEQ ID NO 194
<211> LENGTH: 18
<212> TYPE: DNA
<213> ORGANISM: Artificial
<220> FEATURE:
<223> OTHER INFORMATION: Primer

<400> SEQUENCE: 194
gcccggccaa tttacagc             18

<210> SEQ ID NO 195
<211> LENGTH: 25
<212> TYPE: DNA
<213> ORGANISM: Artificial
<220> FEATURE:
<223> OTHER INFORMATION: Primer

<400> SEQUENCE: 195
aagaactcat tcagaaattt acagc                                     25

<210> SEQ ID NO 196
<211> LENGTH: 20
<212> TYPE: DNA
<213> ORGANISM: Artificial
<220> FEATURE:
<223> OTHER INFORMATION: Primer

<400> SEQUENCE: 196
tagagtgctg ctgtggcaaa                                           20

<210> SEQ ID NO 197
<211> LENGTH: 19
<212> TYPE: DNA
<213> ORGANISM: Artificial
<220> FEATURE:
<223> OTHER INFORMATION: Primer

<400> SEQUENCE: 197
gcccagccta gtgtcctct                                            19

<210> SEQ ID NO 198
<211> LENGTH: 25
<212> TYPE: DNA
<213> ORGANISM: Artificial
<220> FEATURE:
<223> OTHER INFORMATION: Primer

<400> SEQUENCE: 198
ttctcctggt tactagtgtc ctctc                                     25

<210> SEQ ID NO 199
<211> LENGTH: 23
<212> TYPE: DNA
<213> ORGANISM: Artificial
<220> FEATURE:
<223> OTHER INFORMATION: Primer

<400> SEQUENCE: 199
ccaagtcagg tataagcctc aga                                       23

<210> SEQ ID NO 200
<211> LENGTH: 20
<212> TYPE: DNA
<213> ORGANISM: Artificial
<220> FEATURE:
<223> OTHER INFORMATION: Primer

<400> SEQUENCE: 200
gccggatgtc cactcttaaa                                           20

<210> SEQ ID NO 201
<211> LENGTH: 22
<212> TYPE: DNA
<213> ORGANISM: Artificial
<220> FEATURE:
<223> OTHER INFORMATION: Primer

<400> SEQUENCE: 201
acagaaagga tgtccactct ta                                        22

<210> SEQ ID NO 202
<211> LENGTH: 20
<212> TYPE: DNA

```
<213> ORGANISM: Artificial
<220> FEATURE:
<223> OTHER INFORMATION: Primer

<400> SEQUENCE: 202
caggcctggt ggtaacaaat                                               20

<210> SEQ ID NO 203
<211> LENGTH: 18
<212> TYPE: DNA
<213> ORGANISM: Artificial
<220> FEATURE:
<223> OTHER INFORMATION: Primer

<400> SEQUENCE: 203
ctcggcctcc caatcaac                                                 18

<210> SEQ ID NO 204
<211> LENGTH: 21
<212> TYPE: DNA
<213> ORGANISM: Artificial
<220> FEATURE:
<223> OTHER INFORMATION: Primer

<400> SEQUENCE: 204
ggccaatatt caacattctt a                                             21

<210> SEQ ID NO 205
<211> LENGTH: 21
<212> TYPE: DNA
<213> ORGANISM: Artificial
<220> FEATURE:
<223> OTHER INFORMATION: Primer

<400> SEQUENCE: 205
ccctggactt accctatctc a                                             21

<210> SEQ ID NO 206
<211> LENGTH: 21
<212> TYPE: DNA
<213> ORGANISM: Artificial
<220> FEATURE:
<223> OTHER INFORMATION: Primer

<400> SEQUENCE: 206
tgctgggatt acatggattt t                                             21

<210> SEQ ID NO 207
<211> LENGTH: 24
<212> TYPE: DNA
<213> ORGANISM: Artificial
<220> FEATURE:
<223> OTHER INFORMATION: Primer

<400> SEQUENCE: 207
ggagaatgtg tgtggatttt attc                                          24

<210> SEQ ID NO 208
<211> LENGTH: 20
<212> TYPE: DNA
<213> ORGANISM: Artificial
<220> FEATURE:
<223> OTHER INFORMATION: Primer

<400> SEQUENCE: 208
ctttggccct gagagagatg                                               20
```

<210> SEQ ID NO 209
<211> LENGTH: 20
<212> TYPE: DNA
<213> ORGANISM: Artificial
<220> FEATURE:
<223> OTHER INFORMATION: Primer

<400> SEQUENCE: 209
acaccccacc aaaactgaat                                               20

<210> SEQ ID NO 210
<211> LENGTH: 20
<212> TYPE: DNA
<213> ORGANISM: Artificial
<220> FEATURE:
<223> OTHER INFORMATION: Primer

<400> SEQUENCE: 210
ttttaaaacc gaatgccttt                                               20

<210> SEQ ID NO 211
<211> LENGTH: 20
<212> TYPE: DNA
<213> ORGANISM: Artificial
<220> FEATURE:
<223> OTHER INFORMATION: Primer

<400> SEQUENCE: 211
agcagctctg ggtgtagcag                                               20

<210> SEQ ID NO 212
<211> LENGTH: 19
<212> TYPE: DNA
<213> ORGANISM: Artificial
<220> FEATURE:
<223> OTHER INFORMATION: Primer

<400> SEQUENCE: 212
ccaaagtgct ggctgttca                                                19

<210> SEQ ID NO 213
<211> LENGTH: 20
<212> TYPE: DNA
<213> ORGANISM: Artificial
<220> FEATURE:
<223> OTHER INFORMATION: Primer

<400> SEQUENCE: 213
tggggtttct gttcaccact                                               20

<210> SEQ ID NO 214
<211> LENGTH: 20
<212> TYPE: DNA
<213> ORGANISM: Artificial
<220> FEATURE:
<223> OTHER INFORMATION: Primer

<400> SEQUENCE: 214
acagctgggc aatacgttct                                               20

<210> SEQ ID NO 215
<211> LENGTH: 18
<212> TYPE: DNA
<213> ORGANISM: Artificial
<220> FEATURE:

-continued

<223> OTHER INFORMATION: Primer

<400> SEQUENCE: 215
cgcccggcca agatttttc                                                  18

<210> SEQ ID NO 216
<211> LENGTH: 22
<212> TYPE: DNA
<213> ORGANISM: Artificial
<220> FEATURE:
<223> OTHER INFORMATION: Primer

<400> SEQUENCE: 216
cagagccaaa gattttcatt tt                                              22

<210> SEQ ID NO 217
<211> LENGTH: 24
<212> TYPE: DNA
<213> ORGANISM: Artificial
<220> FEATURE:
<223> OTHER INFORMATION: Primer

<400> SEQUENCE: 217
tctttcctct ttttctccat tttg                                            24

<210> SEQ ID NO 218
<211> LENGTH: 18
<212> TYPE: DNA
<213> ORGANISM: Artificial
<220> FEATURE:
<223> OTHER INFORMATION: Primer

<400> SEQUENCE: 218
ctcggcctcc caaggatt                                                   18

<210> SEQ ID NO 219
<211> LENGTH: 20
<212> TYPE: DNA
<213> ORGANISM: Artificial
<220> FEATURE:
<223> OTHER INFORMATION: Primer

<400> SEQUENCE: 219
ccttgcttgg ggattcttta                                                 20

<210> SEQ ID NO 220
<211> LENGTH: 20
<212> TYPE: DNA
<213> ORGANISM: Artificial
<220> FEATURE:
<223> OTHER INFORMATION: Primer

<400> SEQUENCE: 220
gtctgcagct tcactcctga                                                 20

<210> SEQ ID NO 221
<211> LENGTH: 19
<212> TYPE: DNA
<213> ORGANISM: Artificial
<220> FEATURE:
<223> OTHER INFORMATION: Primer

<400> SEQUENCE: 221
cattctcctg cgtggcttc                                                  19

<210> SEQ ID NO 222
<211> LENGTH: 20
<212> TYPE: DNA
<213> ORGANISM: Artificial
<220> FEATURE:
<223> OTHER INFORMATION: Primer

<400> SEQUENCE: 222
tgacttggct tcattcttcg                                              20

<210> SEQ ID NO 223
<211> LENGTH: 20
<212> TYPE: DNA
<213> ORGANISM: Artificial
<220> FEATURE:
<223> OTHER INFORMATION: Primer

<400> SEQUENCE: 223
caggagaaca tggccttcac                                              20

<210> SEQ ID NO 224
<211> LENGTH: 18
<212> TYPE: DNA
<213> ORGANISM: Artificial
<220> FEATURE:
<223> OTHER INFORMATION: Primer

<400> SEQUENCE: 224
cgcccagcct atccttt                                                 18

<210> SEQ ID NO 225
<211> LENGTH: 23
<212> TYPE: DNA
<213> ORGANISM: Artificial
<220> FEATURE:
<223> OTHER INFORMATION: Primer

<400> SEQUENCE: 225
atgtcttatc cttttgcctt ttg                                          23

<210> SEQ ID NO 226
<211> LENGTH: 24
<212> TYPE: DNA
<213> ORGANISM: Artificial
<220> FEATURE:
<223> OTHER INFORMATION: Primer

<400> SEQUENCE: 226
ttgcctttat gtcttatcct tttg                                         24

<210> SEQ ID NO 227
<211> LENGTH: 21
<212> TYPE: DNA
<213> ORGANISM: Artificial
<220> FEATURE:
<223> OTHER INFORMATION: Primer

<400> SEQUENCE: 227
agatatgccc aaaggacaca a                                            21

<210> SEQ ID NO 228
<211> LENGTH: 18
<212> TYPE: DNA
<213> ORGANISM: Artificial
<220> FEATURE:
<223> OTHER INFORMATION: Primer

```
<400> SEQUENCE: 228
gcccggccga aactatta                                                   18

<210> SEQ ID NO 229
<211> LENGTH: 23
<212> TYPE: DNA
<213> ORGANISM: Artificial
<220> FEATURE:
<223> OTHER INFORMATION: Primer

<400> SEQUENCE: 229
tccccttcca tgtgaaacta tta                                             23

<210> SEQ ID NO 230
<211> LENGTH: 20
<212> TYPE: DNA
<213> ORGANISM: Artificial
<220> FEATURE:
<223> OTHER INFORMATION: Primer

<400> SEQUENCE: 230
ctcattccct ttccccactc                                                 20

<210> SEQ ID NO 231
<211> LENGTH: 19
<212> TYPE: DNA
<213> ORGANISM: Artificial
<220> FEATURE:
<223> OTHER INFORMATION: Primer

<400> SEQUENCE: 231
gcccagccta ctcttgtta                                                  19

<210> SEQ ID NO 232
<211> LENGTH: 27
<212> TYPE: DNA
<213> ORGANISM: Artificial
<220> FEATURE:
<223> OTHER INFORMATION: Primer

<400> SEQUENCE: 232
attacctcta ctcttgttaa ccaacca                                         27

<210> SEQ ID NO 233
<211> LENGTH: 26
<212> TYPE: DNA
<213> ORGANISM: Artificial
<220> FEATURE:
<223> OTHER INFORMATION: Primer

<400> SEQUENCE: 233
tgctaacatt acctctactc ttgtta                                          26

<210> SEQ ID NO 234
<211> LENGTH: 20
<212> TYPE: DNA
<213> ORGANISM: Artificial
<220> FEATURE:
<223> OTHER INFORMATION: Primer

<400> SEQUENCE: 234
gtcaacagcc tggtgtcatc                                                 20

<210> SEQ ID NO 235
<211> LENGTH: 19
```

```
<212> TYPE: DNA
<213> ORGANISM: Artificial
<220> FEATURE:
<223> OTHER INFORMATION: Primer

<400> SEQUENCE: 235
agccaccgct ccttgtaac                                                  19

<210> SEQ ID NO 236
<211> LENGTH: 22
<212> TYPE: DNA
<213> ORGANISM: Artificial
<220> FEATURE:
<223> OTHER INFORMATION: Primer

<400> SEQUENCE: 236
actggcctcc ttgtaacttt cc                                              22

<210> SEQ ID NO 237
<211> LENGTH: 26
<212> TYPE: DNA
<213> ORGANISM: Artificial
<220> FEATURE:
<223> OTHER INFORMATION: Primer

<400> SEQUENCE: 237
tttcttagtt ctttaacaac agatgc                                          26

<210> SEQ ID NO 238
<211> LENGTH: 23
<212> TYPE: DNA
<213> ORGANISM: Artificial
<220> FEATURE:
<223> OTHER INFORMATION: Primer

<400> SEQUENCE: 238
tatccttgct agaagttact gga                                             23

<210> SEQ ID NO 239
<211> LENGTH: 23
<212> TYPE: DNA
<213> ORGANISM: Artificial
<220> FEATURE:
<223> OTHER INFORMATION: Primer

<400> SEQUENCE: 239
attccaaaaa gaagttactg gat                                             23

<210> SEQ ID NO 240
<211> LENGTH: 23
<212> TYPE: DNA
<213> ORGANISM: Artificial
<220> FEATURE:
<223> OTHER INFORMATION: Primer

<400> SEQUENCE: 240
aatacagcca aatgaactgg aga                                             23

<210> SEQ ID NO 241
<211> LENGTH: 22
<212> TYPE: DNA
<213> ORGANISM: Artificial
<220> FEATURE:
<223> OTHER INFORMATION: Primer

<400> SEQUENCE: 241
```

```
tctggcctcc atttagtatt tt                                              22
```

<210> SEQ ID NO 242
<211> LENGTH: 25
<212> TYPE: DNA
<213> ORGANISM: Artificial
<220> FEATURE:
<223> OTHER INFORMATION: Primer

<400> SEQUENCE: 242

```
gcactctcta tttagtattt tctcg                                           25
```

<210> SEQ ID NO 243
<211> LENGTH: 23
<212> TYPE: DNA
<213> ORGANISM: Artificial
<220> FEATURE:
<223> OTHER INFORMATION: Primer

<400> SEQUENCE: 243

```
aagtgtcaag gagaacaaaa tgc                                             23
```

<210> SEQ ID NO 244
<211> LENGTH: 18
<212> TYPE: DNA
<213> ORGANISM: Artificial
<220> FEATURE:
<223> OTHER INFORMATION: Primer

<400> SEQUENCE: 244

```
gcctctggcc tccattta                                                   18
```

<210> SEQ ID NO 245
<211> LENGTH: 26
<212> TYPE: DNA
<213> ORGANISM: Artificial
<220> FEATURE:
<223> OTHER INFORMATION: Primer

<400> SEQUENCE: 245

```
gctccaagag cactctctat ttagta                                          26
```

<210> SEQ ID NO 246
<211> LENGTH: 20
<212> TYPE: DNA
<213> ORGANISM: Artificial
<220> FEATURE:
<223> OTHER INFORMATION: Primer

<400> SEQUENCE: 246

```
ccctttgtg tccctcttca                                                  20
```

<210> SEQ ID NO 247
<211> LENGTH: 19
<212> TYPE: DNA
<213> ORGANISM: Artificial
<220> FEATURE:
<223> OTHER INFORMATION: Primer

<400> SEQUENCE: 247

```
accgcgcctg gcctaaagt                                                  19
```

<210> SEQ ID NO 248
<211> LENGTH: 26
<212> TYPE: DNA
<213> ORGANISM: Artificial

```
<220> FEATURE:
<223> OTHER INFORMATION: Primer

<400> SEQUENCE: 248
catgtatccc agaacttaaa gtaaaa                                          26

<210> SEQ ID NO 249
<211> LENGTH: 21
<212> TYPE: DNA
<213> ORGANISM: Artificial
<220> FEATURE:
<223> OTHER INFORMATION: Primer

<400> SEQUENCE: 249
ttgccactta ggcaattaag g                                               21

<210> SEQ ID NO 250
<211> LENGTH: 18
<212> TYPE: DNA
<213> ORGANISM: Artificial
<220> FEATURE:
<223> OTHER INFORMATION: Primer

<400> SEQUENCE: 250
gcctcggcct cccacaag                                                   18

<210> SEQ ID NO 251
<211> LENGTH: 22
<212> TYPE: DNA
<213> ORGANISM: Artificial
<220> FEATURE:
<223> OTHER INFORMATION: Primer

<400> SEQUENCE: 251
ctctgtgcac acaagttttt ca                                              22

<210> SEQ ID NO 252
<211> LENGTH: 20
<212> TYPE: DNA
<213> ORGANISM: Artificial
<220> FEATURE:
<223> OTHER INFORMATION: Primer

<400> SEQUENCE: 252
aaagggaagc ccatcagact                                                 20

<210> SEQ ID NO 253
<211> LENGTH: 18
<212> TYPE: DNA
<213> ORGANISM: Artificial
<220> FEATURE:
<223> OTHER INFORMATION: Primer

<400> SEQUENCE: 253
cccggccgaa aattctttt                                                  18

<210> SEQ ID NO 254
<211> LENGTH: 23
<212> TYPE: DNA
<213> ORGANISM: Artificial
<220> FEATURE:
<223> OTHER INFORMATION: Primer

<400> SEQUENCE: 254
ctgggttgaa aattctttc ttt                                              23
```

```
<210> SEQ ID NO 255
<211> LENGTH: 23
<212> TYPE: DNA
<213> ORGANISM: Artificial
<220> FEATURE:
<223> OTHER INFORMATION: Primer

<400> SEQUENCE: 255
tgtccaggtt aaacttcagt tgc                                              23

<210> SEQ ID NO 256
<211> LENGTH: 18
<212> TYPE: DNA
<213> ORGANISM: Artificial
<220> FEATURE:
<223> OTHER INFORMATION: Primer

<400> SEQUENCE: 256
gcccggcccg aaagaagt                                                    18

<210> SEQ ID NO 257
<211> LENGTH: 19
<212> TYPE: DNA
<213> ORGANISM: Artificial
<220> FEATURE:
<223> OTHER INFORMATION: Primer

<400> SEQUENCE: 257
ggggcaatga aagaagttt                                                   19

<210> SEQ ID NO 258
<211> LENGTH: 21
<212> TYPE: DNA
<213> ORGANISM: Artificial
<220> FEATURE:
<223> OTHER INFORMATION: Primer

<400> SEQUENCE: 258
ttagctgagg gagtcactgg a                                                21

<210> SEQ ID NO 259
<211> LENGTH: 18
<212> TYPE: DNA
<213> ORGANISM: Artificial
<220> FEATURE:
<223> OTHER INFORMATION: Primer

<400> SEQUENCE: 259
cccggccgaa gatttgtt                                                    18

<210> SEQ ID NO 260
<211> LENGTH: 22
<212> TYPE: DNA
<213> ORGANISM: Artificial
<220> FEATURE:
<223> OTHER INFORMATION: Primer

<400> SEQUENCE: 260
gcatgtctcc tgtgaagatt tg                                               22

<210> SEQ ID NO 261
<211> LENGTH: 20
<212> TYPE: DNA
<213> ORGANISM: Artificial
<220> FEATURE:
<223> OTHER INFORMATION: Primer
```

<400> SEQUENCE: 261
tggccaacaa atacgtgaaa 20

<210> SEQ ID NO 262
<211> LENGTH: 18
<212> TYPE: DNA
<213> ORGANISM: Artificial
<220> FEATURE:
<223> OTHER INFORMATION: Primer

<400> SEQUENCE: 262
gcgcccggcc cttaactt 18

<210> SEQ ID NO 263
<211> LENGTH: 25
<212> TYPE: DNA
<213> ORGANISM: Artificial
<220> FEATURE:
<223> OTHER INFORMATION: Primer

<400> SEQUENCE: 263
cagcatctgt tgtttcttaa ctttt 25

<210> SEQ ID NO 264
<211> LENGTH: 18
<212> TYPE: DNA
<213> ORGANISM: Artificial
<220> FEATURE:
<223> OTHER INFORMATION: Primer

<400> SEQUENCE: 264
aggcaggcag atcacttg 18

<210> SEQ ID NO 265
<211> LENGTH: 19
<212> TYPE: DNA
<213> ORGANISM: Artificial
<220> FEATURE:
<223> OTHER INFORMATION: Primer

<400> SEQUENCE: 265
cgcgccccta attctttct 19

<210> SEQ ID NO 266
<211> LENGTH: 21
<212> TYPE: DNA
<213> ORGANISM: Artificial
<220> FEATURE:
<223> OTHER INFORMATION: Primer

<400> SEQUENCE: 266
ccatgcctgg ctaattcttt c 21

<210> SEQ ID NO 267
<211> LENGTH: 20
<212> TYPE: DNA
<213> ORGANISM: Artificial
<220> FEATURE:
<223> OTHER INFORMATION: Primer

<400> SEQUENCE: 267
tgaaatggac tgtggggact 20

<210> SEQ ID NO 268

```
<211> LENGTH: 19
<212> TYPE: DNA
<213> ORGANISM: Artificial
<220> FEATURE:
<223> OTHER INFORMATION: Primer

<400> SEQUENCE: 268
cgtgagccac cgatgaata                                           19

<210> SEQ ID NO 269
<211> LENGTH: 27
<212> TYPE: DNA
<213> ORGANISM: Artificial
<220> FEATURE:
<223> OTHER INFORMATION: Primer

<400> SEQUENCE: 269
tggtatttgg ttacatgaat aaggtct                                  27

<210> SEQ ID NO 270
<211> LENGTH: 25
<212> TYPE: DNA
<213> ORGANISM: Artificial
<220> FEATURE:
<223> OTHER INFORMATION: Primer

<400> SEQUENCE: 270
ctcggcataa ataaaacttt aagga                                    25

<210> SEQ ID NO 271
<211> LENGTH: 18
<212> TYPE: DNA
<213> ORGANISM: Artificial
<220> FEATURE:
<223> OTHER INFORMATION: Primer

<400> SEQUENCE: 271
gcgcccggcc aattctac                                            18

<210> SEQ ID NO 272
<211> LENGTH: 23
<212> TYPE: DNA
<213> ORGANISM: Artificial
<220> FEATURE:
<223> OTHER INFORMATION: Primer

<400> SEQUENCE: 272
ggcttgctca gaattctacc ttc                                      23

<210> SEQ ID NO 273
<211> LENGTH: 20
<212> TYPE: DNA
<213> ORGANISM: Artificial
<220> FEATURE:
<223> OTHER INFORMATION: Primer

<400> SEQUENCE: 273
gaacatccag caccaaatcc                                          20

<210> SEQ ID NO 274
<211> LENGTH: 18
<212> TYPE: DNA
<213> ORGANISM: Artificial
<220> FEATURE:
<223> OTHER INFORMATION: Primer

<400> SEQUENCE: 274
``` cccggccctaccttctta                                            18

<210> SEQ ID NO 275
<211> LENGTH: 22
<212> TYPE: DNA
<213> ORGANISM: Artificial
<220> FEATURE:
<223> OTHER INFORMATION: Primer

<400> SEQUENCE: 275
cctggttgtg tgttaccttc tt                                      22

<210> SEQ ID NO 276
<211> LENGTH: 21
<212> TYPE: DNA
<213> ORGANISM: Artificial
<220> FEATURE:
<223> OTHER INFORMATION: Primer

<400> SEQUENCE: 276
ccttgacagg cactaaccac t                                       21

<210> SEQ ID NO 277
<211> LENGTH: 19
<212> TYPE: DNA
<213> ORGANISM: Artificial
<220> FEATURE:
<223> OTHER INFORMATION: Primer

<400> SEQUENCE: 277
ctcccaaagt gcggttctc                                          19

<210> SEQ ID NO 278
<211> LENGTH: 26
<212> TYPE: DNA
<213> ORGANISM: Artificial
<220> FEATURE:
<223> OTHER INFORMATION: Primer

<400> SEQUENCE: 278
gaatgtggag tacatggttc tcttta                                  26

<210> SEQ ID NO 279
<211> LENGTH: 20
<212> TYPE: DNA
<213> ORGANISM: Artificial
<220> FEATURE:
<223> OTHER INFORMATION: Primer

<400> SEQUENCE: 279
aggagaattg cttgaacctg                                         20

<210> SEQ ID NO 280
<211> LENGTH: 20
<212> TYPE: DNA
<213> ORGANISM: Artificial
<220> FEATURE:
<223> OTHER INFORMATION: Primer

<400> SEQUENCE: 280
tcccaagctg agatcctttc                                         20

<210> SEQ ID NO 281
<211> LENGTH: 21
<212> TYPE: DNA

```
<213> ORGANISM: Artificial
<220> FEATURE:
<223> OTHER INFORMATION: Primer

<400> SEQUENCE: 281
ggtatgctga gatcctttct c                                              21

<210> SEQ ID NO 282
<211> LENGTH: 24
<212> TYPE: DNA
<213> ORGANISM: Artificial
<220> FEATURE:
<223> OTHER INFORMATION: Primer

<400> SEQUENCE: 282
ggttttacca ggaatgtagt ttgg                                           24

<210> SEQ ID NO 283
<211> LENGTH: 18
<212> TYPE: DNA
<213> ORGANISM: Artificial
<220> FEATURE:
<223> OTHER INFORMATION: Primer

<400> SEQUENCE: 283
gcccggcctc atccattc                                                  18

<210> SEQ ID NO 284
<211> LENGTH: 21
<212> TYPE: DNA
<213> ORGANISM: Artificial
<220> FEATURE:
<223> OTHER INFORMATION: Primer

<400> SEQUENCE: 284
gcctcccttc atccattctt a                                              21

<210> SEQ ID NO 285
<211> LENGTH: 20
<212> TYPE: DNA
<213> ORGANISM: Artificial
<220> FEATURE:
<223> OTHER INFORMATION: Primer

<400> SEQUENCE: 285
ccagatggaa gacatgcaca                                                20

<210> SEQ ID NO 286
<211> LENGTH: 18
<212> TYPE: DNA
<213> ORGANISM: Artificial
<220> FEATURE:
<223> OTHER INFORMATION: Primer

<400> SEQUENCE: 286
gcccggccca ttcagtct                                                  18

<210> SEQ ID NO 287
<211> LENGTH: 22
<212> TYPE: DNA
<213> ORGANISM: Artificial
<220> FEATURE:
<223> OTHER INFORMATION: Primer

<400> SEQUENCE: 287
ggagggttca ttcagtcttt tg                                             22
```

<210> SEQ ID NO 288
<211> LENGTH: 24
<212> TYPE: DNA
<213> ORGANISM: Artificial
<220> FEATURE:
<223> OTHER INFORMATION: Primer

<400> SEQUENCE: 288
tcaaaaagac tatctttccc catt                                          24

<210> SEQ ID NO 289
<211> LENGTH: 18
<212> TYPE: DNA
<213> ORGANISM: Artificial
<220> FEATURE:
<223> OTHER INFORMATION: Primer

<400> SEQUENCE: 289
tgggactggg acttagga                                                 18

<210> SEQ ID NO 290
<211> LENGTH: 25
<212> TYPE: DNA
<213> ORGANISM: Artificial
<220> FEATURE:
<223> OTHER INFORMATION: Primer

<400> SEQUENCE: 290
aaagttatgg gagttaggat ttcaa                                         25

<210> SEQ ID NO 291
<211> LENGTH: 20
<212> TYPE: DNA
<213> ORGANISM: Artificial
<220> FEATURE:
<223> OTHER INFORMATION: Primer

<400> SEQUENCE: 291
gcggaaaact aaaggcaaag                                               20

<210> SEQ ID NO 292
<211> LENGTH: 18
<212> TYPE: DNA
<213> ORGANISM: Artificial
<220> FEATURE:
<223> OTHER INFORMATION: Primer

<400> SEQUENCE: 292
cgcccggcct tattttag                                                 18

<210> SEQ ID NO 293
<211> LENGTH: 27
<212> TYPE: DNA
<213> ORGANISM: Artificial
<220> FEATURE:
<223> OTHER INFORMATION: Primer

<400> SEQUENCE: 293
tgggttgata gttattttat tttagtt                                       27

<210> SEQ ID NO 294
<211> LENGTH: 22
<212> TYPE: DNA
<213> ORGANISM: Artificial
<220> FEATURE:

```
<223> OTHER INFORMATION: Primer

<400> SEQUENCE: 294
tgatccatga acattcactc tg                                              22

<210> SEQ ID NO 295
<211> LENGTH: 18
<212> TYPE: DNA
<213> ORGANISM: Artificial
<220> FEATURE:
<223> OTHER INFORMATION: Primer

<400> SEQUENCE: 295
gcccggccca gatctttc                                                   18

<210> SEQ ID NO 296
<211> LENGTH: 25
<212> TYPE: DNA
<213> ORGANISM: Artificial
<220> FEATURE:
<223> OTHER INFORMATION: Primer

<400> SEQUENCE: 296
cagtgcactt tcagatcttt cttta                                           25

<210> SEQ ID NO 297
<211> LENGTH: 24
<212> TYPE: DNA
<213> ORGANISM: Artificial
<220> FEATURE:
<223> OTHER INFORMATION: Primer

<400> SEQUENCE: 297
gggattggat agaatgaaga aagg                                            24

<210> SEQ ID NO 298
<211> LENGTH: 19
<212> TYPE: DNA
<213> ORGANISM: Artificial
<220> FEATURE:
<223> OTHER INFORMATION: Primer

<400> SEQUENCE: 298
gcccggcctc tctctttag                                                  19

<210> SEQ ID NO 299
<211> LENGTH: 22
<212> TYPE: DNA
<213> ORGANISM: Artificial
<220> FEATURE:
<223> OTHER INFORMATION: Primer

<400> SEQUENCE: 299
cgcgctctct ctctctcttt ag                                              22

<210> SEQ ID NO 300
<211> LENGTH: 24
<212> TYPE: DNA
<213> ORGANISM: Artificial
<220> FEATURE:
<223> OTHER INFORMATION: Primer

<400> SEQUENCE: 300
gggattggat agaatgaaga aagg                                            24
```

```
<210> SEQ ID NO 301
<211> LENGTH: 19
<212> TYPE: DNA
<213> ORGANISM: Artificial
<220> FEATURE:
<223> OTHER INFORMATION: Primer

<400> SEQUENCE: 301
gcccggcctc tctctttag                                                    19

<210> SEQ ID NO 302
<211> LENGTH: 22
<212> TYPE: DNA
<213> ORGANISM: Artificial
<220> FEATURE:
<223> OTHER INFORMATION: Primer

<400> SEQUENCE: 302
cgcgctctct ctctctcttt ag                                                22

<210> SEQ ID NO 303
<211> LENGTH: 20
<212> TYPE: DNA
<213> ORGANISM: Artificial
<220> FEATURE:
<223> OTHER INFORMATION: Primer

<400> SEQUENCE: 303
acatggacac gcatgaaaga                                                   20

<210> SEQ ID NO 304
<211> LENGTH: 18
<212> TYPE: DNA
<213> ORGANISM: Artificial
<220> FEATURE:
<223> OTHER INFORMATION: Primer

<400> SEQUENCE: 304
ccggccacaa ccctcatt                                                     18

<210> SEQ ID NO 305
<211> LENGTH: 28
<212> TYPE: DNA
<213> ORGANISM: Artificial
<220> FEATURE:
<223> OTHER INFORMATION: Primer

<400> SEQUENCE: 305
ggtagttacc ttacaaccct cattttta                                          28

<210> SEQ ID NO 306
<211> LENGTH: 25
<212> TYPE: DNA
<213> ORGANISM: Artificial
<220> FEATURE:
<223> OTHER INFORMATION: Primer

<400> SEQUENCE: 306
aagaagagtg aatgcacatt tatga                                             25

<210> SEQ ID NO 307
<211> LENGTH: 19
<212> TYPE: DNA
<213> ORGANISM: Artificial
<220> FEATURE:
<223> OTHER INFORMATION: Primer
```

```
<400> SEQUENCE: 307
cccggcccag tttcttaat                                              19

<210> SEQ ID NO 308
<211> LENGTH: 24
<212> TYPE: DNA
<213> ORGANISM: Artificial
<220> FEATURE:
<223> OTHER INFORMATION: Primer

<400> SEQUENCE: 308
gggagtcatg aattcagttt ctta                                        24

<210> SEQ ID NO 309
<211> LENGTH: 22
<212> TYPE: DNA
<213> ORGANISM: Artificial
<220> FEATURE:
<223> OTHER INFORMATION: Primer

<400> SEQUENCE: 309
cccaagtcta aaccaggaag aa                                          22

<210> SEQ ID NO 310
<211> LENGTH: 21
<212> TYPE: DNA
<213> ORGANISM: Artificial
<220> FEATURE:
<223> OTHER INFORMATION: Primer

<400> SEQUENCE: 310
cccagctacc agttcctctt t                                           21

<210> SEQ ID NO 311
<211> LENGTH: 20
<212> TYPE: DNA
<213> ORGANISM: Artificial
<220> FEATURE:
<223> OTHER INFORMATION: Primer

<400> SEQUENCE: 311
atggtaccag cgcctctttg                                             20

<210> SEQ ID NO 312
<211> LENGTH: 20
<212> TYPE: DNA
<213> ORGANISM: Artificial
<220> FEATURE:
<223> OTHER INFORMATION: Primer

<400> SEQUENCE: 312 tgttttcct tgccacactg                                              20

<210> SEQ ID NO 313
<211> LENGTH: 18
<212> TYPE: DNA
<213> ORGANISM: Artificial
<220> FEATURE:
<223> OTHER INFORMATION: Primer

<400> SEQUENCE: 313
gcgcccggcc ttactctc                                               18

<210> SEQ ID NO 314
<211> LENGTH: 24
```

```
<212> TYPE: DNA
<213> ORGANISM: Artificial
<220> FEATURE:
<223> OTHER INFORMATION: Primer

<400> SEQUENCE: 314
tcttcgtggt cttactctct cttc                                              24

<210> SEQ ID NO 315
<211> LENGTH: 20
<212> TYPE: DNA
<213> ORGANISM: Artificial
<220> FEATURE:
<223> OTHER INFORMATION: Primer

<400> SEQUENCE: 315
agctgccaat aaggctgaaa                                                   20

<210> SEQ ID NO 316
<211> LENGTH: 18
<212> TYPE: DNA
<213> ORGANISM: Artificial
<220> FEATURE:
<223> OTHER INFORMATION: Primer

<400> SEQUENCE: 316
ccgcacctgg ctgattgc                                                     18

<210> SEQ ID NO 317
<211> LENGTH: 19
<212> TYPE: DNA
<213> ORGANISM: Artificial
<220> FEATURE:
<223> OTHER INFORMATION: Primer

<400> SEQUENCE: 317
gggccatttg attgcagtt                                                    19

<210> SEQ ID NO 318
<211> LENGTH: 22
<212> TYPE: DNA
<213> ORGANISM: Artificial
<220> FEATURE:
<223> OTHER INFORMATION: Primer

<400> SEQUENCE: 318
cctagctact aggaagcctg ag                                                22

<210> SEQ ID NO 319
<211> LENGTH: 18
<212> TYPE: DNA
<213> ORGANISM: Artificial
<220> FEATURE:
<223> OTHER INFORMATION: Primer

<400> SEQUENCE: 319
cgcccggcca atttacag                                                     18

<210> SEQ ID NO 320
<211> LENGTH: 25
<212> TYPE: DNA
<213> ORGANISM: Artificial
<220> FEATURE:
<223> OTHER INFORMATION: Primer

<400> SEQUENCE: 320
```

```
aagaactcat tcagaaattt acagc                                          25
```

<210> SEQ ID NO 321
<211> LENGTH: 20
<212> TYPE: DNA
<213> ORGANISM: Artificial
<220> FEATURE:
<223> OTHER INFORMATION: Primer

<400> SEQUENCE: 321

```
tagagtgctg ctgtggcaaa                                                20
```

<210> SEQ ID NO 322
<211> LENGTH: 19
<212> TYPE: DNA
<213> ORGANISM: Artificial
<220> FEATURE:
<223> OTHER INFORMATION: Primer

<400> SEQUENCE: 322

```
gcccagccta gtgtcctct                                                 19
```

<210> SEQ ID NO 323
<211> LENGTH: 21
<212> TYPE: DNA
<213> ORGANISM: Artificial
<220> FEATURE:
<223> OTHER INFORMATION: Primer

<400> SEQUENCE: 323

```
tggttaccta gtggcctctc t                                              21
```

<210> SEQ ID NO 324
<211> LENGTH: 23
<212> TYPE: DNA
<213> ORGANISM: Artificial
<220> FEATURE:
<223> OTHER INFORMATION: Primer

<400> SEQUENCE: 324

```
ccaagtcagg tataagcctc aga                                            23
```

<210> SEQ ID NO 325
<211> LENGTH: 20
<212> TYPE: DNA
<213> ORGANISM: Artificial
<220> FEATURE:
<223> OTHER INFORMATION: Primer

<400> SEQUENCE: 325

```
gccggatgtc cactcttaaa                                                20
```

<210> SEQ ID NO 326
<211> LENGTH: 22
<212> TYPE: DNA
<213> ORGANISM: Artificial
<220> FEATURE:
<223> OTHER INFORMATION: Primer

<400> SEQUENCE: 326

```
acagaaagga tgtccactct ta                                             22
```

<210> SEQ ID NO 327
<211> LENGTH: 21
<212> TYPE: DNA
<213> ORGANISM: Artificial

```
<220> FEATURE:
<223> OTHER INFORMATION: Primer

<400> SEQUENCE: 327
tggcttcctt ttctttcctt a                                              21

<210> SEQ ID NO 328
<211> LENGTH: 18
<212> TYPE: DNA
<213> ORGANISM: Artificial
<220> FEATURE:
<223> OTHER INFORMATION: Primer

<400> SEQUENCE: 328
gcccggccaa aatgactg                                                  18

<210> SEQ ID NO 329
<211> LENGTH: 24
<212> TYPE: DNA
<213> ORGANISM: Artificial
<220> FEATURE:
<223> OTHER INFORMATION: Primer

<400> SEQUENCE: 329
caagcagtga gaaaatgac tgtt                                            24

<210> SEQ ID NO 330
<211> LENGTH: 22
<212> TYPE: DNA
<213> ORGANISM: Artificial
<220> FEATURE:
<223> OTHER INFORMATION: Primer

<400> SEQUENCE: 330
tgctgttcca gaaacacact tt                                             22

<210> SEQ ID NO 331
<211> LENGTH: 18
<212> TYPE: DNA
<213> ORGANISM: Artificial
<220> FEATURE:
<223> OTHER INFORMATION: Primer

<400> SEQUENCE: 331
gcccggccga cacttctt                                                  18

<210> SEQ ID NO 332
<211> LENGTH: 23
<212> TYPE: DNA
<213> ORGANISM: Artificial
<220> FEATURE:
<223> OTHER INFORMATION: Primer

<400> SEQUENCE: 332
cacaatcacc ttgacactt tta                                             23

<210> SEQ ID NO 333
<211> LENGTH: 22
<212> TYPE: DNA
<213> ORGANISM: Artificial
<220> FEATURE:
<223> OTHER INFORMATION: Primer

<400> SEQUENCE: 333
tgatggggat agaggaagaa ga                                             22
```

<210> SEQ ID NO 334
<211> LENGTH: 18
<212> TYPE: DNA
<213> ORGANISM: Artificial
<220> FEATURE:
<223> OTHER INFORMATION: Primer

<400> SEQUENCE: 334
cgcccggcct gtctacca                                                 18

<210> SEQ ID NO 335
<211> LENGTH: 24
<212> TYPE: DNA
<213> ORGANISM: Artificial
<220> FEATURE:
<223> OTHER INFORMATION: Primer

<400> SEQUENCE: 335
gcatctcttg tctaccagtt ttaa                                          24

<210> SEQ ID NO 336
<211> LENGTH: 26
<212> TYPE: DNA
<213> ORGANISM: Artificial
<220> FEATURE:
<223> OTHER INFORMATION: Primer

<400> SEQUENCE: 336
cctaaggtga gtaaggttaa atcctg                                        26

<210> SEQ ID NO 337
<211> LENGTH: 18
<212> TYPE: DNA
<213> ORGANISM: Artificial
<220> FEATURE:
<223> OTHER INFORMATION: Primer

<400> SEQUENCE: 337
cgcccggcct ggattctt                                                 18

<210> SEQ ID NO 338
<211> LENGTH: 22
<212> TYPE: DNA
<213> ORGANISM: Artificial
<220> FEATURE:
<223> OTHER INFORMATION: Primer

<400> SEQUENCE: 338
tgttgtagct gttggattct ta                                            22

<210> SEQ ID NO 339
<211> LENGTH: 20
<212> TYPE: DNA
<213> ORGANISM: Artificial
<220> FEATURE:
<223> OTHER INFORMATION: Primer

<400> SEQUENCE: 339
ccgaattcaa agaaggatca                                               20

<210> SEQ ID NO 340
<211> LENGTH: 20
<212> TYPE: DNA
<213> ORGANISM: Artificial
<220> FEATURE:
<223> OTHER INFORMATION: Primer

```
<400> SEQUENCE: 340
acgcccagtc cttaggctac                                              20

<210> SEQ ID NO 341
<211> LENGTH: 25
<212> TYPE: DNA
<213> ORGANISM: Artificial
<220> FEATURE:
<223> OTHER INFORMATION: Primer

<400> SEQUENCE: 341
tgaccaacac tcttaagcta ctttt                                        25

<210> SEQ ID NO 342
<211> LENGTH: 23
<212> TYPE: DNA
<213> ORGANISM: Artificial
<220> FEATURE:
<223> OTHER INFORMATION: Primer

<400> SEQUENCE: 342
ctgtatcctc atgttctgtt gga                                          23

<210> SEQ ID NO 343
<211> LENGTH: 21
<212> TYPE: DNA
<213> ORGANISM: Artificial
<220> FEATURE:
<223> OTHER INFORMATION: Primer

<400> SEQUENCE: 343
ctgcccactc attttcttag g                                            21

<210> SEQ ID NO 344
<211> LENGTH: 22
<212> TYPE: DNA
<213> ORGANISM: Artificial
<220> FEATURE:
<223> OTHER INFORMATION: Primer

<400> SEQUENCE: 344
ccactcgttt tctctttctt ag                                           22

<210> SEQ ID NO 345
<211> LENGTH: 20
<212> TYPE: DNA
<213> ORGANISM: Artificial
<220> FEATURE:
<223> OTHER INFORMATION: Primer

<400> SEQUENCE: 345
acttgttgac cgagccacat                                              20

<210> SEQ ID NO 346
<211> LENGTH: 18
<212> TYPE: DNA
<213> ORGANISM: Artificial
<220> FEATURE:
<223> OTHER INFORMATION: Primer

<400> SEQUENCE: 346
gcccggccaa gaaactgg                                                18

<210> SEQ ID NO 347
```

```
<211> LENGTH: 24
<212> TYPE: DNA
<213> ORGANISM: Artificial
<220> FEATURE:
<223> OTHER INFORMATION: Primer

<400> SEQUENCE: 347
tccagttaag aaactggtcc cttc                                              24

<210> SEQ ID NO 348
<211> LENGTH: 20
<212> TYPE: DNA
<213> ORGANISM: Artificial
<220> FEATURE:
<223> OTHER INFORMATION: Primer

<400> SEQUENCE: 348
cagccagaag tggcttccta                                                   20

<210> SEQ ID NO 349
<211> LENGTH: 18
<212> TYPE: DNA
<213> ORGANISM: Artificial
<220> FEATURE:
<223> OTHER INFORMATION: Primer

<400> SEQUENCE: 349
cccggccgtc ctttcatt                                                     18

<210> SEQ ID NO 350
<211> LENGTH: 20
<212> TYPE: DNA
<213> ORGANISM: Artificial
<220> FEATURE:
<223> OTHER INFORMATION: Primer

<400> SEQUENCE: 350
gccccaattc ctttcatttt                                                   20

<210> SEQ ID NO 351
<211> LENGTH: 21
<212> TYPE: DNA
<213> ORGANISM: Artificial
<220> FEATURE:
<223> OTHER INFORMATION: Primer

<400> SEQUENCE: 351
tgctggtcag atagaccctg t                                                 21

<210> SEQ ID NO 352
<211> LENGTH: 18
<212> TYPE: DNA
<213> ORGANISM: Artificial
<220> FEATURE:
<223> OTHER INFORMATION: Primer

<400> SEQUENCE: 352
gcccggccaa cactgctt                                                     18

<210> SEQ ID NO 353
<211> LENGTH: 22
<212> TYPE: DNA
<213> ORGANISM: Artificial
<220> FEATURE:
<223> OTHER INFORMATION: Primer

<400> SEQUENCE: 353
```

```
ggggtgaagt aacactgctt tt                                         22
```

<210> SEQ ID NO 354
<211> LENGTH: 20
<212> TYPE: DNA
<213> ORGANISM: Artificial
<220> FEATURE:
<223> OTHER INFORMATION: Primer

<400> SEQUENCE: 354

```
gaatctagcc cttcccttgc                                            20
```

<210> SEQ ID NO 355
<211> LENGTH: 18
<212> TYPE: DNA
<213> ORGANISM: Artificial
<220> FEATURE:
<223> OTHER INFORMATION: Primer

<400> SEQUENCE: 355

```
cccggcagcc aagaagtc                                              18
```

<210> SEQ ID NO 356
<211> LENGTH: 23
<212> TYPE: DNA
<213> ORGANISM: Artificial
<220> FEATURE:
<223> OTHER INFORMATION: Primer

<400> SEQUENCE: 356

```
aaccagagcc aagaagtctt atg                                        23
```

<210> SEQ ID NO 357
<211> LENGTH: 21
<212> TYPE: DNA
<213> ORGANISM: Artificial
<220> FEATURE:
<223> OTHER INFORMATION: Primer

<400> SEQUENCE: 357

```
tggtaaaaat ggggtgacaa a                                          21
```

<210> SEQ ID NO 358
<211> LENGTH: 19
<212> TYPE: DNA
<213> ORGANISM: Artificial
<220> FEATURE:
<223> OTHER INFORMATION: Primer

<400> SEQUENCE: 358

```
cacccggcct acaattttt                                             19
```

<210> SEQ ID NO 359
<211> LENGTH: 25
<212> TYPE: DNA
<213> ORGANISM: Artificial
<220> FEATURE:
<223> OTHER INFORMATION: Primer

<400> SEQUENCE: 359

```
gccacagatg attacaattt ttcaa                                      25
```

<210> SEQ ID NO 360
<211> LENGTH: 23
<212> TYPE: DNA

```
<213> ORGANISM: Artificial
<220> FEATURE:
<223> OTHER INFORMATION: Primer

<400> SEQUENCE: 360
ccagtgcctg tgtatctaag tga                                          23

<210> SEQ ID NO 361
<211> LENGTH: 20
<212> TYPE: DNA
<213> ORGANISM: Artificial
<220> FEATURE:
<223> OTHER INFORMATION: Primer

<400> SEQUENCE: 361
gagagggaga gggaactgaa                                              20

<210> SEQ ID NO 362
<211> LENGTH: 26
<212> TYPE: DNA
<213> ORGANISM: Artificial
<220> FEATURE:
<223> OTHER INFORMATION: Primer

<400> SEQUENCE: 362
tcaatggagt acagaactga atctta                                       26

<210> SEQ ID NO 363
<211> LENGTH: 26
<212> TYPE: DNA
<213> ORGANISM: Artificial
<220> FEATURE:
<223> OTHER INFORMATION: Primer

<400> SEQUENCE: 363
gaaatgaata agcttcttgg atagtg                                       26

<210> SEQ ID NO 364
<211> LENGTH: 20
<212> TYPE: DNA
<213> ORGANISM: Artificial
<220> FEATURE:
<223> OTHER INFORMATION: Primer

<400> SEQUENCE: 364
gggagaggga gaggtcatta                                              20

<210> SEQ ID NO 365
<211> LENGTH: 21
<212> TYPE: DNA
<213> ORGANISM: Artificial
<220> FEATURE:
<223> OTHER INFORMATION: Primer

<400> SEQUENCE: 365
cggccaatct cattattttc a                                            21

<210> SEQ ID NO 366
<211> LENGTH: 20
<212> TYPE: DNA
<213> ORGANISM: Artificial
<220> FEATURE:
<223> OTHER INFORMATION: Primer

<400> SEQUENCE: 366
aaagctgggt ttcctttgc                                               20
```

-continued

<210> SEQ ID NO 367
<211> LENGTH: 18
<212> TYPE: DNA
<213> ORGANISM: Artificial
<220> FEATURE:
<223> OTHER INFORMATION: Primer

<400> SEQUENCE: 367
ggctggccgg aagtctta                                                18

<210> SEQ ID NO 368
<211> LENGTH: 26
<212> TYPE: DNA
<213> ORGANISM: Artificial
<220> FEATURE:
<223> OTHER INFORMATION: Primer

<400> SEQUENCE: 368
tggtgtcttg aaggatagaa gtctta                                       26

<210> SEQ ID NO 369
<211> LENGTH: 20
<212> TYPE: DNA
<213> ORGANISM: Artificial
<220> FEATURE:
<223> OTHER INFORMATION: Primer

<400> SEQUENCE: 369
cgtggtgatg tgcactttta                                              20

<210> SEQ ID NO 370
<211> LENGTH: 20
<212> TYPE: DNA
<213> ORGANISM: Artificial
<220> FEATURE:
<223> OTHER INFORMATION: Primer

<400> SEQUENCE: 370
ttaaattttt gaccgggttt                                              20

<210> SEQ ID NO 371
<211> LENGTH: 26
<212> TYPE: DNA
<213> ORGANISM: Artificial
<220> FEATURE:
<223> OTHER INFORMATION: Primer

<400> SEQUENCE: 371
gaaggaaaag tagttaaggg tttttg                                       26

<210> SEQ ID NO 372
<211> LENGTH: 20
<212> TYPE: DNA
<213> ORGANISM: Artificial
<220> FEATURE:
<223> OTHER INFORMATION: Primer

<400> SEQUENCE: 372
ccctgctatc ctaaatgctg                                              20

<210> SEQ ID NO 373
<211> LENGTH: 19
<212> TYPE: DNA
<213> ORGANISM: Artificial
<220> FEATURE:

```
<223> OTHER INFORMATION: Primer

<400> SEQUENCE: 373
gtgatggcgg gcttaacct                                                    19

<210> SEQ ID NO 374
<211> LENGTH: 20
<212> TYPE: DNA
<213> ORGANISM: Artificial
<220> FEATURE:
<223> OTHER INFORMATION: Primer

<400> SEQUENCE: 374
cagcccaccc ttaacctcta                                                   20

<210> SEQ ID NO 375
<211> LENGTH: 20
<212> TYPE: DNA
<213> ORGANISM: Artificial
<220> FEATURE:
<223> OTHER INFORMATION: Primer

<400> SEQUENCE: 375
tttcctcttg ttcgtgatgg                                                   20

<210> SEQ ID NO 376
<211> LENGTH: 20
<212> TYPE: DNA
<213> ORGANISM: Artificial
<220> FEATURE:
<223> OTHER INFORMATION: Primer

<400> SEQUENCE: 376
ggtggttcca agctgttttc                                                   20

<210> SEQ ID NO 377
<211> LENGTH: 24
<212> TYPE: DNA
<213> ORGANISM: Artificial
<220> FEATURE:
<223> OTHER INFORMATION: Primer

<400> SEQUENCE: 377
ccaaaaaccc atagctgttt tcta                                              24

<210> SEQ ID NO 378
<211> LENGTH: 20
<212> TYPE: DNA
<213> ORGANISM: Artificial
<220> FEATURE:
<223> OTHER INFORMATION: Primer

<400> SEQUENCE: 378
tgggcatcac tcagctctaa                                                   20

<210> SEQ ID NO 379
<211> LENGTH: 18
<212> TYPE: DNA
<213> ORGANISM: Artificial
<220> FEATURE:
<223> OTHER INFORMATION: Primer

<400> SEQUENCE: 379
ctcctccttc cggcactg                                                     18
```

```
<210> SEQ ID NO 380
<211> LENGTH: 19
<212> TYPE: DNA
<213> ORGANISM: Artificial
<220> FEATURE:
<223> OTHER INFORMATION: Primer

<400> SEQUENCE: 380
acttctcggc actggcttt                                              19

<210> SEQ ID NO 381
<211> LENGTH: 20
<212> TYPE: DNA
<213> ORGANISM: Artificial
<220> FEATURE:
<223> OTHER INFORMATION: Primer

<400> SEQUENCE: 381
ttgctcagag cccataagga                                             20

<210> SEQ ID NO 382
<211> LENGTH: 18
<212> TYPE: DNA
<213> ORGANISM: Artificial
<220> FEATURE:
<223> OTHER INFORMATION: Primer

<400> SEQUENCE: 382
tggctcctcc aagccttc                                               18

<210> SEQ ID NO 383
<211> LENGTH: 27
<212> TYPE: DNA
<213> ORGANISM: Artificial
<220> FEATURE:
<223> OTHER INFORMATION: Primer

<400> SEQUENCE: 383
ctacacatta aattaagcct tcaaatt                                     27

<210> SEQ ID NO 384
<211> LENGTH: 21
<212> TYPE: DNA
<213> ORGANISM: Artificial
<220> FEATURE:
<223> OTHER INFORMATION: Primer

<400> SEQUENCE: 384
tgaataccat gatatgccaa a                                           21

<210> SEQ ID NO 385
<211> LENGTH: 19
<212> TYPE: DNA
<213> ORGANISM: Artificial
<220> FEATURE:
<223> OTHER INFORMATION: Primer

<400> SEQUENCE: 385
tgattgccat tcacactcc                                              19

<210> SEQ ID NO 386
<211> LENGTH: 21
<212> TYPE: DNA
<213> ORGANISM: Artificial
<220> FEATURE:
<223> OTHER INFORMATION: Primer
```

```
<400> SEQUENCE: 386
gaaattgcca cactccttttt c                                          21

<210> SEQ ID NO 387
<211> LENGTH: 23
<212> TYPE: DNA
<213> ORGANISM: Artificial
<220> FEATURE:
<223> OTHER INFORMATION: Primer

<400> SEQUENCE: 387
agcagcatga tttataatcc ttt                                         23

<210> SEQ ID NO 388
<211> LENGTH: 19
<212> TYPE: DNA
<213> ORGANISM: Artificial
<220> FEATURE:
<223> OTHER INFORMATION: Primer

<400> SEQUENCE: 388
ggtcccctaa caggagcac                                              19

<210> SEQ ID NO 389
<211> LENGTH: 25
<212> TYPE: DNA
<213> ORGANISM: Artificial
<220> FEATURE:
<223> OTHER INFORMATION: Primer

<400> SEQUENCE: 389
tgtggagaaa tatgaacact tttac                                       25

<210> SEQ ID NO 390
<211> LENGTH: 23
<212> TYPE: DNA
<213> ORGANISM: Artificial
<220> FEATURE:
<223> OTHER INFORMATION: Primer

<400> SEQUENCE: 390
taacatttga ccaaacagtt gag                                         23

<210> SEQ ID NO 391
<211> LENGTH: 19
<212> TYPE: DNA
<213> ORGANISM: Artificial
<220> FEATURE:
<223> OTHER INFORMATION: Primer

<400> SEQUENCE: 391
cccacttttt gacctttca                                              19

<210> SEQ ID NO 392
<211> LENGTH: 20
<212> TYPE: DNA
<213> ORGANISM: Artificial
<220> FEATURE:
<223> OTHER INFORMATION: Primer

<400> SEQUENCE: 392
ccgctgcttc taacctttca                                             20

<210> SEQ ID NO 393
<211> LENGTH: 22
```

```
<212> TYPE: DNA
<213> ORGANISM: Artificial
<220> FEATURE:
<223> OTHER INFORMATION: Primer

<400> SEQUENCE: 393
ttctcttctt ccctctctga gc                                    22

<210> SEQ ID NO 394
<211> LENGTH: 19
<212> TYPE: DNA
<213> ORGANISM: Artificial
<220> FEATURE:
<223> OTHER INFORMATION: Primer

<400> SEQUENCE: 394
cttggctcct cctgcaaat                                        19

<210> SEQ ID NO 395
<211> LENGTH: 22
<212> TYPE: DNA
<213> ORGANISM: Artificial
<220> FEATURE:
<223> OTHER INFORMATION: Primer

<400> SEQUENCE: 395
tctctgctca ttgcaaatct ta                                    22

<210> SEQ ID NO 396
<211> LENGTH: 20
<212> TYPE: DNA
<213> ORGANISM: Artificial
<220> FEATURE:
<223> OTHER INFORMATION: Primer

<400> SEQUENCE: 396
ctctggagaa gggtgcattg                                       20

<210> SEQ ID NO 397
<211> LENGTH: 18
<212> TYPE: DNA
<213> ORGANISM: Artificial
<220> FEATURE:
<223> OTHER INFORMATION: Primer

<400> SEQUENCE: 397
cgtcgctcac gctctgtg                                         18

<210> SEQ ID NO 398
<211> LENGTH: 25
<212> TYPE: DNA
<213> ORGANISM: Artificial
<220> FEATURE:
<223> OTHER INFORMATION: Primer

<400> SEQUENCE: 398
ttagagagag agatttgtga gtgtt                                 25

<210> SEQ ID NO 399
<211> LENGTH: 21
<212> TYPE: DNA
<213> ORGANISM: Artificial
<220> FEATURE:
<223> OTHER INFORMATION: Primer

<400> SEQUENCE: 399
```
tgctagtaga acccacgagg t                                              21

<210> SEQ ID NO 400
<211> LENGTH: 18
<212> TYPE: DNA
<213> ORGANISM: Artificial
<220> FEATURE:
<223> OTHER INFORMATION: Primer

<400> SEQUENCE: 400
ggcacaagac agggatgc                                                  18

<210> SEQ ID NO 401
<211> LENGTH: 23
<212> TYPE: DNA
<213> ORGANISM: Artificial
<220> FEATURE:
<223> OTHER INFORMATION: Primer

<400> SEQUENCE: 401
gaaaagacaa agttgcattg tta                                            23

<210> SEQ ID NO 402
<211> LENGTH: 21
<212> TYPE: DNA
<213> ORGANISM: Artificial
<220> FEATURE:
<223> OTHER INFORMATION: Primer

<400> SEQUENCE: 402
tcctaacaag ggactttgca g                                              21

<210> SEQ ID NO 403
<211> LENGTH: 18
<212> TYPE: DNA
<213> ORGANISM: Artificial
<220> FEATURE:
<223> OTHER INFORMATION: Primer

<400> SEQUENCE: 403
cggcctccca aagaagat                                                  18

<210> SEQ ID NO 404
<211> LENGTH: 22
<212> TYPE: DNA
<213> ORGANISM: Artificial
<220> FEATURE:
<223> OTHER INFORMATION: Primer

<400> SEQUENCE: 404
gatgggaaag attctccact tt                                             22

<210> SEQ ID NO 405
<211> LENGTH: 20
<212> TYPE: DNA
<213> ORGANISM: Artificial
<220> FEATURE:
<223> OTHER INFORMATION: Primer

<400> SEQUENCE: 405
caggcctggt ggtaacaaat                                                20

<210> SEQ ID NO 406
<211> LENGTH: 17
<212> TYPE: DNA
<213> ORGANISM: Artificial

```
<220> FEATURE:
<223> OTHER INFORMATION: Primer

<400> SEQUENCE: 406
tcggcctccc aatcaac                                                        17

<210> SEQ ID NO 407
<211> LENGTH: 21
<212> TYPE: DNA
<213> ORGANISM: Artificial
<220> FEATURE:
<223> OTHER INFORMATION: Primer

<400> SEQUENCE: 407
ggccaatatt caacattctt a                                                   21

<210> SEQ ID NO 408
<211> LENGTH: 21
<212> TYPE: DNA
<213> ORGANISM: Artificial
<220> FEATURE:
<223> OTHER INFORMATION: Primer

<400> SEQUENCE: 408
ccctggactt accctatctc a                                                   21

<210> SEQ ID NO 409
<211> LENGTH: 21
<212> TYPE: DNA
<213> ORGANISM: Artificial
<220> FEATURE:
<223> OTHER INFORMATION: Primer

<400> SEQUENCE: 409
tgctgggatt acatggattt t                                                   21

<210> SEQ ID NO 410
<211> LENGTH: 24
<212> TYPE: DNA
<213> ORGANISM: Artificial
<220> FEATURE:
<223> OTHER INFORMATION: Primer

<400> SEQUENCE: 410
ggagaatgtg tgtggatttt attc                                                24

<210> SEQ ID NO 411
<211> LENGTH: 20
<212> TYPE: DNA
<213> ORGANISM: Artificial
<220> FEATURE:
<223> OTHER INFORMATION: Primer

<400> SEQUENCE: 411
aaaaacaagc aatggggaaa                                                     20

<210> SEQ ID NO 412
<211> LENGTH: 19
<212> TYPE: DNA
<213> ORGANISM: Artificial
<220> FEATURE:
<223> OTHER INFORMATION: Primer

<400> SEQUENCE: 412
gtgtccggcc acgtttaag                                                      19
```

<210> SEQ ID NO 413
<211> LENGTH: 26
<212> TYPE: DNA
<213> ORGANISM: Artificial
<220> FEATURE:
<223> OTHER INFORMATION: Primer

<400> SEQUENCE: 413
gttttaggtc taacgtttaa gtcttt                                   26

<210> SEQ ID NO 414
<211> LENGTH: 20
<212> TYPE: DNA
<213> ORGANISM: Artificial
<220> FEATURE:
<223> OTHER INFORMATION: Primer

<400> SEQUENCE: 414
tgccaggaat ggacttacaa                                          20

<210> SEQ ID NO 415
<211> LENGTH: 20
<212> TYPE: DNA
<213> ORGANISM: Artificial
<220> FEATURE:
<223> OTHER INFORMATION: Primer

<400> SEQUENCE: 415
cccggccatg aacttctaat                                          20

<210> SEQ ID NO 416
<211> LENGTH: 26
<212> TYPE: DNA
<213> ORGANISM: Artificial
<220> FEATURE:
<223> OTHER INFORMATION: Primer

<400> SEQUENCE: 416
tgacctgcat gaacttctaa taaaat                                   26

<210> SEQ ID NO 417
<211> LENGTH: 23
<212> TYPE: DNA
<213> ORGANISM: Artificial
<220> FEATURE:
<223> OTHER INFORMATION: Primer

<400> SEQUENCE: 417
ttcatgacct gcatgaactt cta                                      23

<210> SEQ ID NO 418
<211> LENGTH: 27
<212> TYPE: DNA
<213> ORGANISM: Artificial
<220> FEATURE:
<223> OTHER INFORMATION: Primer

<400> SEQUENCE: 418
ggtaatcaac agaagatcat aagagga                                  27

<210> SEQ ID NO 419
<211> LENGTH: 19
<212> TYPE: DNA
<213> ORGANISM: Artificial
<220> FEATURE:
<223> OTHER INFORMATION: Primer

```
<400> SEQUENCE: 419
gttaagactt gaggccggg                                              19

<210> SEQ ID NO 420
<211> LENGTH: 23
<212> TYPE: DNA
<213> ORGANISM: Artificial
<220> FEATURE:
<223> OTHER INFORMATION: Primer

<400> SEQUENCE: 420
cttctctcct ccctcaagtc tta                                         23

<210> SEQ ID NO 421
<211> LENGTH: 20
<212> TYPE: DNA
<213> ORGANISM: Artificial
<220> FEATURE:
<223> OTHER INFORMATION: Primer

<400> SEQUENCE: 421
caagtgctgg ggattacagg                                             20

<210> SEQ ID NO 422
<211> LENGTH: 20
<212> TYPE: DNA
<213> ORGANISM: Artificial
<220> FEATURE:
<223> OTHER INFORMATION: Primer

<400> SEQUENCE: 422
agacggggtt tcaccgttag                                             20

<210> SEQ ID NO 423
<211> LENGTH: 22
<212> TYPE: DNA
<213> ORGANISM: Artificial
<220> FEATURE:
<223> OTHER INFORMATION: Primer

<400> SEQUENCE: 423
gcagagagac taggaggcat tc                                          22

<210> SEQ ID NO 424
<211> LENGTH: 20
<212> TYPE: DNA
<213> ORGANISM: Artificial
<220> FEATURE:
<223> OTHER INFORMATION: Primer

<400> SEQUENCE: 424
ccatggactc atggaatgct                                             20

<210> SEQ ID NO 425
<211> LENGTH: 20
<212> TYPE: DNA
<213> ORGANISM: Artificial
<220> FEATURE:
<223> OTHER INFORMATION: Primer

<400> SEQUENCE: 425
agcctgccac acttctttag                                             20

<210> SEQ ID NO 426
```

```
<211> LENGTH: 20
<212> TYPE: DNA
<213> ORGANISM: Artificial
<220> FEATURE:
<223> OTHER INFORMATION: Primer

<400> SEQUENCE: 426
ttccatgacg gcacttcttt                                              20

<210> SEQ ID NO 427
<211> LENGTH: 23
<212> TYPE: DNA
<213> ORGANISM: Artificial
<220> FEATURE:
<223> OTHER INFORMATION: Primer

<400> SEQUENCE: 427
tgtaggcaaa actttagttt cat                                          23

<210> SEQ ID NO 428
<211> LENGTH: 18
<212> TYPE: DNA
<213> ORGANISM: Artificial
<220> FEATURE:
<223> OTHER INFORMATION: Primer

<400> SEQUENCE: 428
cccggcccag aaagaact                                                18

<210> SEQ ID NO 429
<211> LENGTH: 24
<212> TYPE: DNA
<213> ORGANISM: Artificial
<220> FEATURE:
<223> OTHER INFORMATION: Primer

<400> SEQUENCE: 429
ctcccattat cttcagaaag aact                                         24

<210> SEQ ID NO 430
<211> LENGTH: 22
<212> TYPE: DNA
<213> ORGANISM: Artificial
<220> FEATURE:
<223> OTHER INFORMATION: Primer

<400> SEQUENCE: 430
ccattaaagg aacaagaatg ga                                           22

<210> SEQ ID NO 431
<211> LENGTH: 19
<212> TYPE: DNA
<213> ORGANISM: Artificial
<220> FEATURE:
<223> OTHER INFORMATION: Primer

<400> SEQUENCE: 431
gcccggccag taatcttta                                               19

<210> SEQ ID NO 432
<211> LENGTH: 25
<212> TYPE: DNA
<213> ORGANISM: Artificial
<220> FEATURE:
<223> OTHER INFORMATION: Primer

<400> SEQUENCE: 432
```

-continued ctggtccagt aatctttaat acact                                     25

<210> SEQ ID NO 433
<211> LENGTH: 20
<212> TYPE: DNA
<213> ORGANISM: Artificial
<220> FEATURE:
<223> OTHER INFORMATION: Primer

<400> SEQUENCE: 433
ctgagctgga ggcataggtc                                           20

<210> SEQ ID NO 434
<211> LENGTH: 18
<212> TYPE: DNA
<213> ORGANISM: Artificial
<220> FEATURE:
<223> OTHER INFORMATION: Primer

<400> SEQUENCE: 434
ccggcccggc tattttta                                             18

<210> SEQ ID NO 435
<211> LENGTH: 20
<212> TYPE: DNA
<213> ORGANISM: Artificial
<220> FEATURE:
<223> OTHER INFORMATION: Primer

<400> SEQUENCE: 435
tgttgcccag gctattttta                                           20

<210> SEQ ID NO 436
<211> LENGTH: 21
<212> TYPE: DNA
<213> ORGANISM: Artificial
<220> FEATURE:
<223> OTHER INFORMATION: Primer

<400> SEQUENCE: 436
tggagagcat tgacagttca t                                         21

<210> SEQ ID NO 437
<211> LENGTH: 18
<212> TYPE: DNA
<213> ORGANISM: Artificial
<220> FEATURE:
<223> OTHER INFORMATION: Primer

<400> SEQUENCE: 437
ccggcccctg cttcttat                                             18

<210> SEQ ID NO 438
<211> LENGTH: 21
<212> TYPE: DNA
<213> ORGANISM: Artificial
<220> FEATURE:
<223> OTHER INFORMATION: Primer

<400> SEQUENCE: 438
acacactcac cctgcttctt a                                         21

<210> SEQ ID NO 439
<211> LENGTH: 19
<212> TYPE: DNA

```
<213> ORGANISM: Artificial
<220> FEATURE:
<223> OTHER INFORMATION: Primer

<400> SEQUENCE: 439
aggtgctggc actgatgac                                                    19

<210> SEQ ID NO 440
<211> LENGTH: 20
<212> TYPE: DNA
<213> ORGANISM: Artificial
<220> FEATURE:
<223> OTHER INFORMATION: Primer

<400> SEQUENCE: 440
ctgggattac aagcgtgagg                                                   20

<210> SEQ ID NO 441
<211> LENGTH: 23
<212> TYPE: DNA
<213> ORGANISM: Artificial
<220> FEATURE:
<223> OTHER INFORMATION: Primer

<400> SEQUENCE: 441
tctcacaagt aagcaaggta gat                                               23

<210> SEQ ID NO 442
<211> LENGTH: 24
<212> TYPE: DNA
<213> ORGANISM: Artificial
<220> FEATURE:
<223> OTHER INFORMATION: Primer

<400> SEQUENCE: 442
ccttaagacc taagccctag taga                                              24

<210> SEQ ID NO 443
<211> LENGTH: 20
<212> TYPE: DNA
<213> ORGANISM: Artificial
<220> FEATURE:
<223> OTHER INFORMATION: Primer

<400> SEQUENCE: 443
caggcgtgag ccactaactt                                                   20

<210> SEQ ID NO 444
<211> LENGTH: 23
<212> TYPE: DNA
<213> ORGANISM: Artificial
<220> FEATURE:
<223> OTHER INFORMATION: Primer

<400> SEQUENCE: 444
gtttcccaag ccactaactt tta                                               23

<210> SEQ ID NO 445
<211> LENGTH: 23
<212> TYPE: DNA
<213> ORGANISM: Artificial
<220> FEATURE:
<223> OTHER INFORMATION: Primer

<400> SEQUENCE: 445
gaatgcaagt aaaaaccatg agg                                               23
```

```
<210> SEQ ID NO 446
<211> LENGTH: 22
<212> TYPE: DNA
<213> ORGANISM: Artificial
<220> FEATURE:
<223> OTHER INFORMATION: Primer

<400> SEQUENCE: 446
tttagtagag acggggttag ca                                               22

<210> SEQ ID NO 447
<211> LENGTH: 23
<212> TYPE: DNA
<213> ORGANISM: Artificial
<220> FEATURE:
<223> OTHER INFORMATION: Primer

<400> SEQUENCE: 447
tccttgtgtc tagcatgttt ttg                                              23

<210> SEQ ID NO 448
<211> LENGTH: 25
<212> TYPE: DNA
<213> ORGANISM: Artificial
<220> FEATURE:
<223> OTHER INFORMATION: Primer

<400> SEQUENCE: 448
aaccaaagtg actctgaaga agaaa                                            25

<210> SEQ ID NO 449
<211> LENGTH: 20
<212> TYPE: DNA
<213> ORGANISM: Artificial
<220> FEATURE:
<223> OTHER INFORMATION: Primer

<400> SEQUENCE: 449
tcctgggttc acgtatgatg                                                  20

<210> SEQ ID NO 450
<211> LENGTH: 22
<212> TYPE: DNA
<213> ORGANISM: Artificial
<220> FEATURE:
<223> OTHER INFORMATION: Primer

<400> SEQUENCE: 450
ttggaactgg ctatgatgtt tg                                               22

<210> SEQ ID NO 451
<211> LENGTH: 20
<212> TYPE: DNA
<213> ORGANISM: Artificial
<220> FEATURE:
<223> OTHER INFORMATION: Primer

<400> SEQUENCE: 451
ggttgatcat ctgccgaaag                                                  20

<210> SEQ ID NO 452
<211> LENGTH: 18
<212> TYPE: DNA
<213> ORGANISM: Artificial
<220> FEATURE:
```

<223> OTHER INFORMATION: Primer

<400> SEQUENCE: 452
gccaccgcgc cctctact                                                  18

<210> SEQ ID NO 453
<211> LENGTH: 25
<212> TYPE: DNA
<213> ORGANISM: Artificial
<220> FEATURE:
<223> OTHER INFORMATION: Primer

<400> SEQUENCE: 453
cacctttacc accttctact gtcta                                          25

<210> SEQ ID NO 454
<211> LENGTH: 20
<212> TYPE: DNA
<213> ORGANISM: Artificial
<220> FEATURE:
<223> OTHER INFORMATION: Primer

<400> SEQUENCE: 454
cttgagccca ggagtttgag                                                20

<210> SEQ ID NO 455
<211> LENGTH: 18
<212> TYPE: DNA
<213> ORGANISM: Artificial
<220> FEATURE:
<223> OTHER INFORMATION: Primer

<400> SEQUENCE: 455
cgcccggcct tatttttc                                                  18

<210> SEQ ID NO 456
<211> LENGTH: 21
<212> TYPE: DNA
<213> ORGANISM: Artificial
<220> FEATURE:
<223> OTHER INFORMATION: Primer

<400> SEQUENCE: 456
gagaggcccc cttattttc t                                               21

<210> SEQ ID NO 457
<211> LENGTH: 21
<212> TYPE: DNA
<213> ORGANISM: Artificial
<220> FEATURE:
<223> OTHER INFORMATION: Primer

<400> SEQUENCE: 457
aacaaaattc cctttcctcc a                                              21

<210> SEQ ID NO 458
<211> LENGTH: 18
<212> TYPE: DNA
<213> ORGANISM: Artificial
<220> FEATURE:
<223> OTHER INFORMATION: Primer

<400> SEQUENCE: 458
cgcccggcca gaagttag                                                  18

```
<210> SEQ ID NO 459
<211> LENGTH: 26
<212> TYPE: DNA
<213> ORGANISM: Artificial
<220> FEATURE:
<223> OTHER INFORMATION: Primer

<400> SEQUENCE: 459
ggatatatgc tagcagaagt tagatt                                     26

<210> SEQ ID NO 460
<211> LENGTH: 23
<212> TYPE: DNA
<213> ORGANISM: Artificial
<220> FEATURE:
<223> OTHER INFORMATION: Primer

<400> SEQUENCE: 460
cctgaggtgt gtgcttaatc ttc                                        23

<210> SEQ ID NO 461
<211> LENGTH: 18
<212> TYPE: DNA
<213> ORGANISM: Artificial
<220> FEATURE:
<223> OTHER INFORMATION: Primer

<400> SEQUENCE: 461
cccggccgcc agtttctt                                              18

<210> SEQ ID NO 462
<211> LENGTH: 22
<212> TYPE: DNA
<213> ORGANISM: Artificial
<220> FEATURE:
<223> OTHER INFORMATION: Primer

<400> SEQUENCE: 462
ttttcccaga accagtttct ta                                         22

<210> SEQ ID NO 463
<211> LENGTH: 20
<212> TYPE: DNA
<213> ORGANISM: Artificial
<220> FEATURE:
<223> OTHER INFORMATION: Primer

<400> SEQUENCE: 463
ctctcctgtg cccacttagg                                            20

<210> SEQ ID NO 464
<211> LENGTH: 18
<212> TYPE: DNA
<213> ORGANISM: Artificial
<220> FEATURE:
<223> OTHER INFORMATION: Primer

<400> SEQUENCE: 464
acgcccggcc atattctt                                              18

<210> SEQ ID NO 465
<211> LENGTH: 24
<212> TYPE: DNA
<213> ORGANISM: Artificial
<220> FEATURE:
<223> OTHER INFORMATION: Primer
```

<400> SEQUENCE: 465
tggagtcatg tccatatatt cttg                                          24

<210> SEQ ID NO 466
<211> LENGTH: 21
<212> TYPE: DNA
<213> ORGANISM: Artificial
<220> FEATURE:
<223> OTHER INFORMATION: Primer

<400> SEQUENCE: 466
ttttcggttg tgaactgaag g                                             21

<210> SEQ ID NO 467
<211> LENGTH: 18
<212> TYPE: DNA
<213> ORGANISM: Artificial
<220> FEATURE:
<223> OTHER INFORMATION: Primer

<400> SEQUENCE: 467
cgcccagcct taaactga                                                 18

<210> SEQ ID NO 468
<211> LENGTH: 20
<212> TYPE: DNA
<213> ORGANISM: Artificial
<220> FEATURE:
<223> OTHER INFORMATION: Primer

<400> SEQUENCE: 468
accagcccct aaactgacca                                               20

<210> SEQ ID NO 469
<211> LENGTH: 23
<212> TYPE: DNA
<213> ORGANISM: Artificial
<220> FEATURE:
<223> OTHER INFORMATION: Primer

<400> SEQUENCE: 469
caggccatgt aagagtagaa gga                                           23

<210> SEQ ID NO 470
<211> LENGTH: 18
<212> TYPE: DNA
<213> ORGANISM: Artificial
<220> FEATURE:
<223> OTHER INFORMATION: Primer

<400> SEQUENCE: 470
gcccggccag aacactac                                                 18

<210> SEQ ID NO 471
<211> LENGTH: 26
<212> TYPE: DNA
<213> ORGANISM: Artificial
<220> FEATURE:
<223> OTHER INFORMATION: Primer

<400> SEQUENCE: 471
caaccctatg agattagaac actaca                                        26

<210> SEQ ID NO 472
<211> LENGTH: 21

```
<212> TYPE: DNA
<213> ORGANISM: Artificial
<220> FEATURE:
<223> OTHER INFORMATION: Primer

<400> SEQUENCE: 472
cattgaatga atggggaaga a                                              21

<210> SEQ ID NO 473
<211> LENGTH: 18
<212> TYPE: DNA
<213> ORGANISM: Artificial
<220> FEATURE:
<223> OTHER INFORMATION: Primer

<400> SEQUENCE: 473
gcctggcgca aagatatg                                                  18

<210> SEQ ID NO 474
<211> LENGTH: 22
<212> TYPE: DNA
<213> ORGANISM: Artificial
<220> FEATURE:
<223> OTHER INFORMATION: Primer

<400> SEQUENCE: 474
ttggaaccaa agcaaagata tg                                             22

<210> SEQ ID NO 475
<211> LENGTH: 23
<212> TYPE: DNA
<213> ORGANISM: Artificial
<220> FEATURE:
<223> OTHER INFORMATION: Primer

<400> SEQUENCE: 475
ggcaaagagt gaactagaat cca                                            23

<210> SEQ ID NO 476
<211> LENGTH: 18
<212> TYPE: DNA
<213> ORGANISM: Artificial
<220> FEATURE:
<223> OTHER INFORMATION: Primer

<400> SEQUENCE: 476
gcgcccggcc tcaactac                                                  18

<210> SEQ ID NO 477
<211> LENGTH: 25
<212> TYPE: DNA
<213> ORGANISM: Artificial
<220> FEATURE:
<223> OTHER INFORMATION: Primer

<400> SEQUENCE: 477
ggaagagcac actcaactac tttta                                          25

<210> SEQ ID NO 478
<211> LENGTH: 384
<212> TYPE: DNA
<213> ORGANISM: Homo sapiens

<400> SEQUENCE: 478
gcaaagcatt caagaggtga cttgggtact gttaaaggca ttcagttttg gtggggtgtg    60
```

-continued

```
gtggcacaca cctgcaattc cagcacttag ggaggccgag gcgggtgaat cacctgaggt    120
tgggagttcg agaccagcct aaccaacatg gagaaacccc gtctctacta aaaatacaaa    180
attagccagt cttggtgtca catgcctgta atctcagctg ctcaggaggc tgagtcagga    240
gaatctcttg aacccaggag gtggaggttg tggtgagctg agatggtgcc attgcactcc    300
agcctgggca acaagagtga aactccttct caaaaaaaaa aaaaaaaaaa aaaaaaaagg    360
cattcggttt taaaagggaa gcag                                          384

<210> SEQ ID NO 479
<211> LENGTH: 13
<212> TYPE: DNA
<213> ORGANISM: Artificial
<220> FEATURE:
<223> OTHER INFORMATION: Primer

<400> SEQUENCE: 479
cctccctaca gaa                                                       13

<210> SEQ ID NO 480
<211> LENGTH: 18
<212> TYPE: DNA
<213> ORGANISM: Artificial
<220> FEATURE:
<223> OTHER INFORMATION: Primer

<400> SEQUENCE: 480
cgcccggcct tcatttct                                                  18

<210> SEQ ID NO 481
<211> LENGTH: 21
<212> TYPE: DNA
<213> ORGANISM: Artificial
<220> FEATURE:
<223> OTHER INFORMATION: Primer

<400> SEQUENCE: 481
gagactttca tttctaagat g                                              21
```